(12) United States Patent
Kelley et al.

(10) Patent No.: US 12,303,898 B2
(45) Date of Patent: May 20, 2025

(54) MICROFLUIDIC DEVICES AND METHODS OF USE

(71) Applicant: The Governing Council of the University of Toronto, Toronto (CA)

(72) Inventors: Shana Olwyn Kelley, Toronto (CA); Edward Sargent, Toronto (CA); David Philpott, Toronto (CA); Peter Aldridge, Toronto (CA); Stephane Angers, Mississauga (CA); Jason Moffat, Toronto (CA); Barbara Mair, Toronto (CA); Sanna Masud, Scarborough (CA)

(73) Assignee: The Governing Council of the University of Toronto, Toronto (CA)

( * ) Notice: Subject to any disclaimer, the term of this patent is extended or adjusted under 35 U.S.C. 154(b) by 1092 days.

(21) Appl. No.: 17/260,099

(22) PCT Filed: Jul. 15, 2019

(86) PCT No.: PCT/CA2019/050971
§ 371 (c)(1),
(2) Date: Jan. 13, 2021

(87) PCT Pub. No.: WO2020/010471
PCT Pub. Date: Jan. 16, 2020

(65) Prior Publication Data
US 2021/0308679 A1 Oct. 7, 2021

Related U.S. Application Data

(60) Provisional application No. 62/697,700, filed on Jul. 13, 2018.

(51) Int. Cl.
*B01L 3/00* (2006.01)
*A47L 15/42* (2006.01)
(Continued)

(52) U.S. Cl.
CPC ... *B01L 3/502761* (2013.01); *B01L 3/502707* (2013.01); *B01L 3/50273* (2013.01);
(Continued)

(58) Field of Classification Search
CPC ......... B01L 3/502761; B01L 3/502707; B01L 3/50273; B01L 2200/0652;
(Continued)

(56) References Cited

U.S. PATENT DOCUMENTS

| 7,807,454 B2 | 10/2010 | Oh et al. |
| 2008/0124779 A1* | 5/2008 | Oh ........................... B03C 1/32 |
| | | 435/308.1 |

(Continued)

OTHER PUBLICATIONS

Brinkman, E. K., Chen, T., Amendola, M. & van Steensel, B. Easy quantitative assessment of genome editing by sequence trace decomposition. Nucleic Acids Res. 42, e168 e168 (2014).
(Continued)

*Primary Examiner* — Jennifer Wecker
*Assistant Examiner* — Oyeleye Alexander Alabi
(74) *Attorney, Agent, or Firm* — Smart & Biggar LP; Carmela De Luca

(57) ABSTRACT

Microfluidic devices, kits systems and methods are provided for high throughput phenotypic separation of magnetically labelled cell samples. The devices and methods can be used for example to sort cells based on level of target marker and to sort screen cells, such as CRISPR screen cells and other screens with a large number of target cells, to isolate target cells and putative genetic modifiers.

10 Claims, 29 Drawing Sheets

(51) Int. Cl.

| | |
|---|---|
| A61L 27/16 | (2006.01) |
| A61L 27/56 | (2006.01) |
| B01F 23/00 | (2022.01) |
| B01F 23/41 | (2022.01) |
| B01F 101/23 | (2022.01) |
| B01L 7/00 | (2006.01) |
| B01L 9/00 | (2006.01) |
| B03C 1/01 | (2006.01) |
| B03C 1/033 | (2006.01) |
| B03C 1/28 | (2006.01) |
| B23Q 17/24 | (2006.01) |
| C07K 14/705 | (2006.01) |
| C08F 220/56 | (2006.01) |
| C08L 33/26 | (2006.01) |
| C12M 1/00 | (2006.01) |
| C12M 1/34 | (2006.01) |
| C12M 3/06 | (2006.01) |
| C12N 15/10 | (2006.01) |
| C12Q 1/04 | (2006.01) |
| C12Q 1/18 | (2006.01) |
| C12Q 1/6844 | (2018.01) |
| C12Q 1/686 | (2018.01) |
| G01N 1/31 | (2006.01) |
| G01N 21/17 | (2006.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/543 | (2006.01) |
| G01N 33/68 | (2006.01) |
| G01N 33/74 | (2006.01) |
| G01N 35/00 | (2006.01) |
| G01N 35/04 | (2006.01) |
| G01N 35/10 | (2006.01) |
| G06T 7/00 | (2017.01) |
| G06T 7/90 | (2017.01) |
| G16H 20/60 | (2018.01) |
| G16H 40/63 | (2018.01) |
| H10K 10/46 | (2023.01) |
| H10K 85/00 | (2023.01) |
| H10K 85/20 | (2023.01) |

(52) U.S. Cl.
CPC ............ *B03C 1/01* (2013.01); *B03C 1/0332* (2013.01); *B03C 1/288* (2013.01); *C12M 23/16* (2013.01); *C12M 47/04* (2013.01); *C12N 15/1058* (2013.01); *G01N 33/54333* (2013.01); *B01L 2200/0652* (2013.01); *B01L 2300/0816* (2013.01); *B01L 2300/0864* (2013.01); *B01L 2300/12* (2013.01); *B01L 2400/043* (2013.01); *B03C 2201/18* (2013.01); *B03C 2201/26* (2013.01)

(58) Field of Classification Search
CPC ..... B01L 2300/0816; B01L 2300/0864; B01L 2300/12; B01L 2400/043; B03C 1/01; B03C 1/0332; B03C 1/288; B03C 2201/18; B03C 2201/26; C12M 23/16; C12M 47/04; C12N 15/1058; G01N 33/54333
See application file for complete search history.

(56) References Cited

U.S. PATENT DOCUMENTS

2013/0189755 A1    7/2013  Han et al.
2018/0280977 A1*  10/2018  Baday ..................... B03C 1/32

OTHER PUBLICATIONS

Hsiau, T. et al. Inference of CRISPR edits from sanger trace data. bioRxiv 251082 (2018). doi:10.1101/251082.
Petersen, T. N., Brunak, S., von Heijne, G. & Nielsen, H. SignalP 4.0: discriminating signal peptides from transmembrane regions. Nat. Methods 8, 785 6 (2011).
Gogleva, A., Drost, H.-G. & Schornack, S. SecretSanta: flexible pipelines for functional secretome prediction. Bioinformatics 34, 2295 2296 (2018).
Burdukiewicz, M., Sobczyk, P., Chilimoniuk, J., Gagat, P. & Mackiewicz, P. Prediction of signal peptides in proteins from malaria parasites. Int. J. Mol. Sci. 19, 3709 (2018).
Käll, L., Krogh, A. & Sonnhammer, E. L. L. A combined transmembrane topology and signal peptide prediction method. J. Mol. Biol. 338, 1027 36 (2004).
Mahla, R. S. Stem Cells Applications in Regenerative Medicine and Disease Therapeutics. Int J Cell Biol 2016, 6940283, doi:10.1155/2016/6940283 (2016).
Wright, A. V., Nunez, J. K. & Doudna, J. A. Biology and Applications of CRISPR Systems:Harnessing Nature's Toolbox for Genome Engineering. Cell 164, 29-44, doi: 10.1016/j.cell.2015.12.035 (2016).
Wang, T., Yu, H., Hughes, N. W., Liu, B., Kendirli, A., Klein, K., Chen, W. W., Lander, E. S. & Sabatini, D. M. Gene Essentiality Profiling Reveals Gene Networks and Synthetic Lethal Interactions with Oncogenic Ras. Cell 168, 890-903 e815(2017).
Tibbe, A. G., de Grooth, B. G., Greve, J., Liberti, P. A., Dolan, G. J. & Terstappen, L. W. Optical tracking and detection of immunomagnetically selected and aligned cells. Nat Biotechnol 17, 1210-1213, doi:10.1038/70761 (1999).
Tibbe, A. G., de Grooth, B. G., Greve, J., Dolan, G. J., Rao, C. & Terstappen, L. W. Magnetic field design for selecting and aligning immunomagnetic labeled cells. Cytometry 47, 163-172 (2002).
Adams, J. D., Kim, U. & Soh, H. T. Multitarget magnetic activated cell sorter. Proc Natl Acad Sci U S A 105, 18165-18170, doi: 10.1073/pnas.0809795105 (2008).
Inglis, D. W., Riehn, R., Austin, R. H. & Sturm, J. C. Continuous microfluidic immunomagnetic cell separation. Appl Phys Lett 85, 5093-5095, doi:10.1063/1.1823015 (2004).
Amalou, F. & Gijs, M. in Proceedings of IEEE Sensors. 753-756 vol. 752.
Mair, Babara, et al., Scalable, FACS-Free Genome-Wide Phenotypic Screening, EMBL Microfluidics Conference .2018. Jul. 15-17, 2018. Heidelberg, Germany and ELRIG conference CRISPR in Drug Discovery 2019: From Targets to Therapeutics Feb. 27-28, 2019, Oxford, U.
International Search Report and Written Opinion, PCT/CA2019/050971, Sep. 10, 2019.
Jeong Won Park, Nae-Rym Lee, Sung Mok Cho, Moon Youn Jung, Chunhwa Ihm, Dae-Sik Lee 1-10, 12-52, and 54-60, 62-90 "Microdevice for Separation of Circulating Tumor Cells Using Embedded Magnetophoresis with V-shaped Ni—Co Nanowires and /mmuno-nanomagnetic Beads" ETRI Journal, 37(2). Apr. 2015.pp 233-240. Whole document.

(56) References Cited

OTHER PUBLICATIONS

Dae-Sik Lee; Jeong Won Park; Nae-Lim Lee; Mun Yeon Jung; Sung-Mok Cho "Fabrication of Microdevices for Separation of Circulating Tumor Cell Using Lateral Magnetophoresis and /mmunomagnelic Nanobeads" Sensors, 2013 IEEE. Date Added to IEEE Xplore: Dec. 19, 2013. DOI: 10. I 109/ICSENS.2013. 6688454. Whole docwnent.
Han, X. et al. Microfluidic cell deformability assay for rapid and efficient kinase screening with the CRISPR-Cas9 system. Angew. Chemie Int. Ed. 55, 8561 8565 (2016).
Aldridge, P. M. et al. Prismatic deflection of live tumor cells and cell clusters. ACS Nano 12, 12692 12700 (2018).
Trounson, A. & McDonald, C. Stem Cell Therapies in Clinical Trials: Progress and Challenges. Cell Stem Cell 17, 11-22, doi:10. 1016/j.stem.2015.06.007 (2015).
Burr, M. L. et al. CMTM6 maintains the expression of PD-L1 and regulates anti-tumour immunity. Nature 549, 101 105 (2017).
Mezzadra, R. et al. Identification of CMTM6 and CMTM4 as PD-L1 protein regulators. Nature 549, 106 110 (2017).
Binek, A. et al. Flow cytometry has a significant impact on the cellular metabolome. J. Prot. Res. 18, 169-181 (2019).
Llufiro, E., Wang, L., Naser, F.J., Patti, G.J. Sorting cells alters their redox state and cellular metabolome. Redox Biology 16, 381-387 (2018).
Brockmann, M. et al. Genetic wiring maps of single-cell protein states reveal an off-switch for GPCR signalling. Nature 546, 307 311 (2017).
Wroblewska, A. et al. Protein barcodes enable high-dimensional single-cell CRISPR screens. Cell 175, 1141-1155.e16 (2018).
De Groot, R., Lüthi, J., Lindsay, H., Holtackers, R. & Pelkmans, L. Large-scale image-based profiling of single-cell phenotypes in arrayed CRISPR-Cas9 gene perturbation screens. Mol. Syst. Biol. 14, e8064 (2018).
Haney, M. S. et al. Identification of phagocytosis regulators using magnetic genome-wide CRISPR screens. Nat. Genet. 50, 1716 1727 (2018).
Parnas, O. et al. A Genome-wide CRISPR screen in primary immune cells to dissect regulatory networks. Cell 162, 675 686 (2015).
Han, X. et al. CRISPR-Cas9 delivery to hard-to-transfect cells via membrane deformation. Sci. Adv. 1, e1500454 (2015).
Matlung, H. L., Szilagyi, K., Barclay, N. A. & van den Berg, T. K. The CD47-SIRPa signaling axis as an innate immune checkpoint in cancer. Immunol. Rev. 276, 145 164 (2017).
Weiskopf, K. Cancer Immunotherapy Targeting the CD47/SIRPa axis. Eur. J. Cancer 76, 100-109 (2017).
Advani, R. et al. CD47 blockade by Hu5F9-G4 and rituximab in non-N. Engl. J. Med. 379, 1711 1721 (2018).
Kong, F. et al. CD47: a potential immunotherapy target for eliminating cancer cells. Clin. Transl. Oncol. 18, 1051 1055 (2016).
Seiffert, M. et al. Human signal-regulatory protein is expressed on normal, but not on subsets of leukemic myeloid cells and mediates cellular adhesion involving its counterreceptor CD47. Blood 94, 3633 43 (1999).
Leclair, P. et al. CD47-ligation induced cell death in T-acute lymphoblastic leukemia. Cell Death Dis. 9, 544 (2018).
Carette, J. E. et al. Ebola virus entry requires the cholesterol transporter Niemann-Pick C1. Nature 477, 340 3 (2011).
Bürckstümmer, T. et al. A reversible gene trap collection empowers haploid genetics in human cells. Nat. Methods 10, 965 971 (2013).
Lee, S.-E. et al. Proteogenomic analysis to identify missing proteins from haploid cell lines. Proteomics 18, e1700386 (2018).
Paulo, J. A. & Gygi, S. P. Isobaric tag-based protein profiling of a nicotine-treated alpha7 nicotinic receptor-null human haploid cell line. Proteomics 18, e1700475 (2018).
Hart, T. et al. High-resolution CRISPR screens reveal fitness genes and genotype-specific cancer liabilities. Cell 163, 1515 1526 (2015).
Hart, T. et al. Evaluation and design of genome-wide CRISPR/SpCas9 knockout screens. G3 7, 2719 2727 (2017).
Mair, B. et al. Essential gene profiles for human pluripotent stem cells identify uncharacterized genes and substrate dependencies. Cell Rep. 27, 599-615.e12 (2019).
Colic, M. et al. Identifying chemogenetic interactions from CRISPR knockout screens with drugZ. bioRxiv 232736 (2019). doi:10.1101/232736.
Logtenberg, M. E. W. et al. Glutaminyl cyclase is an enzymatic modifier of the CD47-SIRPa axis and a target for cancer immunotherapy. Nat. Med. 25, 612 619 (2019).
Cynis, H. et al. Isolation of an isoenzyme of human glutaminyl cyclase: retention in the golgi complex suggests involvement in the protein maturation machinery. J. Mol. Biol. 379, 966 980 (2008).
Stephan, A. et al. Mammalian glutaminyl cyclases and their isoenzymes have identical enzymatic characteristics. FEBS J. 276, 6522 36 (2009).
Hatherley, D. et al. Paired receptor specificity explained by structures of signal regulatory proteins alone and complexed with CD47. Mol. Cell 31, 266 277 (2008).
Ho, C.C. M. et al. "Velcro" engineering of high affinity CD47 ectodomainas signal regulatory protein a (SIRPa) antagonists that enhance antibody-dependent cellular phagocytosis. J. Biol. Chem. 290, 12650-12663 (2015).
Pozzi, C., Di Pisa, F., Benvenuti, M. & Mangani, S. The structure of the human glutaminyl cyclase-SEN177 complex indicates routes for developing new potent inhibitors as possible agents for the treatment of neurological disorders. J. Biol. Inorg. Chem. 23, 1219 1226 (2018).
Ramsbeck, D. et al. Structure-activity relationships of benzimidazole-based glutaminyl cyclase inhibitors featuring a heteroaryl scaffold. J. Med. Chem. 56, 6613 25 (2013).
Lues, I. et al. A phase 1 study to evaluate the safety and pharmacokinetics of PQ912, a glutaminyl cyclase inhibitor, in healthy subjects. 1, 182 195 (2015).
Hoffmann, T. et al. Glutaminyl cyclase inhibitor PQ912 improves cognition in mouse models of Alizheimer's desease-studies on relation to effective target occupancy. J. Pharmacol. Exp. Ther. 362, 119-130 (2017).
Kumar, A. & Bachhawat, A. K. Pyroglutamic acid: Throwing light on a lightly studied metabolite.Curr. Sci. 102, 288 297 (2012).
Kehlen, A. et al. N-terminal pyroglutamate formation in CX3CL1 is essential for its full biologic activity. Biosci. Rep. 37, (2017).
Cynis, H. et al. The isoenzyme of glutaminyl cyclase is an important regulator of monocyte infiltration under inflammatory conditions. EMBO Mol. Med. 3, 545 558 (2011).
Leonidas, D. D. et al. Refined crystal structures of native human angiogenin and two active site variants: implications for the unique functional properties of an enzyme involved in neovascularisation during tumour growth. J. Mol. Biol. 285, 1209 33 (1999).
Deuse, T. et al. Hypoimmunogenic derivatives of induced pluripotent stem cells evade immune rejection in fully immunocompetent allogeneic recipients. Nat. Biotechnol. 37, 252 258 (2019).
Uhlen, M. et al. A pathology atlas of the human cancer transcriptome. Science 357, eaan2507 (2017).
Sasaki, S., Futagi, Y., Kobayashi, M., Ogura, J. & Iseki, K. Functional characterization of 5-oxoproline transport via SLC16A1/MCT1. J. Biol. Chem. 290, 2303 2311 (2015).
Boix, E. et al. Role of the N terminus in RNase A homologues: differences in catalytic activity,ribonuclease inhibitor interaction and cytotoxicity. J. Mol. Biol. 257, 992 1007 (1996).
Liao, Y.-D. et al. The structural integrity exerted by N-terminal pyroglutamate is crucial for the cytotoxicity of frog ribonuclease from Rana pipiens. Nucleic Acids Res. 31, 5247 55 (2003).
La Mendola, D. et al. Copper binding to naturally occurring, lactam form of angiogenin differs from that to recombinant protein, affecting their activity. Metallomics 8, 118 24 (2016).
Ren, Y. et al. A simple and reliable PDMS and SU-8 irreversible bonding 5 method and its application on a microfluidic-MEA device for neuroscience research. Micromachines 6, 1923 1934 (2015).
Luk, V. N., Mo, G. C. & Wheeler, A. R. Pluronic additives: a solution to sticky problems in digital microfluidics. Langmuir 24, 6382 6389 (2008).

\* cited by examiner

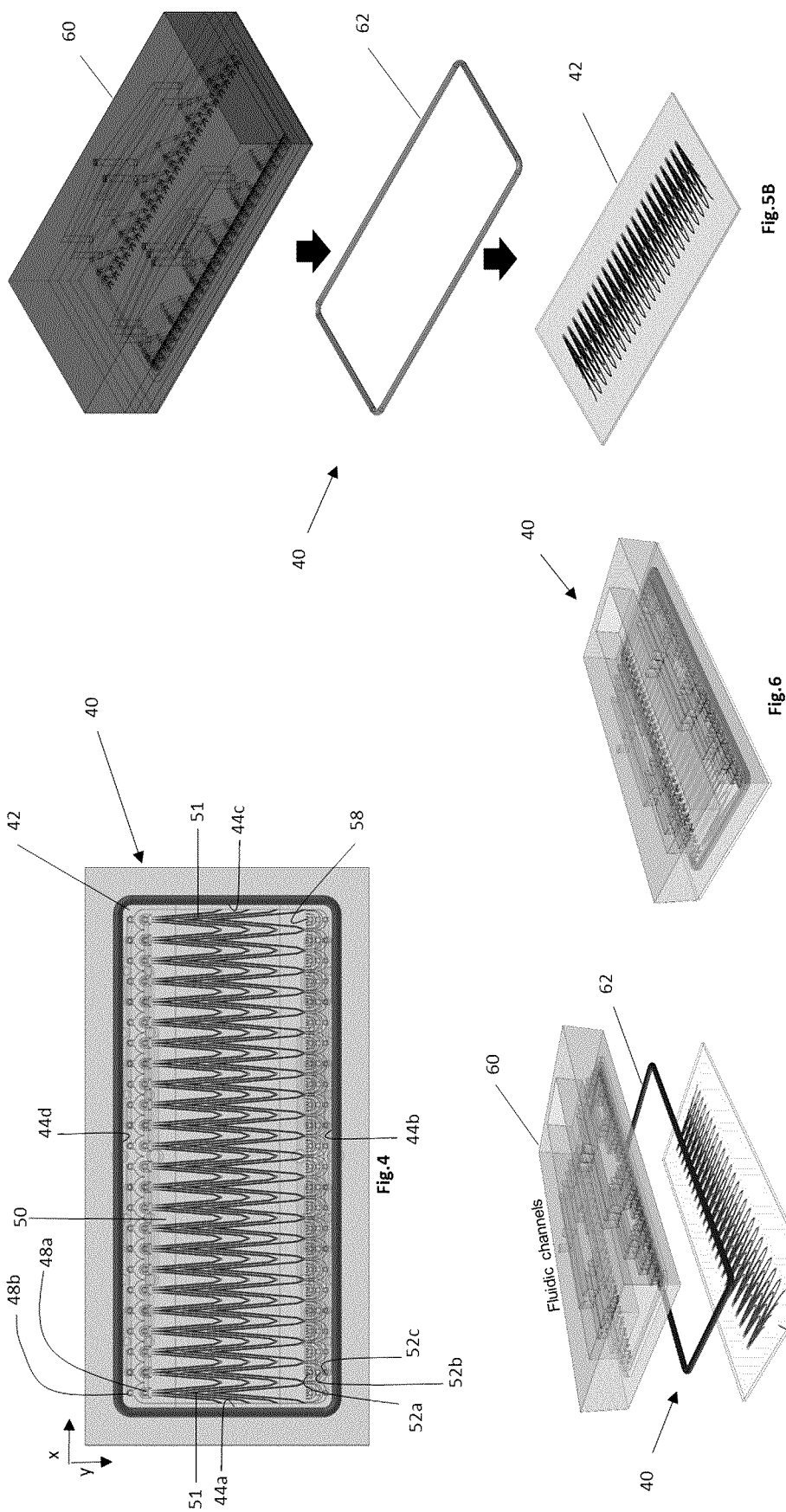

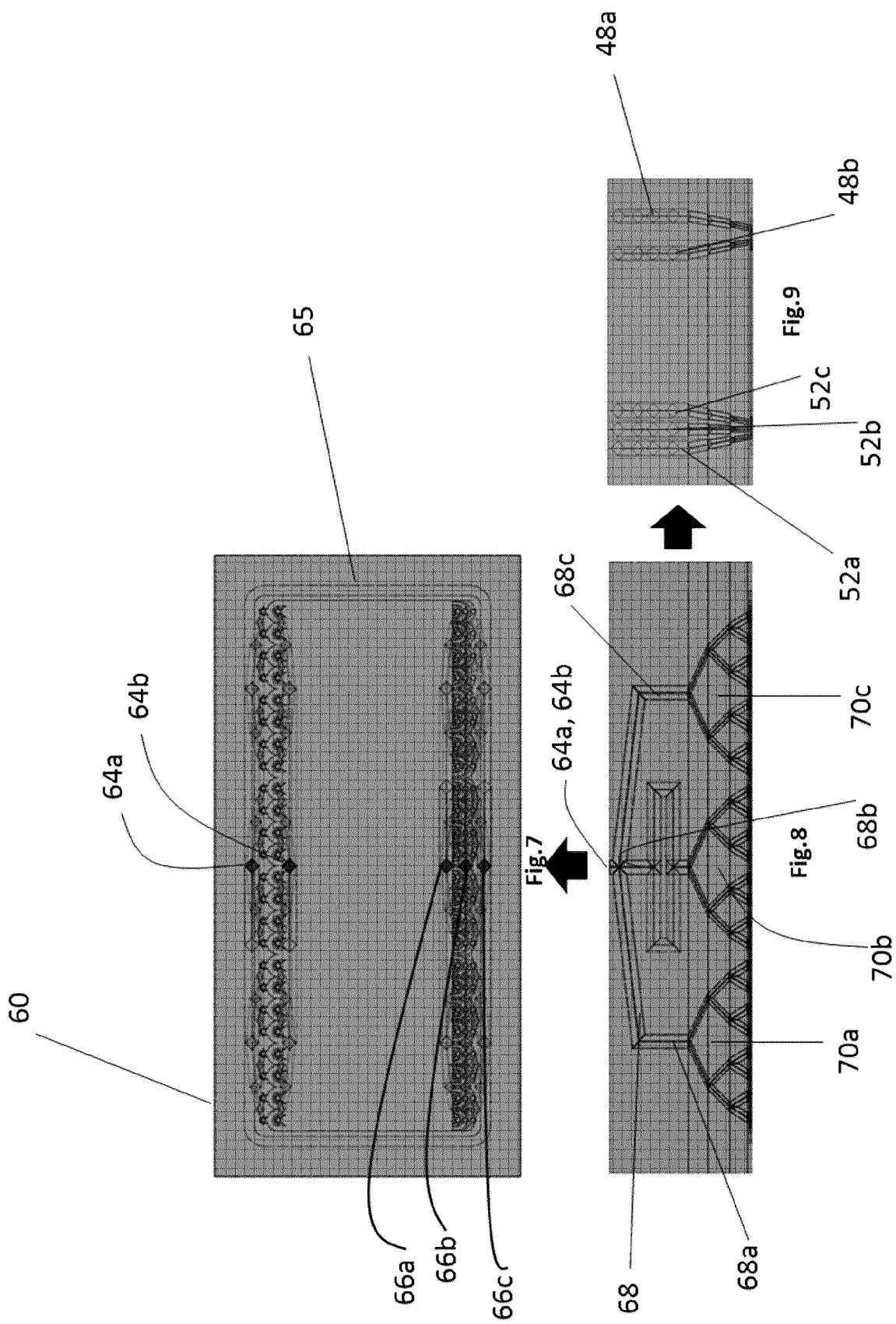

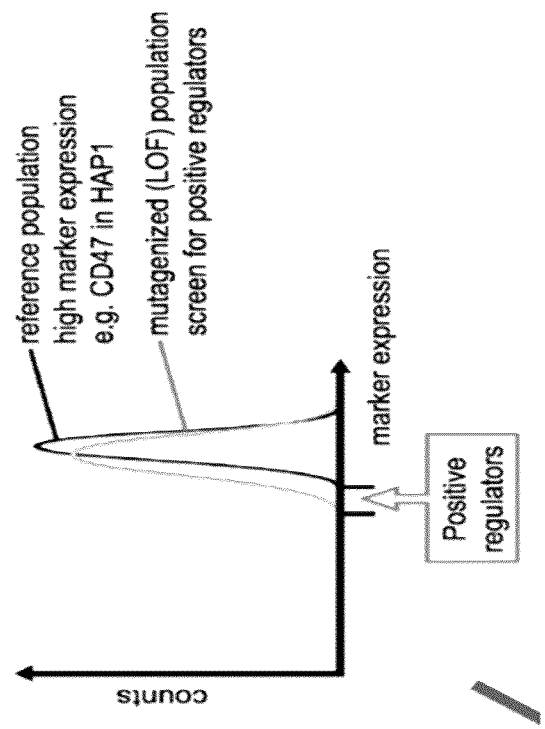
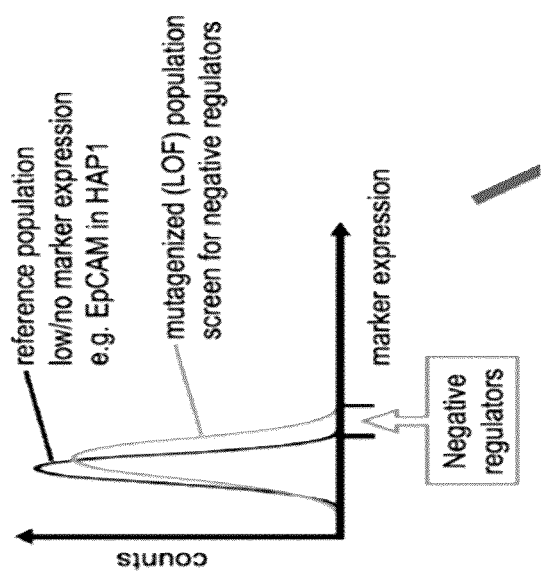
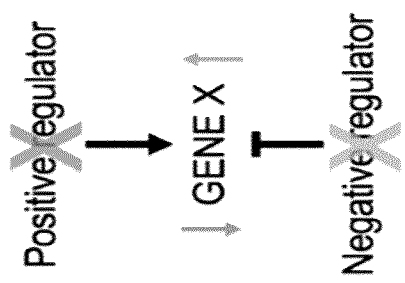
Fig.11A

| | % cells sorted | | | |
|---|---|---|---|---|
| flow rate | replicate | low/zero | medium | high |
| 4 ml/h | 1 | 5.9 | 61.2 | 32.9 |
| | 2 | 3.9 | 64.3 | 31.8 |
| | 3 | 4.7 | 76.1 | 19.1 |
| | mean | 4.8 | 67.2 | 28.0 |
| 6 ml/h | 1 | 12.6 | 79.4 | 8.1 |
| | 2 | 9.7 | 74.3 | 16.0 |
| | 3 | 5.3 | 91.4 | 3.3 |
| | mean | 9.2 | 81.7 | 9.1 |
| 8 ml/h | 1 | 11.0 | 85.6 | 3.4 |
| | 2 | 17.4 | 77.0 | 5.7 |
| | 3 | 10.3 | 88.9 | 0.8 |
| | mean | 12.9 | 83.8 | 3.3 |

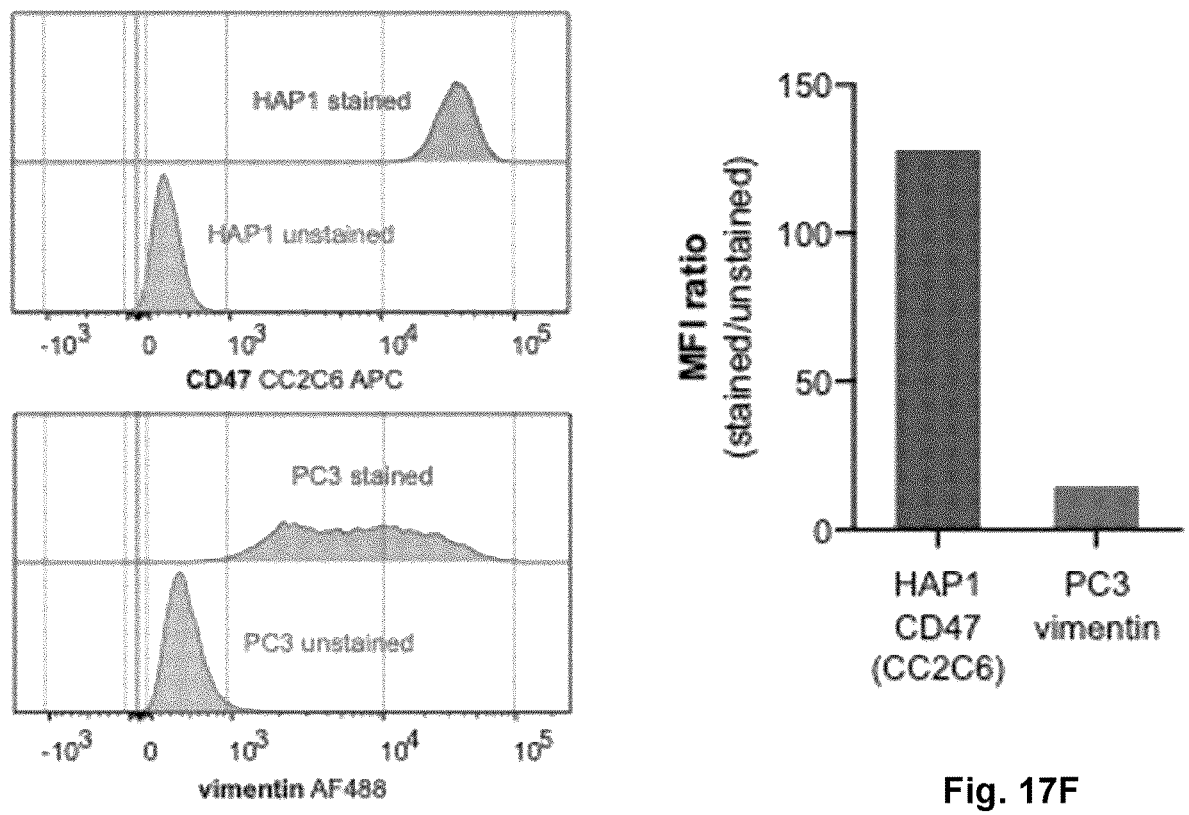
Fig. 17E
Fig. 17F
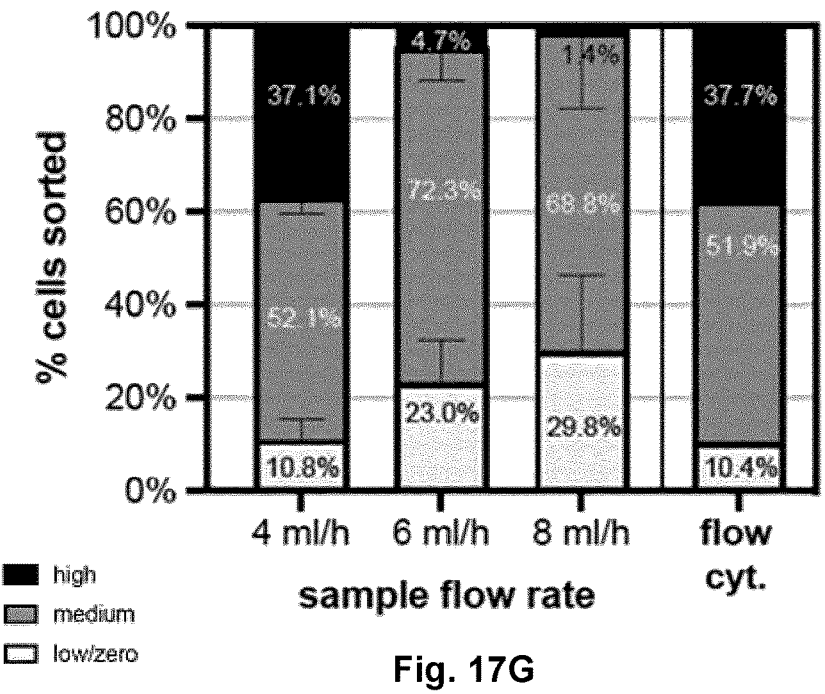
Fig. 17G

MICROFLUIDIC DEVICES AND METHODS OF USE

RELATED APPLICATIONS

This is a Patent Cooperation Treaty Application which claims the benefit of 35 U.S.C. § 119 based on the priority of U.S. Provisional Patent Application No. 62/697,700, filed Jul. 13, 2018 which is incorporated herein by reference in its entirety.

FIELD

The present disclosure relates to microfluidic devices and methods relating thereto for the immunomagnetic separation of cell samples into subpopulations based on marker levels and in particular to separation and isolation of rare altered phenotypes produced in screens such as genetic screens for example those produced in CRISPR genetic screens.

BACKGROUND

Phenotypic genetic screens produce large numbers of cells that can be surveyed to isolate rare altered phenotypes using for example antibodies targeting specific markers of interest. Phenotypic changes in genetically altered cells can then be detected by monitoring changes in levels of antibody binding. Fluorescence-activated cell sorting (FACS) is the gold standard for sorting and isolation of antibody-labeled cells, but suffers from limited throughput for high-coverage genome-scale screening applications, resulting in reduced cell viability or necessitating cell fixation due to long sorting times. In addition, it requires advanced, costly instrumentation and can induce perturbations in cellular metabolism and function that can influence the results obtained[4-5]. Thus, while phenotype-based genetic screens[2-3,6-10] can facilitate the identification of regulators of therapeutically relevant proteoforms detected with labelled probes, they are less common compared to proliferation-based screens because of the challenges related to implementation. Rapid and robust selection approaches for targeted capture of cells, including live cells, are required to realize the full potential of phenotype-based genome-scale screens for functional discovery and further annotation of the human genome.

Microfluidic approaches that offer precise control of forces and flows at length scales comparable to most cells, have potential to manipulate or fractionate cells, such as those from phenotype-based screens. For example, membrane deformation induced in narrow microfluidic channels has been used to increase the permeability, and thus Cas9 delivery efficiency, in hard-to-transfect cells[11]. More recently, microfluidic sorting has been applied to a CRISPR loss-of-function screen, separating cells with increased deformability to potentially identify regulators of genes which promote a metastatic phenotype[12]. U.S. Pat. No. 8,071,054 describes an invention providing a microfluidic device employing one or more sorting stations for separating target species from other species in a sample through magnetophoresis. Aldridge et al. (2018)[13] describe a high-resolution immunomagnetic profiling and separation chip which harnesses a cobalt-based alloy in order to separate a flowing stream of magnetic nanoparticle-bound tumor cells with differential magnetic loading into 10 streams.

However, the major challenge of handling and sorting large collections of cells such as CRISPR-edited cells to identify rare subpopulations based on phenotypic changes has not yet been addressed with a general solution and represents a major unmet need.

SUMMARY

An aspect provides a microfluidic device for sorting or separating a magnetically labelled cell sample into subpopulations based on the level of a target marker, the microfluidic device being a microfluidic chip device or a microfluidic parallelized device as described herein.

In an embodiment, the microfluidic device is a microfluidic chip device comprising:
  at least one inlet for receiving a sample and a buffer;
  a fluidic sorting channel fluidly connected to the at least one inlet, the fluidic sorting channel comprising a plurality of magnetic deflection guides wherein the deflection guides extend along a length of the fluidic sorting channel, wherein each deflection guide comprises a first segment having a first angle relative to the direction of flow and extending outwardly and a second segment having a second angle relative to the direction of flow and extending outwardly, and wherein the first segment intersects the second segment;
  two or more outlets fluidly connected to the fluidic sorting channel, each one of the outlets being configured to receive one subpopulation of the sample.

In one embodiment, the first angle is selected from angles between about 2 to about 20 degrees. In another embodiment, the first angle is about 5 degrees. In one embodiment, the second angle is about 20 to about 90 degrees.

In one embodiment, a magnet is positioned and/or fastened underneath the fluidic sorting channel to generate a magnetic field. More than one magnet can also be positioned or fastened. In one embodiment, the magnet is a neodymium magnet.

In one embodiment, the at least one inlet comprises a buffer inlet and a sample inlet.

In another embodiment, the two or more outlets comprise a first outlet for receiving a first subpopulation of the sample, a second outlet for receiving a second subpopulation of the sample, and a third outlet for receiving a third subpopulation of the sample.

In one embodiment, the deflection guides comprise two sets of deflection guides, wherein the first set is outwardly angled and directed to a first side (e.g. wall) of the fluidic sorting channel and the second set is outwardly angled and directed to a second side (e.g. wall) of the fluidic sorting channel.

In another embodiment,
  high-level subpopulation collection stations are adjacent to the first and second sides of the fluidic sorting channel and fluidly connected to the first outlet, such that the high-level subpopulation collection stations are configured to receive a first subpopulation expressing high levels of a target marker of interest;
  medium-level subpopulation outlets are adjacent to the high-level subpopulation collection stations and fluidly connected to the second outlet, the medium-level subpopulation collection stations being configured to receive a second subpopulation expressing medium levels of a target marker of interest; and
  low-level subpopulation collection stations are positioned between the medium-level subpopulation collection stations and fluidly connected to the third outlet, the low-level subpopulation collection stations being configured to receive a third subpopulation expressing low levels of a target marker of interest.

In another embodiment, the deflection guides comprise cobalt-based magnetic alloy. In another embodiment, the magnetic deflection guides are encapsulated, optionally with a photoresist, resin, polymer or glass.

In another embodiment, the at least one inlet comprises a buffer inlet having bifurcated arms for directing the buffer to the sides of the sample to focus the sample stream. In another embodiment, each of the two or more outlets comprises a collection bin for receiving a corresponding subpopulation of the sample. In another embodiment, the width of each of the bifurcated arms correspond to the sum of the widths of the corresponding collection bins of a first and second outlet.

A further aspect includes a microfluidic parallelized device comprising
- a platform comprising a plurality of magnetic deflection guides;
- a manifold having at least one inlet port and two or more outlet ports; and
- a fluidic sorting channel definable by sealing the manifold on the platform, the fluidic sorting channel being fluidly connectable to the at least one inlet and the two or more outlet ports;
- wherein the deflection guides extend along a length of the fluidic sorting channel, wherein each deflection guide comprises a first segment having a first angle relative to the direction of flow and extending outwardly and a second segment having a second angle relative to the direction of flow and extending outwardly, and wherein the first segment intersects the second segment.

In another embodiment, the magnetic deflection guides are encapsulated, optionally with a photoresist, resin, polymer or glass.

In another embodiment, the manifold comprises an inlet channel fluidly connectable to the at least one inlet port and the fluidic sorting channel, the inlet channel being configured to split a sample or buffer received at the at least one inlet port into a plurality of streams, each stream being directed to the fluidic sorting channel.

In another embodiment, the manifold comprises an outlet channel fluidly connectable to the two or more outlet ports and the fluidic sorting channel, the outlet channel being configured to route each of subpopulations received at the fluidic sorting channel to a corresponding outlet port.

In another embodiment, the microfluidic parallelized device further comprises an O-ring for sealing the manifold to the platform.

In an embodiment, the inlet channel and the outlet channel have square cross-sections. In an embodiment, the inlet channel and the outlet channel comprise a tree structure.

In another embodiment, the deflection guides are grouped into deflection units, such that the deflection units are positioned in parallel on the platform.

In another embodiment, each deflection unit comprises two sets of guides and wherein a first set of guides is outwardly angled and directed to a first side of the platform and a second set of guides is outwardly angled and directed to a second side of the platform.

Another aspect of the present disclosure is a kit comprising a microfluidic device as described herein. In an embodiment, the kit comprises a microfluidic chip device. In another embodiment, the kit comprising a microfluidic parallelized device as described herein.

In another embodiment, the kit further comprises tubing for connecting to the microfluidic chip device.

Also provided is use of a microfluidic device as described herein for identification of modifiers of target marker levels.

A further aspect is use of a microfluidic device described herein for sorting magnetically labeled cells based on their loading with magnetic affinity particles.

A further aspect is a method for manufacturing a microfluidic chip device, comprising:
- providing a fluidic channel for receiving a cell sample; and
- fastening a plurality of magnetic deflection guides to the fluidic channel, wherein each deflection guide comprises a first segment having a first angle and extending outwardly and a second segment having a second angle and extending outwardly, such that first segment intersects the second segment.

In an embodiment, the method further comprises encapsulating the deflection guides. In another embodiment, the deflection guides are encapsulated, with a photoresist, resin, polymer or glass.

In another embodiment, the fastening the plurality of deflection guides to the fluidic channel comprises:
- fastening a magnetic material to the fluidic channel; and
- patterning the magnetic material to define magnetic deflection guides.

In another embodiment, the magnetic material comprises a cobalt-based magnetic alloy or nickel-iron magnetic alloy.

In another embodiment, the first angle is about 2 to about 20 degrees. In another embodiment, the second angle can be about 20 to about 90 degrees. In yet a further embodiment, the difference between the first angle and the second angle is about or at least 5 degrees.

In another embodiment, the deflection guides comprises two sets, each set including about 4 to about 30 guides, for example, each set includes 15 guides.

In another embodiment, the two sets comprises a first set being outwardly angled and directed to a first side and a second set being outwardly angled and directed to a second side, the first and second sides being opposite to each other.

A further aspect is a method for separating or sorting a magnetically labelled cell sample into subpopulations based on levels of a target marker of interest, the method comprising:
- introducing the magnetically labelled cell sample and a buffer into at least one inlet or inlet port of a microfluidic device, the inlet and/or inlet port configured to provide separate substantially parallel streams of the magnetically labelled cell sample and the buffer, the microfluidic device comprising:
  - a fluidic sorting channel, the fluidic sorting channel in communication with a plurality of magnetic deflection guides wherein the deflection guides extend along a length of the fluidic sorting channel, wherein each deflection guide comprises a first segment having a first angle relative to the direction of flow and extending outwardly and a segment having a second angle relative to the direction of flow and extending outwardly, and wherein the first segment intersects the second segment, and
  - a magnet positioned underneath the fluidic sorting channel to generate a magnetic field;
- flowing the magnetically labelled cell sample through the fluidic sorting channel;
- collecting two or more, preferably three, subpopulations from two or more outlets or outlet ports coupled to the fluidic sorting channel, each one of the outlets or outlet ports being configured to receive a subpopulation of the magnetically labelled cell sample wherein the magnetically labelled cell sample comprises a heterogeneous cell sample and magnetic affinity particles comprising with affinity for the target marker directly or indirectly.

In another embodiment, the magnetic affinity particles comprise magnetic particles, optionally magnetic microbeads or nanobeads, and a binding agent such as antibody aptamer, nucleic acid probe or ligand that has affinity for and selectively binds the target marker, or magnetic particles and a secondary binding agent that can indirectly bind the target marker via a binding agent such as an antibody aptamer, nucleic acid probe or ligand, that has affinity for and selectively binds the target marker.

In another embodiment, the magnetic affinity particles comprise magnetic particles selected from streptavidin microbeads or nanobeads or anti-biotin microbeads or nanobeads, anti-fluorochrome microbeads or nanobeads such as anti-FITC, anti-PE or anti-APC microbeads or nanobeads or anti-immunoglobuin microbeads or nanobeads.

In another embodiment, the target marker is a cell surface macromolecule, such as a cell surface protein.

In another embodiment, wherein the heterogeneous cell sample is magnetically labelled by incubating the heterogeneous cell sample with magnetic affinity particles, optionally a binding agent directly conjugated to magnetic beads or a secondary binding agent conjugated to magnetic beads.

In another embodiment, the target marker is an intracellular macromolecule, optionally an intracellular protein, a nucleic acid, optionally DNA or RNA.

In another embodiment, the heterogeneous cell sample is magnetically labelled by incubating the heterogeneous cell sample with a permeabilization agent to permeabilize cells of the heterogeneous cell sample and incubating the permeabilized heterogeneous cell sample with magnetic affinity particles, optionally a binding agent directly conjugated to magnetic beads or a secondary binding agent conjugated to magnetic beads.

In another embodiment, the binding agent is an antibody, optionally a monoclonal antibody, aptamer, nucleic acid probe or ligand.

In another embodiment, the magnetically labelled cell population introduced into the at least one inlet is at a concentration of about $0.5 \times 10^6$ cells/ml to about $1 \times 10^7$ cells/ml, optionally $1 \times 10^6$ cells/mi to about $5 \times 10^6$ cells/mi or any cell concentration between $0.5 \times 10^6$ cells/mi to about $1 \times 10^7$ cells/ml.

In another embodiment, the magnetically labelled cell sample comprises or is expected to comprise greater than or at least 2500, 5000, 10000 or target cells.

In another embodiment, the cell sample and/or buffer is flowed through the fluidic channel using one or more pumps, optionally one or more infusion pumps, rotary pumps, piston pumps, diaphragm pump, gear pumps or syringe pumps, optionally operating in push mode or in withdrawal mode, wherein in withdrawal mode the syringe pumps drive two or more syringes fluidly connected to the two or more outlets or outlet ports.

In another embodiment, each outlet is connected to a collection container, optionally a syringe with a preselected cross sectional area, the cross-sectional area of the syringe, selected to produce a flow rate corresponding to the width of each outlet.

In another embodiment, the microfluidic device comprises three outlets or outlet ports, a first, second and third outlet or outlet port and the method comprises collecting subpopulations comprising a high, medium or low level of the target marker.

In another embodiment, the third outlet (low) is connected to a 20 ml syringe, the second outlet (medium) is connected to a 10 ml syringe and the first outlet is connected to a 3 ml syringe.

In another embodiment, the syringes are driven by the same pump.

In another embodiment, the magnetically labelled sample is introduced into the at least one inlet or inlet port using a sample inlet reservoir and a buffer inlet reservoir, containing the magnetically labelled cell sample and the buffer respectively.

In another embodiment, the microfluidic device comprises a sample inlet and/or sample inlet port and a buffer inlet and/or buffer inlet port, the sample inlet reservoir is fluidly connected to the sample inlet and/or sample inlet port and the buffer inlet reservoir is fluidly connected to the buffer inlet and/or buffer inlet port.

In another embodiment, the magnetically labelled cell sample is flowed in the channel at a rate of 2 ml/hr to 30 ml/hr, optionally about 4 ml/hr, or about 6 ml/hr or about 8 ml/hr or about 10 ml/hr.

In another embodiment, the microfluidic device is the device described herein.

In another embodiment, the flow rate of the buffer and cell sample is configured to produce an approximate 10/80/10% distribution of subpopulations in the high, medium and low outlets or outlet ports.

In another embodiment, the heterogeneous cell sample is subjected to a functional genetic screen optionally a genome-scale functional genetic screen.

The method of any one of any of the above claims, wherein the microfluidic chip device is a run singularly.

The method of any of any of the above claims, wherein a plurality of the microfluidic devices are run in parallel, optionally 2-50, or any whole number between and including 2 and 50.

The method of any of any of the above claims, wherein a microfluidic parallelized device is used.

The method of any one of any of the above claims wherein the magnetically labelled cell sample comprises at least or about $1 \times 10^7$, $3 \times 10^7$ cells/hr $5 \times 10^7$, $1 \times 108$ or $5 \times 10^8$ cells.

The method of any one of any of the above claims, wherein one or more of the subpopulations is isolated and cultured/expanded and/or subjected to one or more biological assays.

The method of any one of any of the above claims, wherein one or more of subpopulations is subjected to at least one further sorting.

The method of the above claim wherein the at least one further sorting comprises obtaining or isolating a subpopulation that has been sorted, optionally culturing and propagating the subpopulation and resorting (e.g. a secondary sort) the cells according to a method and/or using a device described herein.

The method of the above claim wherein, at least 2 or at least 3 further sorts are performed.

The method of any one of any of the above claims wherein the heterogeneous cell sample is a screen cell sample, optionally a pooled screen cell sample, optionally wherein the screen is selected from a large scale random mutagenesis, RNAi screen, and a genome editing screen.

The method of the above claim, wherein the genome editing screen is selected from a Zinc-finger nuclease screen, a TALEN screen or a CRISPR screen.

The method of any one of the claims above for identifying a putative genetic regulator of a target marker, the method comprising:
  obtaining a heterogeneous cell sample, optionally of genetically edited cells (e.g. where the edited cell has expression is decreased by at least 80% and/or knocked out);
  labelling the heterogeneous cell sample with a magnetic label to provide a magnetically labelled cell sample;
  introducing the magnetically labelled cell sample and a buffer in to at least one inlet or inlet port of a microfluidic device, the inlet and/or inlet port configured to provide separate substantially parallel streams of the magnetically labelled cell sample and the buffer, the microfluidic device comprising i) a fluidic sorting channel, the fluidic sorting channel in communication with a plurality of magnetic deflection guides wherein the deflection guides extend along a length of the fluidic sorting channel, wherein each deflection guide comprises a first segment having a first angle relative to the direction of flow and extending outwardly and a segment having a second angle relative to the direction of flow and extending outwardly, and wherein the first segment intersects the second segment, and ii) a magnet positioned underneath the fluidic sorting channel to generate a magnetic field;
  flowing the magnetically labelled cell sample through the fluidic sorting channel;
  collecting two or more, preferably three, subpopulations from two or more outlets or outlet ports coupled to the fluidic channel, each one of the outlets or outlet ports being configured to receive a subpopulation of the magnetically labelled cell sample;
  assaying at least one of the two or more subpopulations to identify the putative genetic regulator.

In an embodiment, he genetically edited cells comprise cells from a RNAi screen, a Zinc-finger nuclease screen, a TALEN screen or a CRISPR screen, optionally a CRISPR transcriptional repression screen (CRISPRi) a CRISPR transcriptional activation screen (CRISPRa) or a typical CRISPR knock out screen.

In another embodiment, the CRISPR screen comprises transducing a Cas9 or other CRISPR nuclease expressing cells with a CRISPR lentiviral library, selecting CRISPR edited cells for example by antibiotic selection and passaging under selection.

In another embodiment, the heterogeneous cell sample is prepared by mutagenizing a cell line using a CRISPR library, propagating and selecting CRISPR edited cells, optionally for 5 to 20 doublings, for example 12 doublings, and sorting the cells using a method and/or a microfluidic device, kit or system described herein.

In another embodiment, the CRISPR library comprises multiple guides (sgRNA) per gene and optionally targets upwards of 15000 protein coding genes.

In another embodiment, the heterogeneous cell sample is a pooled cell sample, optionally comprising $10^6$, $10^7$, $10^8$ or $10^9$ cells optionally CRISPR edited cells.

In another embodiment, one or more of the sorted subpopulations is assayed for sgRNA abundance.

In another embodiment, the method comprises isolating genomic DNA from the subpopulation, PCR amplifying and sequencing the sgRNAs and comparing to sgRNA abundance prior to sorting or prior to an earlier sorting.

The method of any one of any of the above claims wherein the magnetically labelled cell sample comprises or is expected to comprise greater than or at least 2500, 5000, 10000 or target cells,
  the heterogeneous cell sample is a biological sample, optionally blood, serum, urine, saliva or a stool preparation.

In another embodiment, the target marker is CD47, CD15 and CD45, CD4 or CD8. In another embodiment, the target marker comprises a post-translational modification.

In another embodiment, the binding agent comprises a protein interactor such as soluble SIRPα.

In another embodiment, the method is for identifying a putative genetic regulator of target marker CD47, the method comprising:
  obtaining a heterogeneous cell sample, optionally of genetically edited cells;
  labelling the heterogeneous cell sample with a magnetic label that labels the target marker to provide a magnetically labelled cell sample;
  introducing the magnetically labelled cell sample and a buffer in to at least one inlet or inlet port of a microfluidic device, the inlet and/or inlet port configured to provide separate substantially parallel streams of the magnetically labelled cell sample and the buffer, the microfluidic device comprising i) a fluidic sorting channel, the fluidic sorting channel in communication with a plurality of magnetic deflection guides wherein the deflection guides extend along a length of the fluidic sorting channel, wherein each deflection guide comprises a first segment having a first angle relative to the direction of flow and extending outwardly and a segment having a second angle relative to the direction of flow and extending outwardly, and wherein the first segment intersects the second segment, and ii) a magnet positioned underneath the fluidic sorting channel to generate a magnetic field;
  flowing the magnetically labelled cell sample through the fluidic sorting channel;
  collecting two or more, preferably three, subpopulations from two or more outlets or outlet ports coupled to the fluidic channel, each one of the outlets or outlet ports being configured to receive a subpopulation of the magnetically labelled cell sample;
  assaying at least one of the two or more subpopulations to identify the putative genetic regulator.

In another embodiment, the binding agent comprises CC2C6s or soluble SIRPα

In another embodiment, the at least one inlet or inlet port comprise a sample inlet or sample inlet port and a buffer inlet and/or buffer inlet port wherein the buffer inlet or buffer inlet port is configured to focus a sample stream.

In another embodiment, the magnet is directly below the sorting channel, optionally abutting the bottom surface of a wafer supporting the magnetic guides, or within 1 cm thereof.

In another embodiment, the cell sample flow rate and the buffer flow rate are substantially equal.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 4 is a cut-away top view of a microfluidic parallelized device according to one example.

FIGS. 5A and 5B are exploded views of the microfluidic parallelized device of FIG. 4.

FIG. 6 is a perspective view of the microfluidic parallelized device of FIG. 5.

FIG. 7 is a top view of a manifold according to one example.

FIG. 8 is a front view of the manifold of FIG. 7.

FIG. 9 is a side view of the manifold of FIG. 7.

FIG. 11A is a schematic of pooled CRISPR-Cas9 screens for the identification of positive and negative regulators of a target marker of interest.

DETAILED DESCRIPTION OF THE DISCLOSURE

Figure 1:
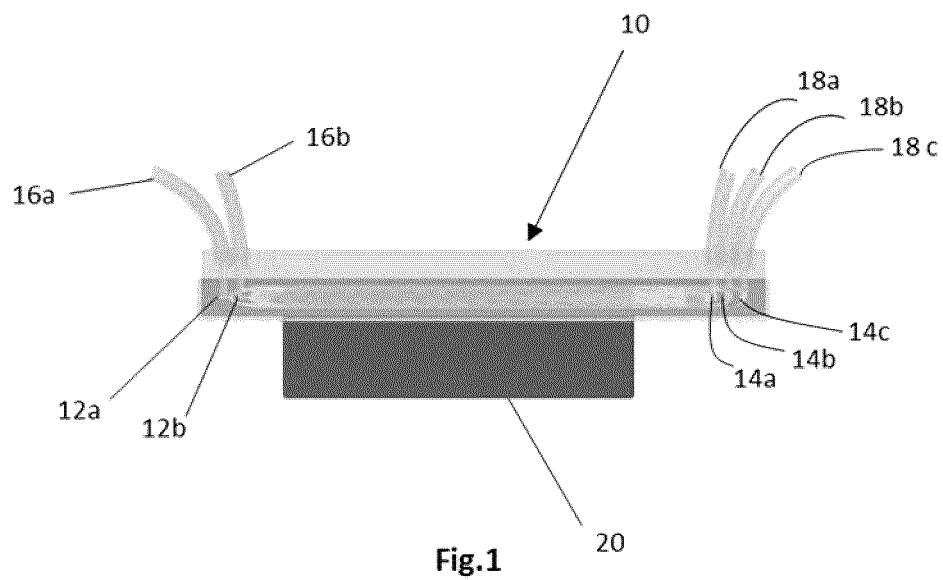
FIG. 1 is a side view of the microfluidic chip device according to one example.

Described herein is a high-throughput microfluidic cell sorting platform. As demonstrated, it can be combined with genome-wide CRISPR-Cas9 loss-of-function screening as an unbiased method for identification of modifiers of protein or biomarker levels. While FACS possesses limited throughput because of the need to process and analyze cellular fluorescence at the single-cell level, the designed devices comprise a network of magnetic guides that sense and deflect cells labeled based on their loading with, for example, antibody-labeled nanoparticles as they travel through the device along with millions of other cells. The present device, which uses a set of magnetic guides with discrete angled segments, is able to preserve high cell viability after sorting as well as high sorting efficiency of target cells with sufficient accuracy to separate phenotypically distinct subpopulations.

I. Definitions

Unless otherwise indicated, the definitions and embodiments described in this and other sections are intended to be applicable to all embodiments and aspects of the present application herein described for which they are suitable as would be understood by a person skilled in the art.

The term "antibody" as used herein is intended to include human antibodies, monoclonal antibodies, polyclonal antibodies, single chain and other chimeric antibodies. The antibody may be from recombinant sources and/or produced in transgenic animals. The antibody in an embodiment comprises a heavy chain variable region or a heavy chain comprising a heavy chain complementarity determining region 1, heavy chain complementarity determining region 2 and heavy chain complementarity determining region 3, as well as a light chain variable region or light chain comprising a light chain complementarity determining region 1, light chain complementarity determining region 2 and light chain complementarity determining region 3.

The term "binding fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

The term "hybridize" as used herein refers to the sequence specific non-covalent binding interaction with a complementary nucleic acid.

The term "level" as used herein refers to an amount (e.g. relative amount or concentration) of a target marker that is detectable or measurable in a cell sample, subpopulation or cell.

The term "polynucleotide", "nucleic acid", "nucleic acid molecule" and/or "oligonucleotide" as used herein refers to a sequence of nucleotide or nucleoside monomers consisting of naturally occurring and/or modified bases, sugars, and intersugar (backbone) linkages, and is intended to include DNA and RNA which can be either double stranded or single stranded, representing the sense or antisense strand.

The term "probe" as used herein refers to a polynucleotide that comprises a sequence of nucleotides that will hybridize specifically to a target nucleic acid sequence. For example the probe comprises at least 18 or more bases or nucleotides that are complementary and hybridize to contiguous bases and/or nucleotides in the target nucleic acid sequence. The length of probe depends on the hybridization conditions and the sequences of the probe and nucleic acid target sequence and can for example be 10-20, 21-70, 71-100 or more bases or nucleotides in length. For example, the PCR product produced with the primers could be used as a probe. The PCR product can be for example be subcloned into a vector and optionally digested and used as a probe. A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U).

The term "subpopulation" as used herein means a portion of a cell sample where the sample is enriched for, and/or the majority of cells of the subpopulation have a more similar level of a target marker compared to another subpopulation in a particular sort. For example, where the cell sample is being sorted in a microfluidic device into distinct subpopulations for example three distinct subpopulations comprising a first or high level outlet or outlet port (high level subpopulation), a second or medium level outlet or outlet port (medium level subpopulation) and a third or low level outlet or outlet port (low level subpopulation), the cells that flow into an outlet are enriched for cells having a particular level of target marker. For example, the majority of the cells that flow into the high level outlet, would have an increased level of the target marker relative to the average level of target marker on cells that flow into a medium level or low level outlet.

The term "target marker" or "target marker of interest" as used herein means any macromolecule or part thereof that is present on or in a cell (e.g. cell surface, transmembrane and intracellular) and which can be recognized by a binding agent that specifically binds the target marker. The target marker can be a macromolecule or a portion thereof, such as a protein or an epitope thereof respectively, for example that comprises a post-translational modification. Post-translational modifications include but are not limited to phosphorylation, glycosylation, ubiquitination, nitrosylation, methylation, acetylation, lipidation and cyclization such pyroglutamyl modification. For example, the target marker may be a post-translational modified residue. A screen can be conducted to identify genetic modifiers that increase and/or decrease the presence of the post-translational modification. The binding agent can be any binding agent that specifically binds the target marker, including but not limited to an antibody, aptamer, ligand or nucleic acid probe. Where the target marker is a post-translational modification of a residue, the binding agent specifically binds the modified residue and/or binding is destroyed by the post translational modification such that a change in the level of the target marker can be distinguished.

The term "selectively hybridize" as used herein refers to hybridization under moderately stringent or highly stringent physiological conditions, which can distinguish related nucleotide sequences from unrelated nucleotide sequences. In nucleic acid hybridization reactions, the conditions used to achieve a particular level of stringency are known to vary, depending on the nature of the nucleic acids being hybridized, including, for example, the length, degree of complementarity, nucleotide sequence composition (e.g., relative GC:AT content), and nucleic acid type, i.e., whether the oligonucleotide or the target nucleic acid sequence is DNA or RNA. Appropriate stringency conditions which promote hybridization are known to those skilled in the art, or can be found in Current Protocols in Molecular Biology, John Wiley & Sons, N.Y. (1989), 6.3.1 6.3.6 and/or Current Protocols in Nucleic Acid Chemistry available at http://onlinelibrary.wiley.com/browse/publications?type=labprotocols. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

As used in this application, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

As used herein "between" is used inclusive of the start end point of the range and is meant to include each number in the range individually, for example the phrase "between 6 to 10", includes the range 6-10 and includes each individually (e.g. 6, 7, 8, 9 and 10) and where not inconsistent all fractions subsumed within the range (e.g. 6.2, 7.4, 8.6, 9.8 etc). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Device

An aspect of the disclosure includes a microfluidic device. In one embodiment, the microfluidic device is a microfluidic chip device.

Figure 2:
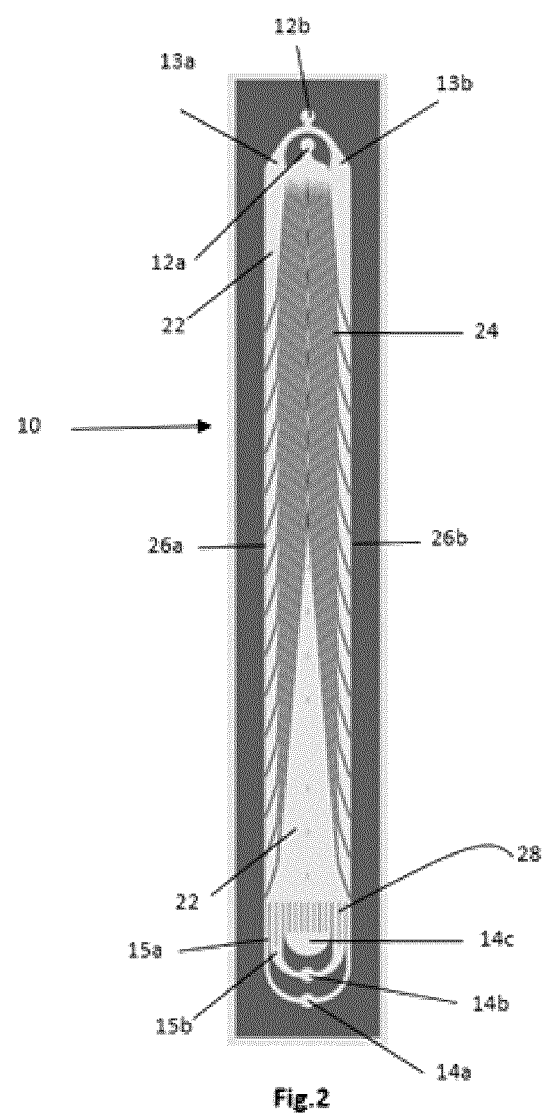
FIG. 2 is a top-down view of the microfluidic chip device of FIG. 1.

Referring to FIGS. 1 and 2, there are shown an exemplary embodiment of a microfluidic chip device 10 for separating a magnetically labelled cell sample into subpopulations based on levels of a target marker.

FIG. 1 shows a side view of the microfluidic chip device 10. The microfluidic chip device 10 has a sample inlet and a buffer inlet. The sample inlet includes an opening 12a.

The buffer inlet includes an opening 12b and bifurcated arms 13a and 13b that direct the buffer to the sides of the sample to focus the sample stream.

In this embodiment, the microfluidic chip device 10 has three outlets 14a, 14b and 14c. Each of the outlets 14a, 14b and 14c is configured to receive one subpopulation of the cell sample.

For example, two inlet reservoirs, one containing a cell sample solution (i.e. a sample inlet reservoir) and one containing a flow focusing buffer, a buffer inlet reservoir) (e.g. HBSS, 2% BSA) can be connected to the two inlets of the microfluidic chip device through tubings 16a and 16b. The outlets 14a, 14b and 14c can be connected to collection containers (such as syringes, etc.) through tubings 18a and 18b.

Figure 3A:
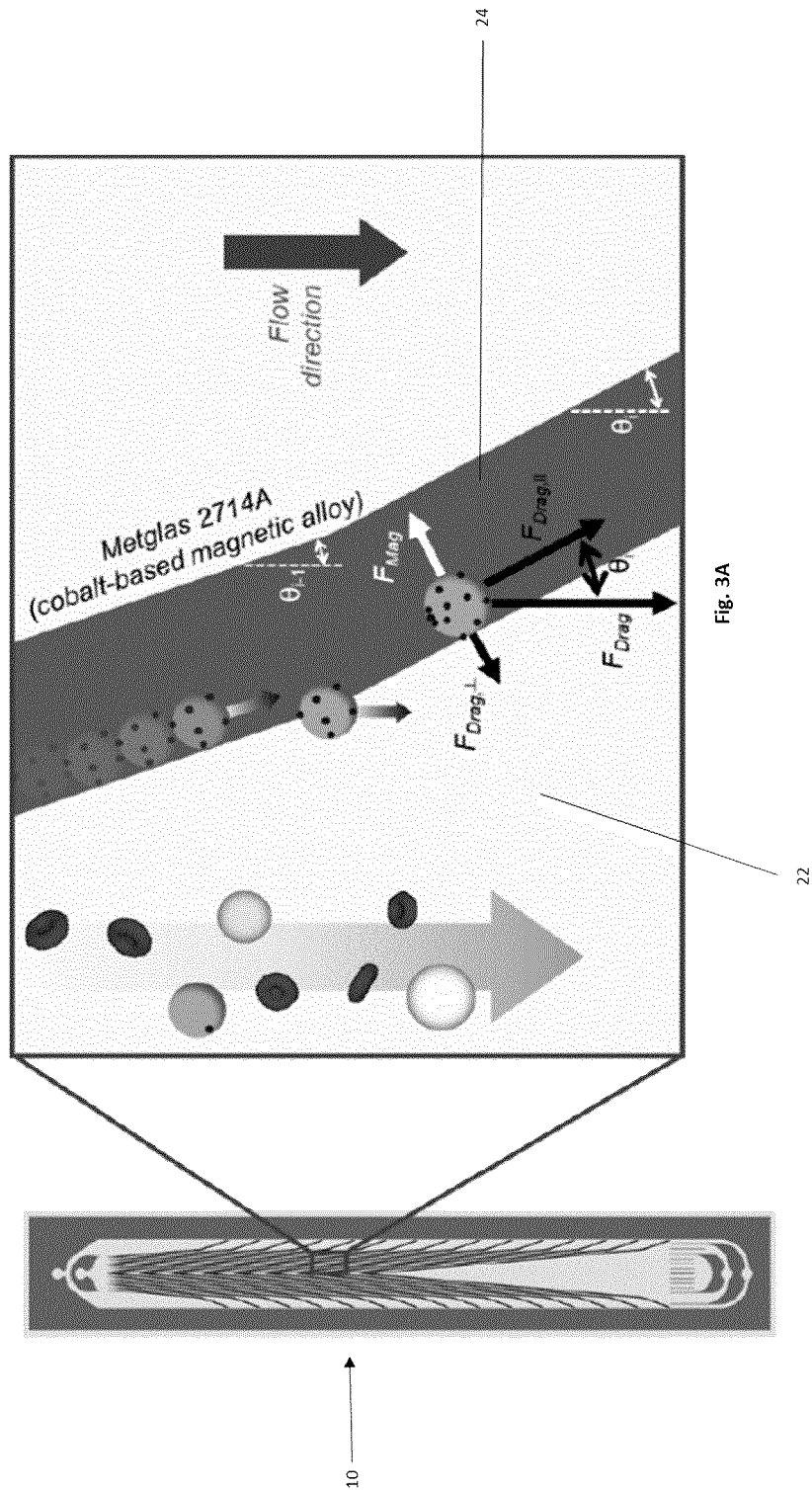
FIGS. 3A, 3B and 3C show close-up views of a deflection guide of the microfluidic chip device of FIG. 2.
Figure 3B:
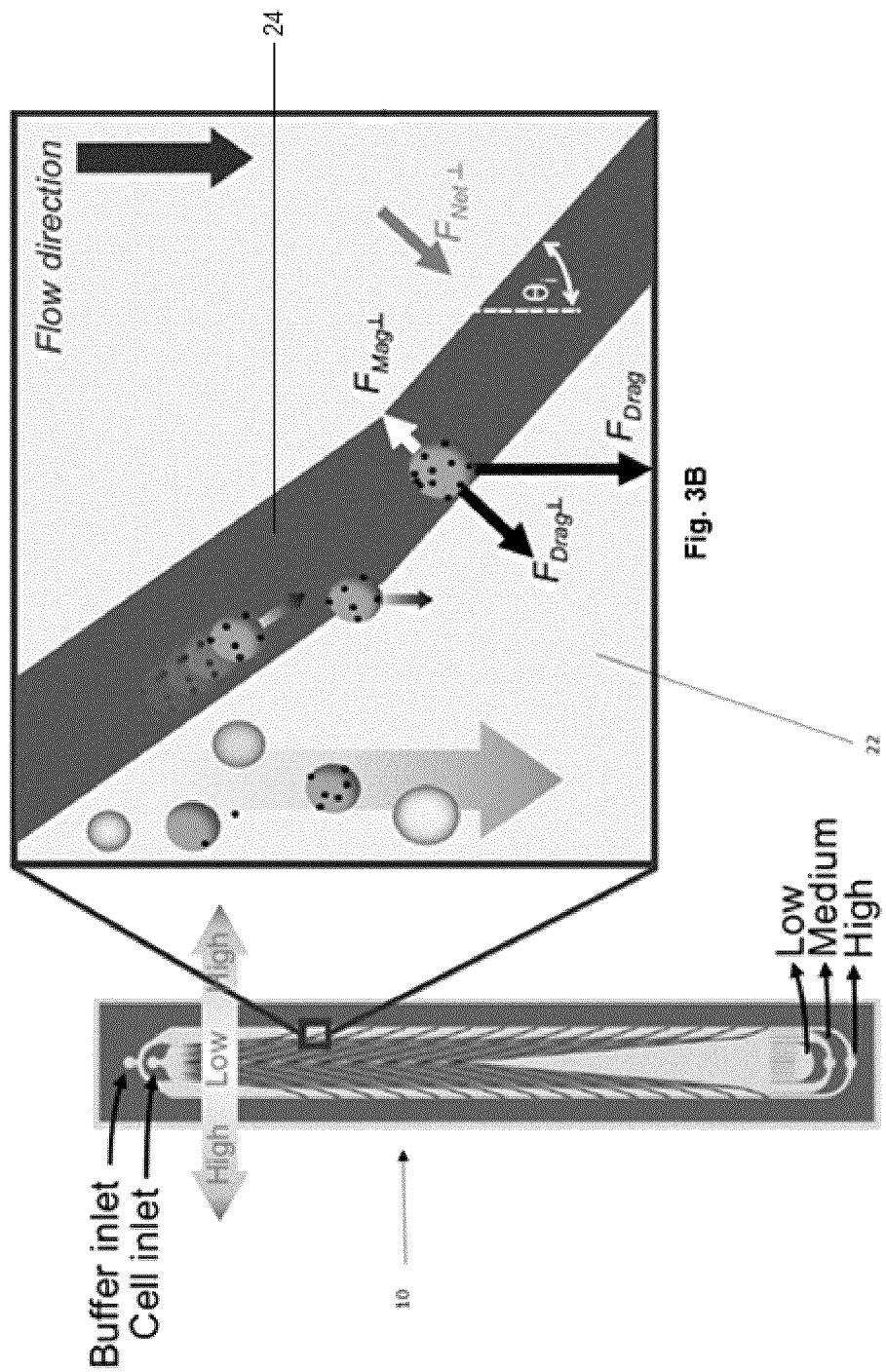
Figure 3C:
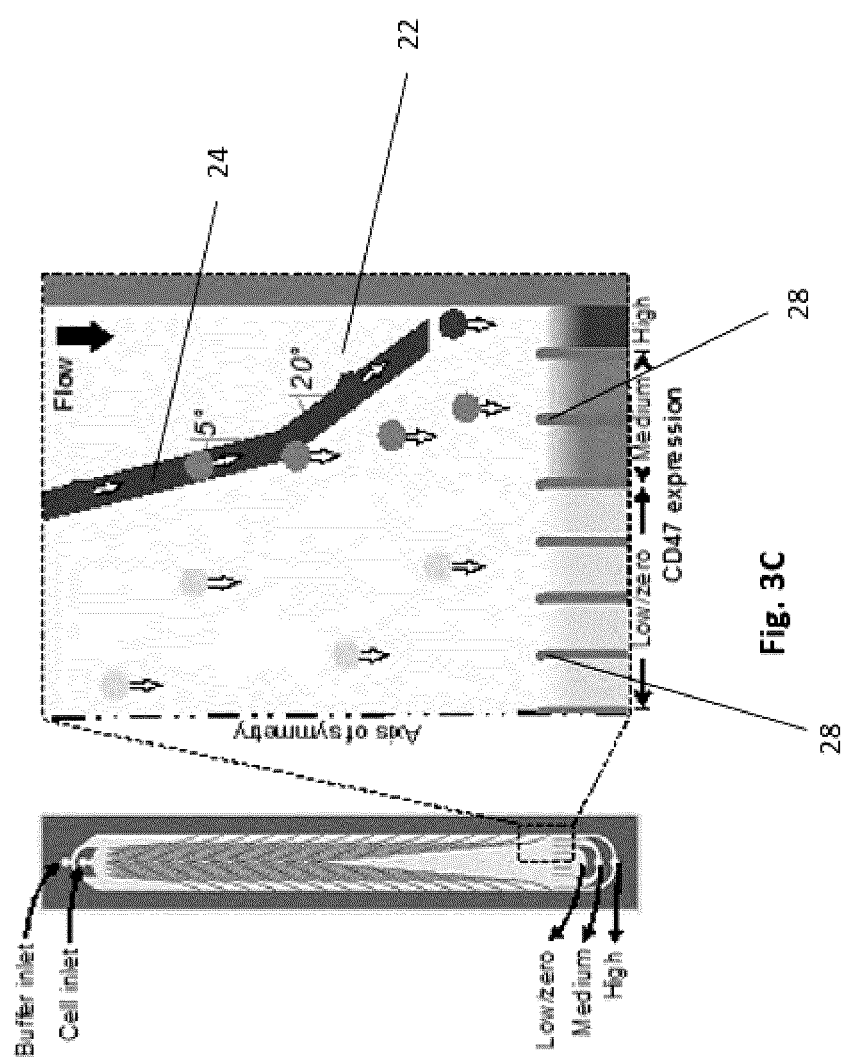
Figure 3D:
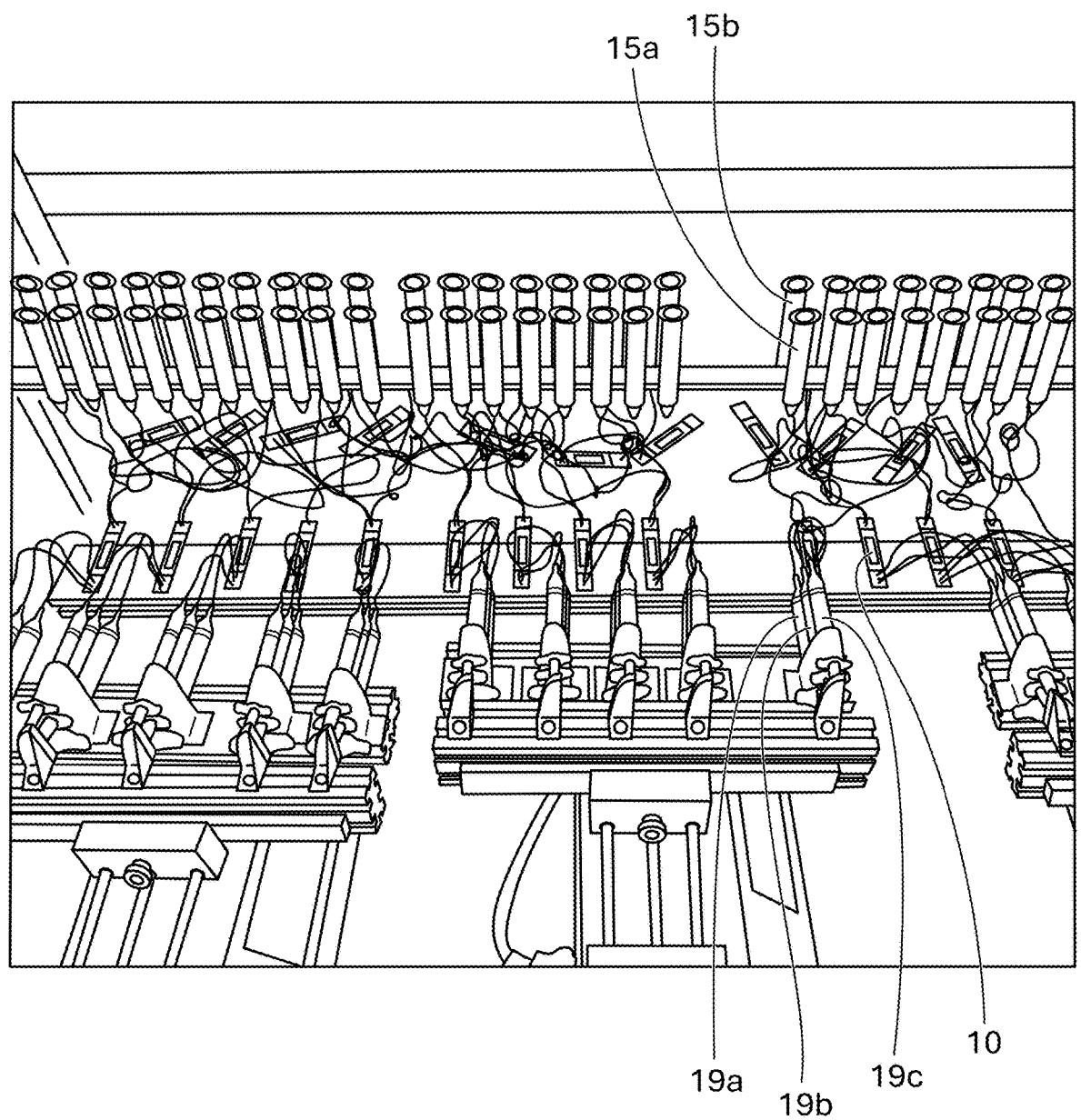
FIG. 3D shows multiple microfluidic chip devices that are run in parallel.

Referring now to FIG. 3D, there is shown a plurality microfluidic chip devices 10. The inlets of each microfluidic chip device 10 are connected to corresponding reservoirs 15a and 15b. The outlets of each microfluidic chip device 10 are connected to corresponding syringes 19a, 19b and 19c.

Referring back to FIG. 1, a magnet 20 can be positioned underneath the microfluidic chip device to generate a near-uniform magnetic field. For example, the magnet can be a neodymium magnet.

Referring to FIG. 2, there is shown a top-down view of the microfluidic chip device 10 of FIG. 1. The width of the microfluidic chip device can be about 5 mm to about 20 mm or any width including or between about 5 mm to about 20 mm. For example, the width of the microfluidic chip device can be about 12.5 mm. The length of the microfluidic chip device can be about 60 mm to about 100 mm or any length including or between about 60 mm to about 100 mm. For example, the length of the microfluidic chip device can be about 80 mm.

The microfluidic chip device includes a fluidic sorting channel. The microfluidic chip device includes a fluidic sorting channel 22. The fluidic sorting channel is fluidly connected to the buffer and sample inlets.

The width of the fluidic sorting channel can vary. For example, the width of the fluidic sorting channel in the microfluidic chip device can for example be about 2 mm to about 15 mm, optionally about 3 mm to about 10 mm or any width including or between about 2 mm and 15 mm. The height of the fluidic sorting channel can also vary. For example, in the microfluidic chip device the height of the fluidic sorting channel can be for example about 50 microns to about 300 microns or any width including or between about 50 microns and about 300 microns.

The base of or below the fluidic sorting channel includes a plurality of magnetic deflection guides 24. The deflection guides can include: Metglas™ 2714A; cobalt-based magnetic alloy; nickel-iron magnetic alloy (e.g. Permalloy), various iron alloys, etc. High magnetic permeability materials can be used, for example having a $\mu/\mu$ of about 80000. For example, the magnetic guides can generate local field amplifications in the presence of an external magnetic field. For example, magnetically labelled cells, subjected to magnetic and drag forces, can follow the deflection guides as long as the component of drag force acting perpendicular to the guides does not exceed the magnetic trapping force. The deflection guides extend along a length of the fluidic sorting channel.

Each deflection guide comprises a first segment having a first angle relative to the direction of flow and extending outwardly and a second segment having a second angle relative to the direction of flow and extending outwardly, wherein the first segment intersects the second segment. The first angle can be about 2 to about 20 degrees or any angle including or between about 2 and about 20 degrees. The first angle can be about 5 degrees. The second angle can be about 20 to about 90 degrees or any angle including or between about 20 and about 90 degrees, e.g. about 21 degrees. For example, the first angle and the second angle can have a difference of about 5 degrees. For example, the first angle and the second angle can have a difference of about 5 degrees to about 20 degrees or any angle including or between about 5 degrees and about 20 degrees.

The angles of each deflection guide of each set are about the same e.g. within 10% or within 5%. For example, the angles of each deflection guide can be substantially the same.

The deflection guides can include two sets of deflection guides. For example, each set can include about 4 to 30 guides. For example, each set can include 4 or at least 4 guides, 5 or at least 5 guides, 6 or at least 6 guides, 7 or at least 7 guides, 8 or at least 8 guides, 9 or at least 9 guides, 10 or at least 10 guides, 11 or at least 11 guides, 12 or at least 12 guides, 13 or at least 13 guides, 14 or at least 14 guides or 15 or at least 15 guides.

In one embodiment, the first set can be outwardly angled and directed to a first side or wall 26a of the fluidic sorting channel and the second set can be outwardly angled and directed to a second side or wall 26b of the fluidic sorting channel. The first and second sides are typically opposite.

In one embodiment, the pattern of the guides can be reversed such that they are angled inwards. For example, the first set can be inwardly angled and directed to a middle portion of the fluidic sorting channel. The second set can be inwardly angled and directed to the middle portion of the fluidic sorting channel. For example, the cells are pushed to the middle of the device, and not towards the outer walls.

The deflection guides can be encapsulated providing a smooth surface for the base of the sorting channel. In some embodiments, the encapsulated deflection guides are further treated to increase hydrophobicity.

In some embodiments, the microfluidic chip device can include a plurality of collection stations. Referring to FIG. 2 and FIG. 3C, collections stations 28 are located at the bottom end of the fluidic sorting channel.

For example, the collection stations can be high-level subpopulation collection stations, medium-level subpopulation collection stations and low-level subpopulation collection stations.

High-level subpopulation collection stations can be adjacent to the first and second sides of the fluidic sorting channel and fluidly connected to the first outlet, such that the high-level subpopulation collection stations can receive a first subpopulation expressing high levels of a target marker of interest.

Medium-level subpopulation collection stations can be adjacent to the high-level subpopulation collection stations and fluidly connected to the second outlet, such that the medium-level subpopulation collection stations can receive a second subpopulation expressing medium levels of a target marker of interest.

Low-level subpopulation collection stations can be positioned between the medium-level subpopulation collection stations and fluidly connected to the third outlet, such that the low-level subpopulation collection stations can receive a third subpopulation that is unlabeled or having low levels of the target marker of interest.

Each of the outlets 14a, 14b and 14c is configured to receive one subpopulation of the cell sample. For example, the outlet 14a can receive a first subpopulation of the sample; the outlet 14b can receive a second subpopulation of the sample; the outlet 14c can receive a third subpopulation of the sample. Each outlet includes collection bins for collecting the corresponding subpopulation.

As previously mentioned, the buffer inlet includes an opening 12b and bifurcated arms 13a and 13b that direct the buffer to the sides of the sample to focus the sample stream. As shown in FIG. 2, a width of each of the bifurcated arms 13a and 13b can correspond to the sum of the widths of the collection bin 15a for the first outlet and the collection bin 15b for the second outlet.

FIGS. 3A, 3B and 3C show a close-up view of a deflection guide 24 of FIG. 2. The deflection angle $\theta$ can be about 5° at the channel center about to 20° degrees at the outermost edge.

Referring to FIGS. 3A, 3B and 3C, $F_{Mag}$ refers to the magnetic force pulling the cell to the guide. $F_{Drag}$ refers to the total drag force. $F_{Drag\parallel}$ is the component of the total drag force parallel to the guide. $F_{Drag\perp}$ is the component of the drag force perpendicular to the guide. $F_{Net\perp}$ is the sum of the $F_{Mag}$ and $F_{Drag\perp}$. $F_{Net\perp}$ is equal to 0 when the cells are riding along the guide (see FIG. 3B). As the angle sharpens, $F_{Drag\perp}$ will be larger than $F_{Mag}$, $F_{Net\perp}$ is non-zero and the cell will fall off the guide (see FIG. 3C).

In another embodiment, a microfluidic parallelized device can include a platform having a plurality of magnetic deflection guides. For example the magnetic deflection guides can be serially positioned. For example, the magnetic deflection guides can be positioned in parallel on the platform.

For example, the deflection guides can be grouped into deflection units. The deflection units can be positioned in parallel on the platform. For example, there can be about 10 to about 40 deflection units positioned in parallel on the platform, or any number of deflection units including or between about 10 to about 40 deflection units.

Each deflection unit can include two sets of guides. Each set can include about 4 to about 15 guides or any number of guides including or between about 4 to about 15 guides.

For example, the first set of guides can be outwardly angled and directed to a first side of the platform and the second set of guides can be outwardly angled and directed to a second side of the platform.

The microfluidic parallelized device can include a manifold having at least one inlet port and two or more outlet ports, and a fluidic sorting channel definable by sealing the manifold on the platform.

The fluidic sorting channel can be fluidly connected to the inlet and outlet ports.

Each deflection unit can extend along a length (or width) of the fluidic sorting channel.

For example, as in the chip device, each deflection guide comprises a first segment having a first angle relative to the direction of flow and extending outwardly and a second segment having a second angle relative to the direction of flow and extending outwardly. The first segment can intersect the second segment. The magnetic deflection guides can be encapsulated with a photoresist material on the platform.

As shown in FIG. 4, a plurality of deflection units 51 are positioned in parallel on the platform 42. Each deflection unit can include two sets of deflection guides. As shown in FIG. 4, each set includes 4 guides. Each set can include 4 to 30 deflection guides. The first set of guides is outwardly angled and directed to a first side of the platform and the second set of guides is also outwardly angled and directed to a second side of the platform.

The magnetic guides can be encapsulated in any coating that can provide a smooth surface that does not interfere with the electrical/magnetic properties of the magnetic guides and which is biologically non-toxic to cells flowing thereon. Non-limiting examples include stable photoresists, resins, polymers, glass.

The manifold can include an inlet channel fluidly connectable to the inlet port and the fluidic sorting channel. The inlet channel can split a sample or buffer received at the inlet port into a plurality of streams. Each stream can directed to the fluidic sorting channel. The manifold can include an outlet channel fluidly connectable to the two or more outlet ports and the fluidic sorting channel. The outlet channel can route each of subpopulations received at the fluidic sorting channel to a corresponding outlet port.

An O-ring can be used to seal the manifold to the platform. The inlet channel and the outlet channel can have square cross-sections. The inlet channel and the outlet channel can include a tree structure to reduce fluidic imbalances (e.g. to balance flow).

Referring to FIGS. 4, 5A, 5B and 6, there is shown a microfluidic parallelized device 40. The microfluidic parallelized device 40 includes a platform 42 having sides 44a, 44b, 44c and 44d. The parallelized device includes a plurality of "microfluidic chip" functional units, each comprising for example a sample inlet and a buffer inlet as well as two or more, for example 3, outlets, and configured to be aligned with a deflection unit of magnetic guides in the platform. The platform can also include a glass base on which magnetic guides are added.

As shown on FIG. 4, the platform 42 defines the base of the fluidic sorting channel 50. The platform 42 includes a base on which magnetic guides 51 are added.

The width of the platform along the x-axis can be about 40 mm to about 80 mm or any width including or between about 40 mm to about 80 mm. For example, the width of the platform can be about 61.8 mm. The length of the platform can be about 15 mm to about 45 mm or any length including or between about 15 mm to about 43 mm. For example, the length of the platform can be about 30.4 mm.

As shown in FIG. 4, a plurality of deflection units 51 are positioned in parallel on the platform 42. Each deflection unit can include two sets of guides. As shown in FIG. 4, each set includes 4 guides. The first set of guides is outwardly angled and directed to a first side of the platform and the second set of guides is also outwardly angled and directed to a second side of the platform.

The parallelized device can include a plurality of collection stations 58. The collection stations can be for example high-level subpopulation collection stations, medium-level subpopulation collection stations and low-level subpopulation collection stations. The high-level subpopulation collection stations can receive a first subpopulation with a high level of a target marker of interest. The medium-level subpopulation collection stations can receive a second subpopulation expressing medium levels of a target marker of interest. The low-level subpopulation collection stations can receive a third subpopulation expressing low levels of a target marker.

For example, the microfluidic parallelized device 40 can follow the same operating principles as the microfluidic chip device described in FIG. 1. For example, the deflection units comprise magnetic guides angled at 5° and 20° which induce deflection in magnetically labelled cells flowing in a central stream, with unlabeled cells unaffected by an applied magnetic field. Sorted cells are collected in the at least two, optionally three outlets flowing into for example collection stations 58. Each collection station is connected to a corresponding outlet.

Contrary to the microfluidic chip device described in FIG. 1, the microfluidic parallelized device 40 can deflect cells flowing in any one of the sample streams resulting from the plurality of sample inlets (e.g. 24 sample streams), all flowing in parallel, giving the microfluidic parallelized device 40 the potential for much higher throughput (for example, over 200 million cells per hour). For example, the microfluidic chip device described in FIG. 1 can have a throughput of 30 million cells per hour. Multiple chip devices can also be run in parallel to sort cells.

The microfluidic parallelized device can include an O-ring 62 for sealing the manifold to the platform 42. FIGS. 5A, 5B and 7 shows the manifold 60. FIG. 7 shows a top view of the manifold 60. For example, the O-ring can be a Viton™ O-ring. The O-ring provides seal so that fluid does not leak. As shown on FIG. 7, the platform can include a channel 65 for receiving the O-ring.

Stereolithographic 3D printing can be used to build the manifold. For example, as shown in FIG. 8, the 3D printed manifold can allow for the equivalent of 24 microfluidic functional chip devices to be run in parallel using one device and with significant ease-of-use.

For example, stereolithographic 3D printing enables three-dimensional channels to be printed in a matter of hours, with minimal active time required from an operator. All of the fluidic components, including inlets and outlets, inlet and outlet ports, inlet and outlet channels etc. can be printed as a single resin cartridge. The magnetic guides, which can be patterned via wet etching, can be patterned onto the platform. The platform can include a glass wafer. The manifold and the platform can then be clamped together and sealed using an O-ring.

Having the ability to separate the manifold and the platform can be advantageous. Separate manifold and platform components make it easier to sterilize, dry and store the components after use, allowing them to be reused. Second, having access to the inside of the platform opens up the possibility for more complex surface coatings to be applied to the fluidic sorting channel and/or the magnetic guides. This permits to reduce cellular friction and adhesion, which would lead to better performance and even higher throughput.

For example, a method for manufacturing the platform includes adding or fastening a plurality of magnetic deflection guides to a wafer (e.g. a glass wafer) such that each deflection guide includes a first segment having a first angle and extending outwardly and a second segment having a second angle and extending outwardly, such that first segment intersects the second segment. The deflection guides can be encapsulated, for example with a photoresist, resin, polymer or glass. For example, the photoresist can be SU-8. The guides can be encapsulated to improve sample flow.

For example, the first angle can be about 2 to about 20 degrees. The first angle can be about 5 degrees. The second angle can be about 20 to about 90 degrees. The deflection guides can include two sets. For example, each set can include about 4 to about 30 guides. For example, each set can include 15 guides. For example, the first set can be outwardly angled and directed to a first side of the wafer and the second set can be outwardly angled and directed to a second side of the wafer. The first and second sides can be opposite to each other One or more further surface coatings can be applied to the platform which forms the base of the fluidic sorting channel. For example, the encapsulated magnetic guides can be treated with pluronic prior to use or treated with a hydrophobicity agent such as fluorosilane to produce a hydrophobic surface to reduce cell friction. Treatment with a hydrophobicity agent can eliminate the need to degas the microfluidic parallelized device prior to use.

FIGS. 5A, 5B and 7 shows the manifold 60. FIG. 7 shows a top view of the manifold 60. The manifold includes inlet ports 64a and 64b, which are fluidly connected to the plurality of inlets of the microfluidic parallelized device 40. The inlet ports 64a and 64b can be positioned at a top portion of the manifold 60.

The manifold also includes at least two outlet ports, optionally outlet ports 66a, 66b and 66c, which are fluidly connected to the outlets 52a, 52b and 52c of the microfluidic parallelized device 40. For example, the outlet port 66a is fluidly connected to the outlet 52a; the outlet port 66b is fluidly connected to the outlet 52b; and the outlet port 66c is fluidly connected to the outlet 52c.

Referring back to FIG. 4, the microfluidic parallelized device 40 includes a plurality of inlets 48a and 48b. The inlets 48a and 48b can be positioned at a bottom portion of the manifold 60, such that when the manifold is sealed on the platform, the inlets are positioned on top of the platform to direct a sample and/or buffer on the fluidic sorting channel.

For example, when the manifold is sealed on the platform, the inlets 48a and 48b are fluidly connected to the fluidic sorting channel.

The microfluidic parallelized device 40 also includes a plurality of outlets 52a, 52b and 52c.

The outlets 52a, 52b and 52c can be positioned at a bottom portion of the manifold 60, such that when the manifold is sealed on the platform, the outlets are positioned on top of the platform. The outlets 52a, 52b and 52c can be fluidly connected to the fluidic sorting channel and/or collection stations when the manifold is sealed on the platform.

The fluidic channel can include a plurality of collection stations. For example, the collection stations can be high-level subpopulation collection stations, medium-level subpopulation collection stations and/or low-level subpopulation collection stations. High-level subpopulation collection stations can be fluidly connected to the fluidic sorting channel and fluidly connected to a first outlet (e.g. outlet 52a), such that the high-level subpopulation collection stations can receive a first subpopulation expressing high levels of a target biomarker of interest of the sample.

Medium-level subpopulation collection stations can be adjacent to the high-level subpopulation collection stations and fluidly connected to a second outlet (e.g. outlet 52b), such that the medium-level subpopulation collection stations can receive a second subpopulation expressing medium levels of a target biomarker of interest of the sample.

Low-level subpopulation collection stations can be positioned between the medium-level subpopulation collection stations and fluidly connected to a third outlet (e.g. outlet 52c), such that the low-level subpopulation outlet collection stations can receive a third subpopulation that is unlabeled or having low levels of the target marker of interest.

The outlet 52a can receive a first subpopulation of the sample from corresponding high-level subpopulation collection stations; the outlet 52b can receive a second subpopulation of the sample from corresponding medium-level subpopulation collection stations; the outlet 52c can receive a third subpopulation of the sample from corresponding low-level subpopulation collection stations.

Referring to FIG. 4, the manifold includes 24 sample inlets 48a and 24 buffer inlets 48b. The manifold also includes 24 sets of outlets 52a, 52b and 52c. The platform includes 24 deflections units. When the manifold is sealed on the platform, each corresponding sample inlet 48a and buffer inlet 48b is positioned at a top portion of a corresponding deflection unit 51. Each corresponding buffer inlet can include bifurcated arms that direct the buffer to the sides of the sample to focus the sample stream over a corresponding deflection unit. In the same way, each corresponding set of outlets 52a, 52b and 52c is positioned at a lower portion of the deflection unit, such that each outlet can collect one of subpopulations expressing high/medium/low levels of a target biomarker of interest of the sample. For example, each outlet can include collection bins for collecting the corresponding subpopulation of the sample. For example, the width of each of the bifurcated arms of the buffer inlet can correspond to the sum of the widths of the collection bins for a first and second outlet.

Referring now to FIG. 8, there is shown a front view of the manifold 60. The manifold 60 includes an inlet channel 68, which includes a tree structure comprising of sub-channels to reduce fluidic resistance and balance flow. The tree structure of the sub-channels 70a, 70b and 70c of manifold 60 is configured to reduce force on cells and balance flow. The inlet channel can include a plurality of pathways.

Branches are preferably bifurcated where possible to balance buffer and sample flow. Where trifurcation is used, flow can be balanced for example by increasing the length of a sub-channel, such as a middle sub-channel.

As shown in FIG. 8, the inlet channel 68 branches into three pathways 68a, 68b and 68c. Each one of the pathways can extend from the inlet ports 64a and 64b and branch into sub-channels 70a, 70b and 70c having a tree structure. The sub-channels 70a, 70b and 70c can be angled, for example to facilitate liquid resin draining during printing. Other tree structures can be used depending on the number of inlets of the microfluidic parallelized device.

As shown in FIG. 8, the middle pathway 68b can be lengthened compared to the side pathways 68a and 68c to balance fluidic resistance.

Referring to FIG. 9, there is shown a side view of the bottom of the manifold 60. The manifold includes a plurality of inlets 48a and 48b. When the manifold is sealed on top of the platform, the inlets 48a and 48b are positioned on top of the platform to direct a sample and/or buffer on the fluidic sorting channel. Each of the inlets 48a can be fluidly connected to inlet port 64a to direct a sample received at the inlet port 64a on the fluidic sorting channel of the microfluidic parallelized device. Each of the inlets 48b can be fluidly connected to inlet port 64b to direct a buffer received at the inlet port 64b on the fluidic sorting channel of the microfluidic parallelized device.

For example, the branched structures for the inlets (48a and 48b) and outlets (52a, 52b and 52c) can be angled so that the channels do not overlap as diameter increases.

The width and height of the fluidic channel and deflection guide angles can be modified to achieve different percent distributions of the cell subpopulations.

The microfluidic chip device or the microfluidic parallelized device as described in the present document can be used for identification of modifiers of target marker levels. They can also be used for sensing and deflecting cells labeled based on their loading with antibody-labeled nanoparticles as further described herein.

In an embodiment, the microfluidic device comprises one or more features described in the Examples or drawings.

Figure 10A:
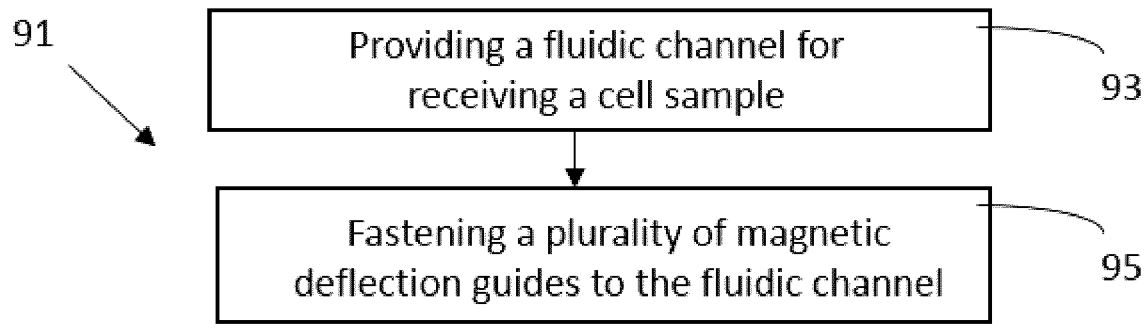
FIGS. 10A and B show examples of methods for manufacturing a microfluidic chip device.

Referring to FIG. 10A, there is shown a method 91 for manufacturing a microfluidic chip device according to one example. At 93, a fluidic channel is provided for receiving a cell sample. For example, the fluidic channel can include an enclosed chamber having one or more inlets and one or more outlets. The inlets can be used to feed a cell sample to the fluidic chamber. Subpopulations of the cell sample can be collected at the outlets.

At 95, a plurality of magnetic deflection guides are added or fastened to the fluidic channel. For example, adhesive bonding can be used to fasten the deflection guides to the fluidic channel. Each deflection guide can include a first segment having a first angle and extending outwardly and second a segment having a second angle and extending outwardly, such that first segment intersects the second segment.

The method can include encapsulating the deflection guides. For example, the deflection guides are encapsulated with a photoresist. For example, the photoresist can be a type of SU-8 photoresist.

The method can include patterning the features (e.g. the walls, sides, etc.) of the fluidic sorting channel. For example, the method can include patterning the sides and/or bottoms of the fluidic sorting channel.

The method can include fastening a (polydimethylsiloxane) PDSM layer on top of the fluidic sorting channel.

For example, the PDSM layer can be bonded on top of the fluidic sorting to define a chamber. The method can include punching holes on the PDSM layer to define inlets and outlets of the microfluidic chip device.

For example, the first angle can be about 2 to about 20 degrees. The first angle can be about 5 degrees. The second angle can be about 20 to about 90 degrees. The deflection guides can include two sets. For example, each set can include about 4 to about 30 guides. For example, each set can include 15 guides. For example, the first set can be outwardly angled and directed to a first side of the wafer and the second set can be outwardly angled and directed to a second side of the wafer. The first and second sides can be opposite to each other.

The magnetic material can include can include: Metglas™ 2714A; a cobalt-based magnetic alloy; a nickel-iron magnetic alloy (e.g. Permalloy); and various iron alloys, etc. High magnetic permeability materials can be used, for example having a $\mu/\mu$ of about 80000. The fluidic channel can be patterned on a wafer comprising the magnetic guides.

Figure 10B:
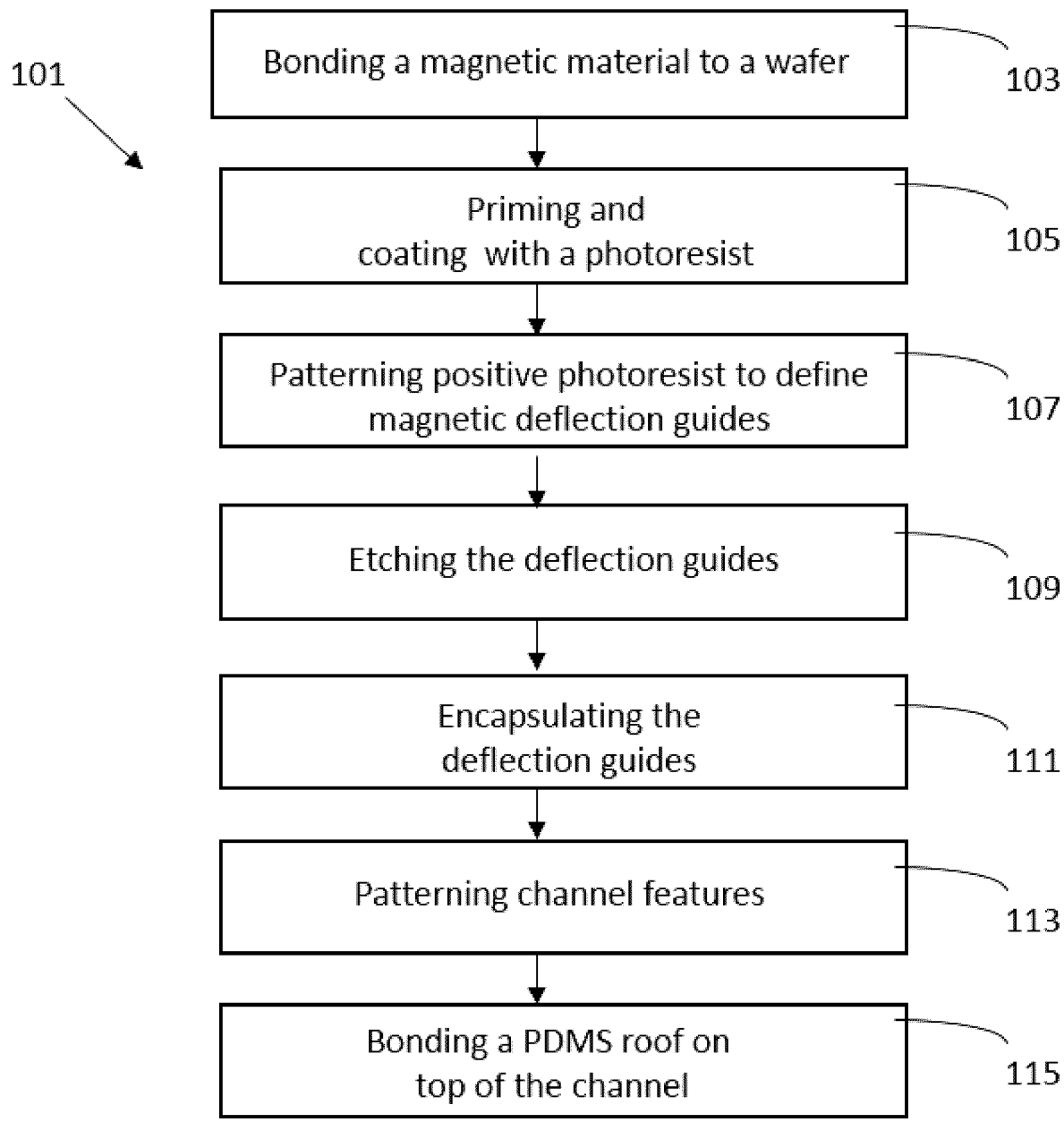

FIG. 10B shows a method 101 for manufacturing the microfluidic chip device, according to one example. At 103, a magnetic material (such as Metglas 2714A foil) is bonded to a wafer (such as a glass wafer). At 105, the magnetic material is primed and spin coated with a photoresist. For example, the magnetic material can be primed with MCC 80/20 and spin coated with a S1811 photoresist.

At 107, the magnetic material is patterned to define the magnetic deflection guides. For example, the deflection guides can be patterned to include a first segment having a first angle and extending outwardly and second a segment having a second angle and extending outwardly, such that first segment intersects the second segment. For example, the first angle can be about 2 to about 20 degrees. The first angle can be about 5 degrees. The second angle can be about 20 to about 90 degrees. The deflection guides can include two sets. For example, each set can include about 4 to about 30 guides.

At 109, the guides are etched. At 111, the guides are encapsulated. For example, the guides can be encapsulated with SU-8. At 113, the channel features (e.g. side walls) are patterned. At 115, a roof (e.g. a PDMS layer, etc.) is bonded on top of the channel. For example, holes can be punched on the PDSM layer to define inlets and outlets of the microfluidic chip device.

In an embodiment, the method of manufacturing comprises one or more of the steps described in Examples 2, 3 or 5.

III. Methods and Immunoassays

Methods of Making

Another aspect of the disclosure provides a method for separating or sorting a magnetically labelled cell sample into subpopulations based on levels of a target marker, the method comprising:

introducing the magnetically labelled cell sample and a buffer in to at least one inlet or inlet port of a microfluidic device, the inlet and/or inlet port configured to provide separate substantially parallel streams of the magnetically labelled cell sample and the buffer, the microfluidic device comprising i) a fluidic sorting channel, the fluidic sorting channel in communication with a plurality of magnetic deflection guides wherein the deflection guides extend along a length of the fluidic sorting channel, wherein each deflection guide comprises a first segment having a first angle relative to the direction of flow and extending outwardly and a second segment having a second angle relative to the direction of flow and extending outwardly, and wherein the first segment intersects the second segment, and ii) a magnet positioned underneath the fluidic sorting channel to generate a magnetic field;

flowing the magnetically labelled cell sample through the fluidic sorting channel;

collecting two or more, preferably three, subpopulations from two or more outlets or outlet ports coupled to the fluidic sorting channel, each one of the outlets or outlet ports being configured to receive a subpopulation of the magnetically labelled cell sample.

The method can be used to sort genome-wide functional genetic screens as well as other applications requiring the sorting of large numbers of target cells based the level of macromolecule such as a protein or nucleic acid. For example, target cells are cells that have been modified in a screen to have an altered level of a target marker. In CRISPR screens in particular there are a large number of target cells that would be of interest to separate, collect and sequence, for example at least or greater than 2,500, 5,000, 10,000, 20,000, 50,000 or 100,000 target cells among the magnetically labelled cell sample, for example $10^6$, $10^7$, $10^8$, $10^9$ or more cells in combination are the cells of the magnetically labelled cell sample. Methods for separating and isolating such cells are described herein.

As demonstrated herein, each one of the outlets is configured to receive a subpopulation based on magnetic loading of the magnetically labelled cells. The magnetically labelled cell sample comprises a heterogeneous cell sample (e.g. a plurality of cells having a target marker at variable levels) and magnetic affinity particles with affinity for the target marker directly or indirectly. Cells with a high level of target marker have an increased magnetic load compared to cells with a medium or low level of target marker. Depending on the particular use, cells with a higher level of target marker (high subpopulation) than a starting population (e.g. prior to screening and/or relative to the magnetically labelled cell sample), and/or cells with a lower level of target marker (low subpopulation) than a starting population may be the target cells.

In an embodiment, the magnetic affinity particles comprise magnetic particles (such as magnetic beads), optionally magnetic microparticles or nanoparticles, and a binding agent such as antibody, aptamer, nucleic acid probe or ligand that has affinity for and selectively binds the target marker, or magnetic particles and a secondary binding agent that can indirectly bind the target marker via a binding agent (e.g. antibody, aptamer, nucleic acid probe or ligand) that has affinity for and selectively binds the target marker. For example, streptavidin microbeads or anti-biotin microbeads can be used to label cells wherein the target marker is bound by a binding agent such as an antibody or nucleic acid probe having a biotin label. Similarly anti-fluorochrome microbeads such as anti-FITC, anti-PE or anti-APC microbeads can be used to label cells wherein the target marker is bound by a binding agent such as an antibody or nucleic acid probe having a fluorochrome label and anti-immunoglobuin microbeads can be used to label cells wherein the target marker is bound by an immunoglobulin. Any magnetic affinity particles or magnetic particles useful for immunomagnetic separation can be used. For example MACS microbeads or nanobeads can be used. In one embodiment, the nanoparticles have an average diameter of about or less than 200 microns or an average diameter of about or less than 100 microns.

The target marker can be any molecule accessible to binding by a binding agent. In an embodiment, the target marker is a cell surface or transmembrane macromolecule, such as a cell surface protein (e.g. CD47). In another embodiment, the target marker is an intracellular macromolecule such as an intracellular protein, DNA or RNA.

Where the target marker comprises an extracellular portion, e.g. is a cell surface or transmembrane protein, the heterogeneous cell sample can be magnetically labelled by incubating the heterogeneous cell sample with a binding agent that is directly conjugated to magnetic particles or by incubating with a binding agent that can be bound by a secondary agent conjugated to the magnetic particles, for example, a biotinylated anti-target marker antibody or ligand and subsequently incubating with anti-biotin magnetic beads. If the target marker is an intracellular macromolecule, such as an intracellular protein, the cells are permeabilized prior to incubation the biotinylated anti-target marker binding agent antibody or ligand and subsequent incubation with the anti-biotin magnetic beads.

In the case of a proteinaceous target marker (including post-translational modification target marker), the binding agent can be an antibody or an aptamer that specifically binds the target marker. In the case of a nucleic acid, the binding agent can be a nucleic acid probe that hybridizes the nucleic acid under moderate or high hybridization conditions. The probe can be a magnetically labelled nucleic acid probe or comprise biotin or a fluorochrome for indirect binding and the labelling comprises a permeabilization step.

Cell can be fixed and/or permeabilized. For example, cells can be fixed in paraformaldehyde, optionally 4% v/v PFA/PBS and cells can be permeabilized by incubating the heterogeneous cell sample with a permeabilization agent such as a detergent, optionally, 0.5% Triton-X-100/PBS.

The heterogeneous cell sample can be any cell sample wherein the cells comprise variable levels of the target marker. The heterogeneous cell sample can comprise stem cells (e.g. hESCs), be a biological sample or environmental sample comprising cells, or a cell line for example subjected to a genetic screen. For example, any cell line capable of being genetically edited can be used. Biological samples such as blood including whole blood or fractions thereof, urine, saliva and stool preparations that comprise a large number of target cells to be phenotypically separated can also be processed. Such samples can be prepared by diluting with a buffer. The microfluidic devices described herein can be used for example to separate subpopulations of white blood cells into different phenotypic populations. The target marker can be any macromolecule that varies, for example a target marker that is present or not, or that is present at a low level or a high level, or that is present at a low, medium or high level in the cell sample to be separated. The target marker can be for example CD15 and CD45, CD4 or CD8.

Any binding agent that specifically binds a target marker can be used. The target marker can be a protein, or a region thereof, defined for example by the specificity of a binding agent such as an epitope, or other macromolecule such as a nucleic acid. The binding agent can be an antibody such as antibody, optionally a monoclonal antibody or a polyclonal antibody or a binding fragment of any thereof, a ligand, aptamer or a nucleic acid probe. The binding agent can also be a binding partner that binds a target marker. For example soluble SIRPα that is labelled directly or indirectly can be used when the target marker is the SIRPα binding region of CD47.

As demonstrated in the Examples, in addition to the methods being useful for detecting genetic modifiers of target marker expression levels (e.g. molecules that increase or decrease expression), the methods can be used to detect genetic modifiers that affect post-translational modifications. As shown in the Examples, the target marker can be a region of a cell surface protein that is involved in binding, such as the region of CD47 that interacts with SIRPα.

In a tumor microenvironment CD47 expression can be high which via the SIRPα pathway suppresses phagocytosis, disabling the immune system ability to fight the tumor.

Accordingly the target marker can be the region on CD47 that interacts with SIRPα in combination with the binding agent CC2C6 (available from BioLegend) or other binding agent that interacts with said region, such as soluble SIRPα, or epitope and the screen is for identifying genetic regulators that impact CD47 levels and/or obscure or enhance the presence of the region/epitope bound by SIRPα and/or CC2C6 and/or identifying putative druggable targets using the devices and methods described herein.

The binding agent is selected according to the desired screen. For example, as shown in the Examples, an antibody that binds a region comprising a protein binding site can identify genetic interactors that decrease or destroy, or increase or improve, the presence of the binding site. Other antibodies specific for an epitope that is not involved in protein interaction, can identify genetic interactors that increase or decrease the level of the target marker.

In an embodiment, the magnetically labelled cell sample introduced into the at least one inlet is at a concentration of about $0.5 \times 10^6$ cells/ml to about $1 \times 10^7$ cells/ml, optionally $1 \times 10^6$ cells/ml to about $5 \times 10^6$ cells/ml or any cell concentration between $0.5 \times 10^6$ cells/ml to about $1 \times 10^7$ cells/ml.

In an embodiment, the magnetically labelled cell sample comprises about, at least or greater than 2,500, 5,000, 10,000, 20,000, 50,000 or 100,000 target cells.

The buffer can be used to provide the buffer stream which focuses the sample stream but also to resuspend or dilute cell samples. The buffer can be any cell non-toxic preferably aqueous buffer such as Hanks' Balanced Salt Solution or phosphate buffered saline (PBS), optionally comprising serum. Cell media can also be used as buffer and/or to resuspend the cells of the cell samples. For example, cells have been sorted in media such as DMEM, MEM and RPMI, and PBS. The buffer is for example non-toxic over the time scale of the screen and has substantially the same viscosity as the cell sample. For more viscous cell samples, sodium alginate can be added to the buffer to balance the viscosity.

The sample can be flowed through the fluidic channel using for example using a pump such as a syringe pump operating in withdrawal mode (when connected to the outlets) or push mode (connected to the inlets) driving in the case of syringe pumps, two or more syringes fluidly connected to the two or more outlets or outlet ports or two or more inlets or inlet ports respectively. The two or more outlets or outlet ports, can be three outlets or outlet ports. The two or more inlets or inlet ports can be three inlets or inlet ports. Each outlet can be connected to a collection container, optionally a syringe with a preselected cross sectional area. For example, the cross-sectional area of syringe is selected to produce a flow rate corresponding to the width of the collection stations or opening flowing to each outlet when the syringe is operated by a syringe pump in withdrawal mode.

In some embodiments, other types of pumps (e.g. infusion pumps, rotary pumps, piston pumps, diaphragm pump, gear pumps, etc.) are used.

For example, typically three outlets or outlet ports, a first, second and third outlet or outlet port will be used to collect subpopulations comprising a high, medium or low level of the target marker. In one embodiment, 20 ml, 10 ml and 3 ml syringes are used, or multiple sets thereof. The syringes can be driven by the same pump.

The magnet is placed directly below the sorting channel, optionally abutting the bottom surface of a wafer supporting the magnetic guides, or within 1 cm thereof.

In an embodiment, the magnetically labelled sample is introduced into at least one inlet or inlet port, preferably a sample inlet or sample inlet port and a buffer inlet or buffer inlet port, using a sample inlet reservoir and a buffer inlet reservoir, containing the magnetically labelled cell sample and the buffer respectively. In embodiments comprising a sample inlet or sample inlet port and a buffer inlet or buffer inlet port, the sample inlet reservoir is fluidly connected to the sample inlet or sample inlet port and the buffer inlet reservoir is fluidly connected to the buffer inlet or buffer inlet port.

Figure 15A:
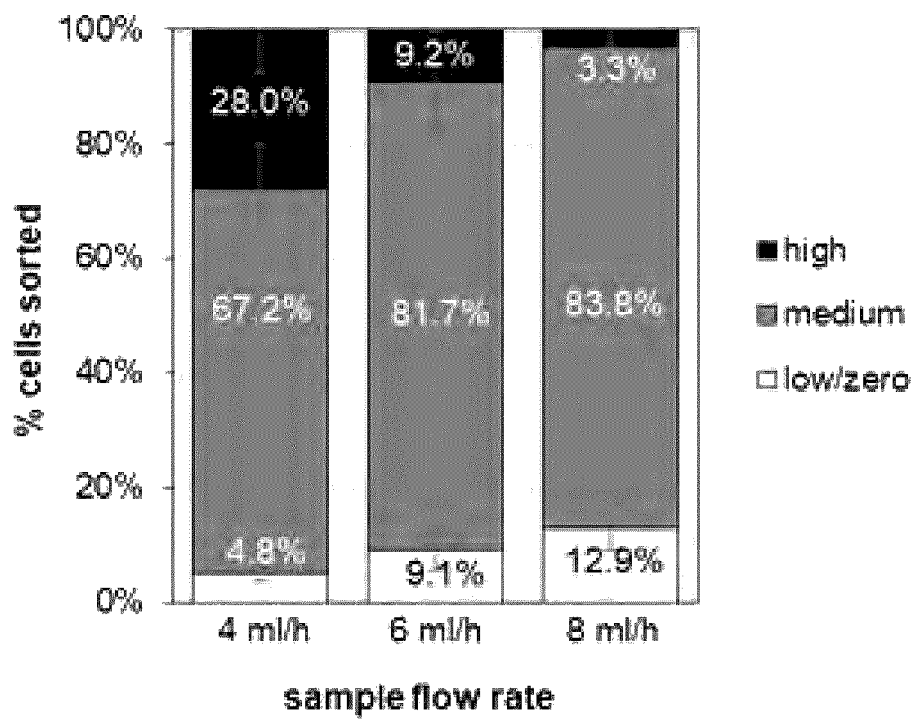
FIG. 15A. is a graph illustrating the results of flow rate optimization to achieve 10/80/10% distribution into low/zero, medium and high outlets. HAP1 cells were labelled with magnetic beads targeted to CD47. Data represent the mean f SD of n=3 biological replicates.

In an embodiment, the magnetically labelled cell sample is flowed in the channel at a rate of 2 ml/hr to 30 ml/hr, optionally about 4 ml/hr, or about 6 ml/hr or about 8 ml/hr or about 10 ml/hr. Increasing the flow rate increases the drag forces on the cells and shifts the gating on the subpopulations to a higher level of target marker. As shown in FIG. 15A, increasing the flow rate from 4 ml/hr to 8 ml/hr decreased the mean % cells sorted into the "high" outlet from about 28% to about 3%. The flow rate can be modified according to the desired sorting and/or level of target marker. For example, as shown in FIGS. 17D and G different flow rates can be used with target markers that are present at a lower level (e.g. density) than CD47 such as EpCAM or that are intracellular like vimentin.

In an embodiment, the flow rate of the cell sample and the buffer is substantially the same. The flow rate can be varied. For example, for screens where identifying cells where the modification or treatment desirably increases the level of target marker, a higher flow rate (e.g. sample flow rate of about 6-30 ml/hr can be used promoting distribution of cells with unaltered levels to a low outlet. Similarly a slower flow rate can be used (e.g. sample flow rate of about 2-8 ml/hr) when the aim is to identify cells where the modification or treatment decreases the level of the target maker.

For example, depending on the flow rate selected, a microfluidic device comprising two sets of 15 deflection guides having a first portion angled at about 5° and a second portion angled at about 20° relative to the direction of flow can achieve an approximate 10/80/10% distribution of subpopulations in the high, medium and low outlets or outlet ports.

Such a distribution can minimize for example the number of non-target cells (e.g. increasing signal to noise ratio) and facilitating identification of modifiers.

The microfluidic device can be any device for example a device described herein such as a microfluidic chip device or a microfluidic parallelized device. In a preferred embodiment, the at least one inlet or inlet port is two inlets or inlet ports, a sample inlet or sample inlet port and a buffer inlet or buffer inlet port.

The methods and devices described herein are useful for sorting genome scale functional genetic screens involving large number of cells. As demonstrated in the Examples, the single microfluidic chip device can achieve a sorting capacity of about $3 \times 10^7$ cells/hr. In one embodiment, a plurality of fluidic devices are run in parallel, for example 2-50, or any number between and including 2 and 50 (see for example FIG. 3D). For example, an arrayed set up using 30 parallel microfluidic chip devices were used as described in the Examples achieving a sorting capacity of close to 1 billion cells per hour. In another embodiment, a microfluidic parallelized device is used.

In one embodiment, the method and/or microfluidic device is for sorting at least $1\times10^7$, $5\times10^7$, $1\times10^8$ or $5\times10^8$ cells. In another embodiment, the method and/or microfluidic device is for sorting at least $1\times10^7$ cells/hr, $5\times10^7$ cells/hr, $1\times10^8$ cells/hr, or $5\times10^8$ cells/hr. As further demonstrated in the Examples, the methods maintain high levels of cell viability (for example greater than 90% or 95%).

At least one of the subpopulations can be collected from at least one of the two or more outlets or outlet ports coupled to the fluidic channel, for example in the respective syringes fluidly connected to the two or more outlets or outlet ports. Other outlet receptacles can also be used. The outlet receptacles are preferably sterile.

The ratio of the buffer to the sample can be from about 10:1 to about 0.1:1, preferably about 2:1 or about 1:1 or any ratio therein (for example in 0.1 increments). For example where the sample flow rate is about 6 ml/hr, the buffer flow rate can also be about 6 ml/hr providing for a total flow rate of about 12 ml/hr.

A ratio of buffer to sample that is greater than for example 2:1 can be used in some embodiments.

A ratio of buffer to sample that less than for example 0.5:1 or about 0.1:1 ratio, buffer may be used in some embodiments.

In embodiments wherein the microfluidic device comprises three outlets or outlet ports, collection of three subpopulations is possible, a bulk subpopulation comprising a baseline level of the target marker, a subpopulation comprising a higher level of the target marker and a subpopulation comprising a lower level of the target marker and/or unlabeled cells. Magnetically labelled cells subjected to magnetic and drag forces, will follow the guides as long as the component of drag force acting perpendicular to the guides does not exceed the magnetic trapping force (see FIGS. 3A and B). The outlets can be referred to as a first, second etc outlet. In embodiments comprising three outlets, cells with greater magnetic load representing the level of target marker, will be deflected to a first outlet e.g. the first outlet that can be referred to as the high level subpopulation outlet, optionally via high-level subpopulation collection stations. Cells with an intermediate or medium level of magnetic load, will be deflected to a second outlet that can be referred to as the medium level subpopulation outlet, optionally via medium-level subpopulation collection stations and cells with a low level or no magnetic load will be deflected to a third outlet that can be referred to as the low level subpopulation outlet, optionally via low-level subpopulation collection stations.

The subpopulations are optionally cultured or subjected to one or more biological assays.

Sorting using said methods and devices can be performed for example post selection, and after magnetically labelling the heterogeneous cell sample for the target marker, for example as described in the Examples.

In another embodiment, one or more of the subpopulation, optionally low, medium and/or high outlet or outlet port cells are subjected to a further sorting. As viability of the cells is maintained, the cells can be allowed to recover and expanded prior to for example further sorting or assay. In an embodiment, the method further comprises, obtaining or isolating a subpopulation that has been sorted, optionally culturing and propagating the subpopulation and resorting (e.g. a secondary sort) the cells according to a method and/or using a device described herein. In an embodiment, at least 2 sorts are performed. In another embodiment, at least 3 sorts are performed. As viability is maintained, multiple resorts can be performed. Resorting can facilitate the isolation of rare target populations.

The devices and methods are particularly suitable for large screens such as large scale random mutagenesis, RNAi screens, and genome editing methods such as Zinc-finger nuclease, TALEN or CRISPR screens, which typically comprise a large number of cells to be sorted. The devices and methods can be used for any screen comprising a large number of target cells wherein the target marker level varies.

The methods described herein can be used for sorting heterogeneous cells comprising a target marker, optionally genome edited screen cells. The sorting can be used to identify putative genetic regulators (e.g. genes that impact the level of a target marker of interest).

Accordingly another aspect of the disclosure provides a method for identifying a putative genetic regulator of a target marker, the method comprising:

obtaining a heterogeneous cell sample, optionally of genetically edited cells;

labelling the heterogeneous cell sample with a magnetic label that labels the target maker to provide a magnetically labelled cell sample;

introducing the magnetically labelled cell sample and a buffer in to at least one inlet or inlet port of a microfluidic device, the inlet and/or inlet port configured to provide separate substantially parallel streams of the magnetically labelled cell sample and the buffer, the microfluidic device comprising i) a fluidic sorting channel, the fluidic sorting channel in communication with a plurality of magnetic deflection guides wherein the deflection guides extend along a length of the fluidic sorting channel, wherein each deflection guide comprises a first segment having a first angle relative to the direction of flow and extending outwardly and a segment having a second angle relative to the direction of flow and extending outwardly, and wherein the first segment intersects the second segment, and ii) a magnet positioned underneath the fluidic sorting channel to generate a magnetic field;

flowing the magnetically labelled cell sample through the fluidic sorting channel;

collecting two or more, preferably three, subpopulations from two or more outlets or outlet ports coupled to the fluidic channel, each one of the outlets or outlet ports being configured to receive a subpopulation of the magnetically labelled cell sample;

assaying at least one of the two or more subpopulations to identify the putative genetic regulator.

The genetically edited cells may comprise a plurality of cells wherein a level of a molecule edited in a cell is decreased by at least 80% and/or knocked out.

In one embodiment, the genetically edited cells comprise a RNAi screen, a Zinc-finger nuclease screen, a TALEN screen or a CRISPR screen. In a CRISPR screen, typically cells, such as HAP1 cells or any Cas9 or other CRISPR nuclease expressing cells, are infected with a CRISPR lentiviral library and edited cells are selected for example by antibiotic selection and passaged under selection pressure to produce CRISPR edited cells. In one embodiment, the heterogeneous cell sample is prepared by mutagenizing a cell line using a CRISPR library, propagating and selecting CRISPR edited cells, optionally for 5 to 20 doublings, for example 12 doublings, and sorting the cells using a method and/or a microfluidic device or kit described herein. Any CRISPR library can be used. For example, the pLCKO- TKOv3 plasmid library[25] (Addgene, Watertown Mass.) can be used to prepare the CRISPR lentiviral library. The CRISPR lentiviral library preferably comprises multiple sgRNAs per gene and can target upwards of 15000 protein coding genes.

HAP1 cells were used in the Examples. HAP1 cells are small (~10 μm in diameter) and express CD47 at high levels (FIGS. 17A, B, C, E, F), thus providing a robust system for cell sorting based on protein expression. However, the microfluidic devices described herein, can also be applied to larger cell types such as LNCaP and PC3 (FIG. 17A) and intracellular and surface markers expressed at lower density, e.g. EpCAM and vimentin (FIGS. 17B, C, E, F). At an optimized flow rate, the "MICS" microfluidic device has higher throughput and performs comparably to flow cytometry in terms of for example viability and ratio or separated cells for both markers in both cell lines (FIGS. 17D, G). These results demonstrate the flexibility of the devices described herein as a customizable cell sorting platform.

The microfluidic device chips described herein maintain high cell viability after sorting and can target for example about 8000 target cells/sec per chip and are compatible with whole blood.

The heterogeneous cell sample can be any sample comprising cells to be sorted wherein the level of a target marker varies.

In an embodiment, the heterogeneous cell sample is a pooled cell sample, optionally a pooled cell sample, comprising $10^6$, $10^7$, 108 or $10^9$ screened cells optionally CRISPR edited cells, optionally comprising at least, about or greater than 2,500 5,000, 10,000, 20,000, 50,000 or 100,000 target cells. As described herein and in the Examples, the described microfluidic devices of the disclosure are particularly useful for handling and sorting large collections of CRISPR edited cells based on phenotypic changes. Using the "MICS" microfluidic chip device described herein, the inventors were able to identify molecules that modulated CD47 cell surface display and identified glutaminyl cyclase QPCTL as a bona fide modifier of CD47 levels, demonstrating that the devices described herein are useful with genome scale phenotypic CRISPR screens. Methods for performing CRISPR screens are described herein and in the art.

Any of the microfluidic devices described herein can be used. The chips can be combined in parallel as shown for example in FIG. 3D. The microfluidic parallelized device is particularly useful for genome wide or other largescale screens facilitating set up and permitting sorting of for example 200 million cells/hr.

Various CRISPR screens can be performed and used with the microfluidic devices and methods described herein. The CRISPR screen can for example be a CRISPR transcriptional repression screen (CRISPRi) a CRISPR transcriptional activation screen (CRISPRa) or a typical CRISPR knock out screen.

Depending on the desired screen and the heterogeneous cell population to be sorted, any one of the low target marker, high target marker or medium target marker subpopulations may be of particular interest. Putative negative genetic regulators can for example be identified by analysing the subpopulation with high target marker levels (e.g. the subpopulation most deflected).

The heterogeneous cell sample can be labelled with a magnetic label directly or indirectly. For example a method described in the Examples can be used. In one embodiment, the heterogeneous cell sample is incubated with a binding agent such as an antibody or ligand, optionally that comprises biotin or a fluorochrome or other molecule to which an antibody can be raised, the heterogeneous cell sample and binding agent are incubated with a secondary binding agent magnetic bead and the cells are isolated.

In some embodiments, one or more of the sorted subpopulations is assayed for sgRNA abundance. This can be done by isolating genomic DNA from the subpopulation, PCR amplifying the sgRNA and sequencing the sgRNAs and compared for example to sgRNA abundance prior to sorting or compared to an earlier sorting. To determine if a sgRNA is enriched in a subpopulation, normalized z scores can be calculated as described in Colic et al, 2019[27], optionally a high target marker subpopulation and/or a low target marker subpopulation. The identified enriched sgRNAs can be compared to a reference database for sgRNA representation to exclude for example essential genes.

The methods can be used to identify negative and/or positive regulators. When positive regulators—positive regulating genes—are decreased and/or knocked out, levels of the target marker decrease. When negative regulators—negative regulating genes are decreased and/or knocked out, levels of the target marker increase.

The level may increase or decrease based on a change in expression, transcription, processing, modification, or transport of the target marker, or masking or greater access to an epitope in the target marker.

In an embodiment, any of the methods herein comprise one or more steps described in the Examples.

V. Kits

A kit can include a microfluidic chip device as described in the present document. The kit can further include tubing for connecting to the microfluidic chip device and/or any other component described herein.

A kit can include a microfluidic parallelized device as described in the present document.

In an embodiment, the kit is for and/or comprises instructions for performing a method described herein.

Also provided in another aspect is an assembled system comprising a microfluidic device described herein, optionally a microfluidic chip device or a microfluidic parallelized device, and one or more of tubing, collection containers, pump or pumps, inlet reservoirs etc.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure.

EXAMPLES

Example 1

Pooled CRISPR-Cas approaches allow systematic classification of genetic elements into functional categories and biological processes. Through introduction of targeted mutations, genome-wide screens can identify key regulatory components of a desired biological activity in stem cells (e.g. self-renewal and differentiation), or reveal novel regulators particular signaling pathways. One of the challenges in pooled CRISPR approaches is the lack of rapid and robust selection approaches for high-throughput isolation of viable cells based on changes in biomarker expression.

In order to address this unmet need, a scalable immunomagnetic sorting platform and methodology amenable to high-throughput screening of cell populations was developed. This is accomplished by utilization of a microfluidic device capable of high-efficiency isolation of magnetically-labelled target cells from a heterogeneous pool. The device achieves separation by binning cells according to marker expression using ferromagnetic guides. This approach is versatile with respect to the choice of cell lines, markers and type of CRISPR library and has been validated to have the requisite resolution and throughput for isolation of distinct target cells from a CRISPR screen.

Background and Description

Stem cells (SC) have demonstrated clinical potential in regenerative medicine.[1,55] In order to efficiently deploy stem cell therapies, new tools to understand and control their biology must be developed. The identification of key regulatory elements for promoting a desired biological activity in stem cells (e.g. self-renewal or differentiation) is a necessary step in this process.

Figure 11D:
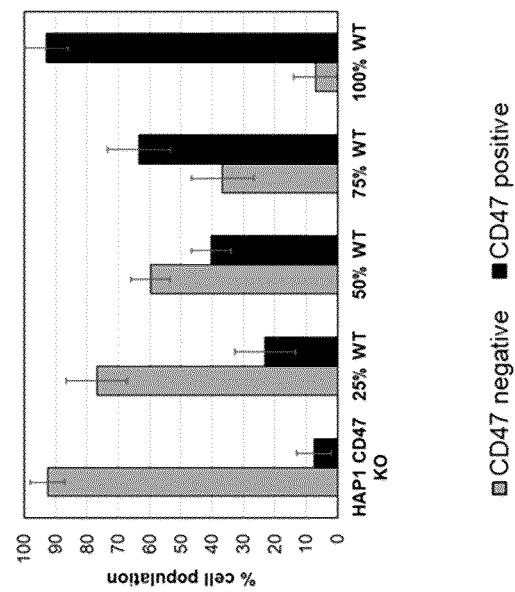
FIG. 11D is a graph of preliminary validation experiments before CRISPR-Cas9 Knockout screen. Spiking WT cells with sgCD47 #1 transduced cells (after two rounds of enrichment for low CD47) and then sorting showed that initial ratios could be recovered and the microfluidic device could accurately sort mixed cell types.

Pooled CRISPR-Cas approaches present an opportunity for systematic classification of genetic elements into functional categories and biological processes. Loss-of-function screens using the CRISPR-Cas9 system or gene-trap technology have been used to determine genetic interactions and their modifiers in mammalian cells.[3,6,24,25,56,57] For instance, in cases of strongly and homogeneously expressed proteins, sorting a mutagenized cell population for rare cells with significant reduction in marker expression allows the identification of positive regulators (FIG. 11A). Likewise, negative regulators of markers can be identified. However, such modifier screens have been hindered by the requirement of isolating a subset of rare cells from a large population. Fluorescence activated cell sorting (FACS) has been the standard technique for isolation of target cells from a heterogeneous population in non-lethal phenotyping screens. This technique, however, is afflicted with long processing times (requiring fixation of the cells), high processing costs, and low cell viability, making screening sensitive cell types a challenge. Thus, new rapid and robust selection approaches for capture of cells based on biomarker expression solutions are necessary to realize the potential of CRISPR-based screens.

In order to address this unmet need, a device and methodology for high efficiency microfluidic-based cell separation technology for use in combination with genome-wide CRISPR-Cas9 loss-of-function screens as an unbiased and comprehensive method for identification of modifiers of marker expression was developed.

Results

Design and Development of a High-Efficiency Sorting Device.

To effectively separate and profile magnetically labelled cells from a bulk population, a microfluidic chip was designed which uses angled ferromagnetic guides to induce a lateral deflection of magnetically labelled target cells.[58-61] This device harnesses the high magnetic permeability of Metglas 2714A, a cobalt-based magnetic alloy, to generate an enhancement in an external magnetic field to achieve high sorting efficiency and throughput.[62] To fabricate the chip, ribbons of Metglas are patterned into deflection guides with increasingly steep angles relative to the direction of flow in a microfluidic chip. The deflection guides lead to a varying number of outlets for cell collection (FIG. 3A).

As shown in FIG. 3A, cells flowing in a focused central stream are deflected by the combination of magnetic capture and fluidic drag forces. The magnitude of the magnetic capture force is dictated by the amount of magnetic loading on the surface of the cell. Each cell reaches its maximal deflection when the magnetic trapping force is too small to balance the component of the fluidic drag force acting perpendicular to the guides.

The device was designed to have the requisite throughput to process the high numbers of target cells required for CRISPR based live cell screening. This device allows to perform a binary sort on magnetically labelled cells, distinguishing expressing cells from non-expressing cells. With this design, it was possible to achieve a high throughput approaching $20 \times 10^6$ cells/hour/chip. This cutoff was determined to be suitable for the collection of the number of cells per hour needed to provide adequate library sampling while maintain cell viability.

In this device, the sample to be analyzed enters the device at the top of the figure shown with a sheath buffer fluid in laminar flow. As cells pass through the device they flow over top of patterned cobalt-based alloy with exceptionally high magnetic permeability. In the presence of a high magnetic field this patterned layer becomes magnetized and guides magnetically-labelled target cells to deflect laterally to the edges of the device. The deflected cells are then captured into separate populations at the outlet of the device. The number of outlets can be varied. Unlabelled cells do not deflect and end up in the central outlet of the device. By balancing the drag force (determined by the choice of buffer and flow rate) and magnetic force (determined by labelling protocol, strength of magnetic field and angle of guides) the expression level demarking selected and non-selected cells can be tuned for the specific application.

Genome-Wide CRISPR Knockout Screens.

CRISPR (Clustered Regularly Interspaced Short Palindromic Repeats) technology has generated tremendous excitement in the life sciences. This novel tool allows researchers to easily manipulate large amounts genetic information simultaneously. Once these edits are made the cells are allowed to proliferate and later are sorted for a particular phenotype that changes as a result of the genetic changes. The most common phenotype to assess is cell viability, but screens have also evaluated upregulation of a marker protein (positive screen) or downregulation (negative screen) or both[3]. By comparing the genomic set before perturbation and after, links between the genotype to phenotype relationships can be identified. For marker screens the target and non-target cells must be sorted.

This has conventionally been done with fluorescence-activated cell sorting (FACS) technology[6]. But FACS sorts cells serially and due to the large number of cells ($>10^8$) required for coverage of the sgRNA library, the sorts can last hours to days[3]. Besides the operating costs and time, this requirement can also reduce capability. Cells may need to be fixed, thereby preventing further growth and analysis.

The technique was validated by performing a CRISPR-Cas9 KO screen on HAP1 cells assessing CD47. HAP1 cells are derived from chronic myeloid leukemia cell line and are near haploid—expressing only one copy of every gene so phenotypic changes are more pronounced. CD47 (Cluster of Differentiation 47) is a transmembrane receptor found in all human cells which has been implicated in apoptosis, cell proliferation, cell adhesion, cardiovascular and immune system response. It was chosen as a target because in the tumor microenvironment CD47 expression is high and via the SIRPα pathway suppresses phagocytosis, disabling the immune system ability to fight the tumor. This screen could act as a stepping stone towards more complex hESC screens while also shedding light on the regulatory system of an important marker in cancer biology.

Figure 11C:
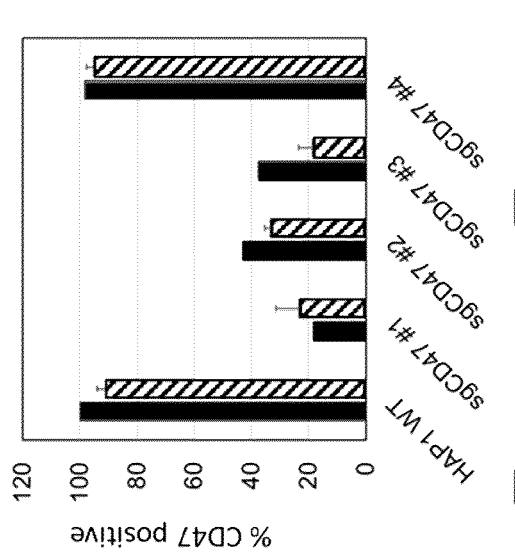
FIG. 11C is a graph of preliminary validation experiments before CRISPR-Cas9 Knockout screen. Three of four cell lines with the CD47 gene knocked out (each line with a unique sgRNA) show a decrease in CD47 expression with both flow cytometry and microfluidic sorting. Guide #4 was confirmed to be ineffective at gene inactivation
Figure 11B:
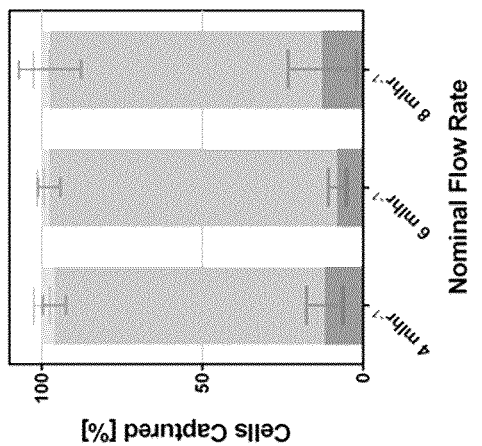
FIG. 11B is a graph of preliminary validation experiments before CRISPR-Cas9 Knockout screen. Wildtype (WT) HAP1 cells are predominately sorted into the medium bin. This allows for cells with both upregulated and downregulated CD47 expression to be identified.

Preliminary validation experiments were conducted to demonstrate the utility of the microfluidic device for the process of phenotypic profiling in a genomic screening capacity. As shown in FIG. 11A-C, this included sorting the wildtype (WT) HAP1 cells at different flow rates to decide on the ideal operating conditions, assessing the sorting of HAP1 cells transduced with sgRNAs targeting the CD47 gene (which should result in a decrease in the number of CD47+ cells), and mixing WT and clone cells together, sorting them and recovering the initial ratios. Experimental parameters were designed to have the majority of WT HAP1s be sorted into the middle bin thus upregulation and downregulation of CD47 could be assessed.

Figure 11E:
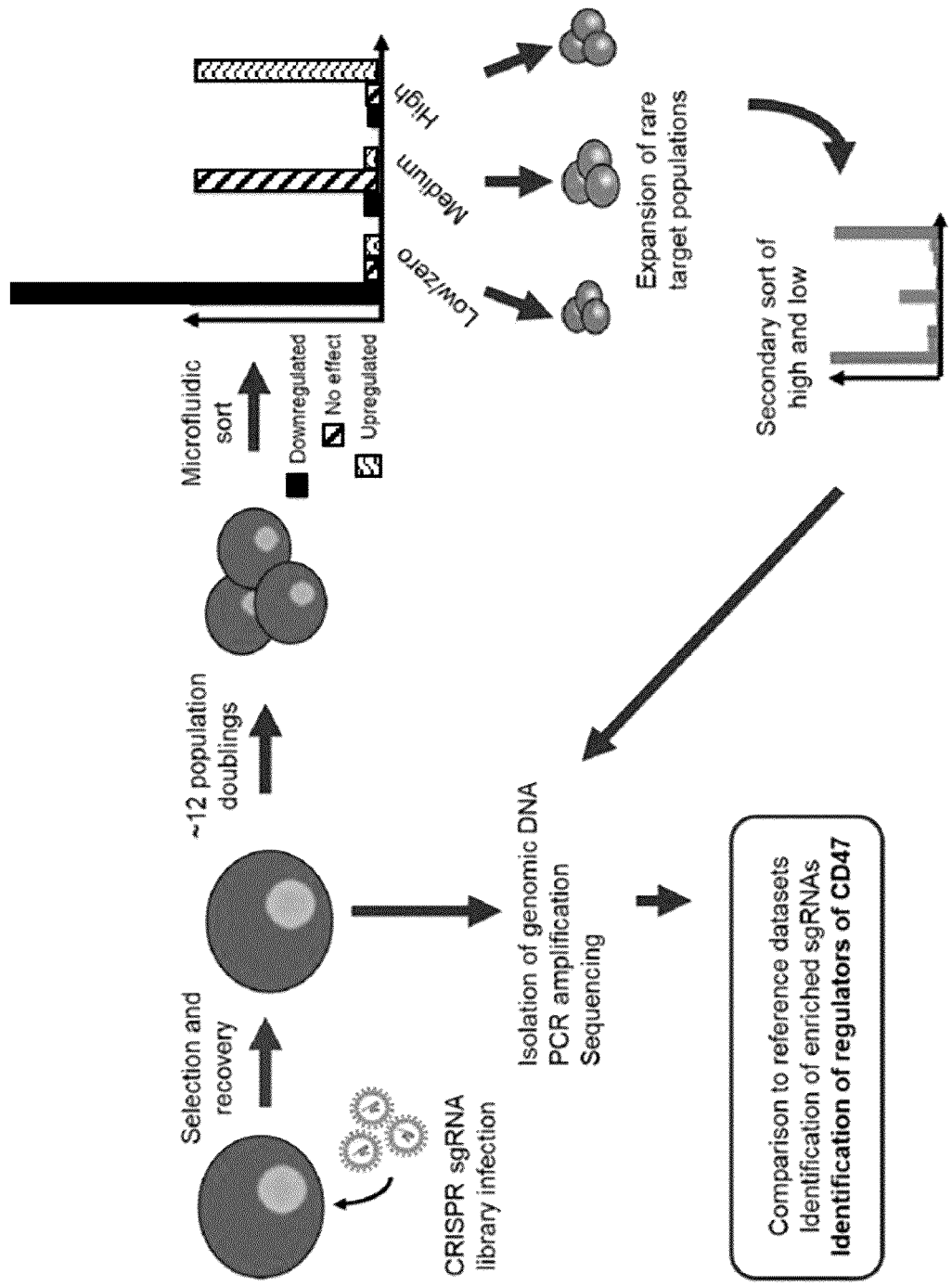
FIG. 11E is a schematic representing the pipeline of the CRISPR-Cas9 Knockout screen in HAP1 cells. Cells were first transduced with the sgRNA library then selected with puromycin. Cells were sequenced and sorted at T0, sorted at T0++, T12 and T12++. Comparison between genetic data sets identified genes that affected CD47 expression.

The pipeline of the screen is provided in FIG. 11E. HAP1 cells were infected with a CRISPR Cas9 sgRNA library (TKO V3), selected using antibiotics and then sequenced to provide a reference data set. At the same timepoint cells were sorted using the microfluidic chip and a CD47 antibody (T0). The high and low expressers were then grown for three days and sorted again (T0++). The cells were then grown for 12 days and sorted a third time (T12). The high and low CD47 expressers from this sort were again plated and grown in culture for 3 days and sorted a final time (T12++). The final high and low CD47 expressers were then sequenced and the genomic data set compared against that of T0 and T12 for unsorted cells to identify gens that affected CD47 expression (known as hits). Three biological replicates (A, B, C) were done.

Figure 11F:
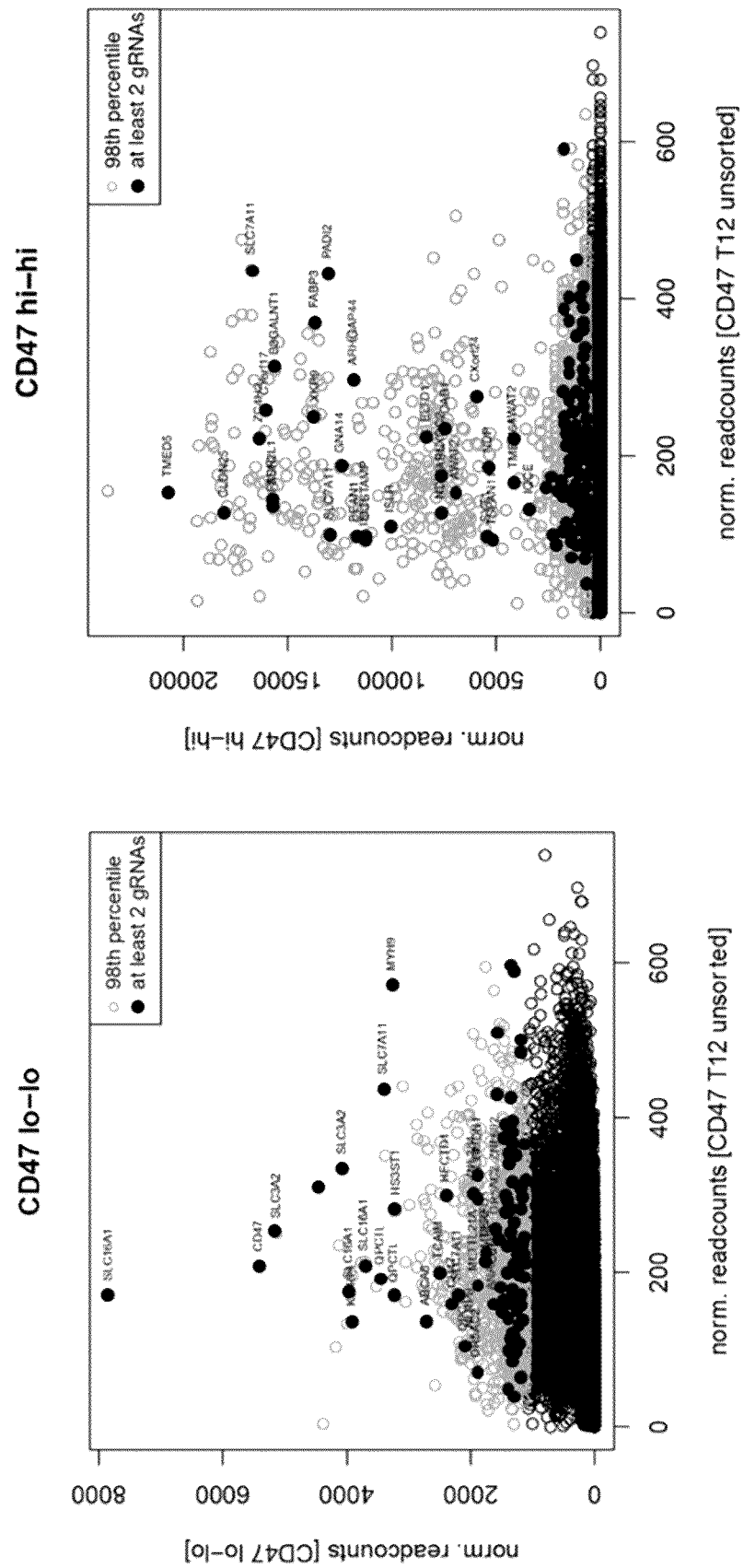
FIG. 11F is a graph representing hit plots form the CRISPR-Cas9 Knockout Screen in HAP1 cells. Individual points are individual sgRNAs, filled in black circles indicates that for the gene that sgRNA targeted there were two or more sgRNA identified as hits (i.e. enriched, top 2% of read-depth normalized counts). The library has 4 sgRNA per gene, more enriched sgRNAs targeting the same gene indicate more confidence. Through functional analysis, many of the hits were identified as being involved in cell metabolism.

The preliminary hit list is shown in FIG. 11F. It should be noted that the CD47 guide came up as a top hit, supporting the validity of this screen. In total 950M cells were sorted and processed within 1.2 hours. Processing by FACS for this number of cells would take 50 to 150 hours to be sorted.

Example 2

MICS device fabrication. Strips of Metglas 2714A were obtained from Metglas and epoxy bonded (Loctite M-31CL, McMaster-Carr) onto 100 mm soda lime glass wafers (550 μm thick, University Wafer) and left to cure for 24 h. Excess epoxy was removed with acetone. The metallic surface was then primed with MCC 80/20 (Microchem) prior to spin coating with S1811 positive photoresist (Microchem). The positive resist was photolithographically patterned, and then the exposed Metglas 2714A was etched using a mixture of 3.6% HCl (Sigma), 14.3% $H_2O_2$ (Sigma) and 82.1% $H_2O$. After stripping the remaining photoresist and priming the surface with OmniCoat to improve adhesion, the ferromagnetic guides were encapsulated with a layer of SU-8 3010 (Microchem), and then microfluidic channel features were patterned with a 100 μm layer of SU-8 3050 (Microchem). Each chip was then capped with cured PDMS with holes cored for all inlet and outlet ports, following an APTES treatment (Sigma).[47] To minimize friction and limit cell adhesion to the chip surfaces, every chip was treated with a solution of 1% w/v pluronic F108 (BASF) in DI $H_2O$ for a minimum of 12 h.[48]

Further details are provided in Example 3.

Example 3

Microfluidics offers precise spatial-temporal control over fluids and cells due to the laminar flow generated by their small geometric size. Using immunomagnetic nanobeads, i.e. antibodies coupled to magnetic beads, which bind specifically to a target protein found in or on a cell, these devices can be used to sort cell populations based on the expression of the target protein. Although the low manufacturing and operating costs and high speed at which these devices operate have made them a competitive alternative to cell sorting by FACS, the limited throughput of these small devices has consistently remained a barrier to adoption for large-scale applications.

An immunomagnetic microfluidic sorter is described in Aldridge, P. et al. Prismatic Deflection of Live Tumor Cells and Cell Clusters. ACS Nano. 12, 12692-12700 (2018)[13]. To improve throughput and devising a method to operate up to 30 chips in parallel (MICS), the present microfluidic chip device successfully demonstrated the sorting of a large live cell population into three outlet populations in one hour while maintaining high cell viability for the purpose of genome-scale phenotypic screening as described in the following Examples. The observed sorting capacity of up to 1 billion cells per hour considerable surpasses the throughput achievable by FACS, the gold standard for phenotypic cell sorting.

The protocol presented here outlines how to fabricate and operate microfluidic chips for performing MICS.

Reagents and Equipment

For Device Operation
  Hanks' Buffer Saline Solution Mg2+ free, Ca2+ free (Thermo Fisher Scientific 88284)
  Bovine Serum Albumin (Sigma-Aldrich A7906)
  Fetal Bovine Serum (Thermo Fisher Scientific A3382101)
  Anti-Biotin MicroBeads UltraPure (Miltenyi Biotec 130-105-637)
  Biotinylated antibody of user's choosing
  EDTA (Thermo Fisher Scientific AM9260G)
  Silicone tubing (McMaster-Carr 51845K51)
  PTFE tubing (Component Supply Company STT-21)
  3 ml, 10 ml and 20 ml plastic BD syringes (Thermo Fisher Scientific 13-689-8)
  Dispensing needle with luer-lock connection (McMaster-Carr 75165A674)
  Syringe pump (Chemyx Fusion 200, 07200)
  Pluronic® F-108 (Sigma Aldrich 542342)
  2"×½"×½" Grade N52 NdFeB permanent magnet (one per chip) (K&J Magnetics BY088-N52)

For Fabrication
  EA M-31CL epoxy (McMaster-Carr 7370A38)
  Metglas 2714A (Metglas Inc.)
  Acetone
  Isopropyl alcohol (2-propanol, IPA)
  MCC 80/20 primer (Micro-Chem Inc.)
  S1811 photoresist (Micro-Chem Inc.)
  MF312 developer (Micro-Chem Inc.)
  AZ300T stripper (Micro-Chem Inc.)
  Omnicoat primer (Micro-Chem Inc.)
  SU-8 3010 (Micro-Chem Inc.)
  SU-8 3050 (Micro-Chem Inc.)
  Polydimethylsiloxane (PDMS) (Ellsworth Adhesives 4019862)
  Convection oven
  Spin coater
  Wafer dicer
  Mask aligner
  Vacuum plasma chamber Procedure Chip Fabrication The microfabrication of the MICS chip consists of bonding Metglas foil to a glass wafer, three photolithography steps, dicing the wafer and bonding a PDMS ceiling.

1. Spin coat epoxy on soda lime glass wafers.
2. Clamp Metglas 2714A foil to wafer overnight.
3. Take wafers to cleanroom.
4. Rinse wafers with acetone, then IPA, then dry with N2 and bake at 95° C. for 5 minutes.
5. Spin coat (300 RPM, 20 seconds) MCC 80/20 primer.
6. Bake for 2 minutes at 95° C.
7. Spin coat (500 RPM 10 seconds, 2000 RPM, 30 seconds) S1811 photoresist.
8. Prebake at 95° C. for 3 minutes.
9. Hard contact exposure of first mask, 150 mJ/cm2, i-line. The first mask is used to pattern the 50 Metglas.
10. Develop with MF 312 developer for 30 seconds, rinse with water
11. Etch with Metglas etchant (HCl:H2O2:H2O, 1:4:23) for approximately 8 minutes or until guides are well defined. Pipette bubbles away during etching.
12. Strip remaining resist with AZ300T, rinse in fresh stripper, then acetone, then IPA, N2 dry.
13. Dehydrate wafer at 115° C. for 3 minutes.
14. Spin coat Omnicoat (500 RPM 5 seconds, 3000 RPM 30 seconds).
15. Bake at 115° C. for 2 minutes.
16. Spin coat (1000 RPM 30 seconds) SU-8 3010 photoresist.
17. Prebake at 95° C. for 10 minutes.
18. Soft contact exposure of second mask, 200 mJ/cm2, i-line. The second mask is used to encapsulate the Metglas in SU-8.
19. Post-exposure bake, ramp from 65° C. to 95° C., hold for 3 minutes then cool gently.
20. Develop in SU-8 developer for 45 seconds.
21. Hard bake, ramp from 65° C. to 150° C., hold for 15 minutes then cool gently.
22. Spin coat (500 RPM 10 seconds, 1000 RPM 45 seconds) SU-8 3050.
23. Prebake at 95° C. for 1 hour.
24. Soft contact exposure of third mask, 250 mJ/cm2, i-line. The third mask is used to build the channels walls of the device, which can also made from SU-8.
25. Post-exposure bake, ramp from 65° C. to 95° C., hold for 6 minutes then cool gently.
26. Develop in SU-8 developer for 6 minutes.
27. Take wafers out of cleanroom.
28. Dice wafers using a dicing saw.
29. Cast PDMS slabs, same size as diced devices, be sure to set on glass slide so surface is smooth. Cure in 70° C. oven overnight.
30. Punch holes for inlets and outlets.
31. Plasma treat PDMS in vacuum plasma chamber for 45 seconds
32. Place in 10% v/v APTES:DI water solution for 30 minutes.
33. Rinse with DI water and N2 dry.
34. Place treated PDMS onto devices, apply weight and put in in 70° C. oven overnight.

Cell Labelling

1. Lift cells from culture flasks using 0.125% trypsin, wash with PBS and resuspend at a concentration of 10^7 cells/ml in a solution of HBSS supplemented with 2% BSA.
2. Count cells and measure viability using automated cell counter (e.g. Countess from Thermo Fisher Scientific).
3. OPTIONAL: fix cells using 4% v/v PFA/PBS for 15 minutes at room temperature (RT) or 90% v/v ice-cold methanol/PBS added drop-wise and incubate on ice for 30 minutes.
4. OPTIONAL: permeabilize cell plasma membrane using 0.5% Triton-X-100/PBS for 12 minutes at (RT)
5. OPTIONAL: block cells in 1% v/v FBS/PBS for 30 min.
6. Label cells with biotinylated primary antibody as per manufacturer's instructions.
7. Wash cells 3× in blocking buffer (2% v/v BSA/HBSS).
8. Remove supernatant.
9. Label cells with anti-biotin microbeads. The volumes presented are for up to 10 million cells. If labelling more cells, scale accordingly but if labelling less than ten million cells still use these volumes.
   a. Resuspend cells in 80 μL of blocking buffer.
   b. Add 20 L of anti-biotin microbeads (sufficient for 10 million cells).
   c. Incubate at 4° C. for 30 minutes.
10. Resuspend cells in degassed sorting buffer (degassed 2% BSA/HBSS+3 mM EDTA) to desired sorting concentration (1*10^6 to 5*10^6 cells/ml).
    a. Buffer can be degassed by putting in Erlenmeyer flask under vacuum for 30 minutes.

Chip Set Up

The day before sorting, chips are degassed by filling with 1% m/v Pluronic® F-108 in DI water and leaving overnight. This process removes any air from the device and lubricates the SU-8 surface.

1. Remove plunger from two 10 ml syringes per chip, place in stand and add luer-lock fitting. Label one syringe as "sample" and the other as "sheath".
2. Connect one inlet tube from chip to "sheath" syringe, allow pressure of degassing solution to backfill "sheath" syringe.
3. Once "sheath" syringe is filled, remove other inlet tube from degassing set-up, add 20 cm of PTFE tubing, connect to the "sample" syringe and allow the height of the buffer in each syringe to equalize.
4. Once solution has equalized, remove most of the degassing solution (leaving a small amount of fluid to prevent air from entering chip).
5. Fill with degassed sorting buffer, allow to flow from inlet syringes through to outlet syringes, flushing out all degassing solution.
6. Meanwhile, for each chip place a 20 ml, 10 ml and 3 ml syringe in Chemyx syringe pump and add luer-lock fittings. These syringes correspond to low (20 ml), medium (10 ml) and high (3 ml) outlets. A 3D-printed holder can be used to hold up to 5 sets of syringes per pump. Ensure the syringes are fully depressed, the pump has been set to withdraw mode and the 20 ml syringe is selected in the pump menu. Select desired flow rate.
7. Connect outlet tubing to outlet syringes, ensure the tube on the outside of the chip is connected to the 3 ml syringe, and the inside-most tubing is connected to the 20 ml syringe.
8. Run pump for 2 minutes to remove any air in tubing.
9. Place chip on top of magnet, centred overtop of magnetic guides and not on inlets/outlets. Double sided tape can be used to ensure the chip does not easily fall off.

Sorting
1. Clamp "sample" syringe, remove sorting buffer and add cell solution.
2. Tap syringes to dislodge any bubbles on the sidewalls of the syringes or luer-lock fittings.
3. Ensure that the levels of "sample" and "sheath" fluid in the inlet columns are at the same height (they should remain the same height for the duration of the sort).
4. Complete checklist:
    All tubing is connected to correct size syringes.
    No chips have any bubbles.
    All pumps have been set to "withdraw" mode.
    All pumps have been set to 20 ml syringe size.
    All pumps have been set to correct flow rate.
5. Press start on all pumps, sorting will begin.
6. While chips run, continue to check that inlet column heights remain the same, and there are no air bubbles within the chips.

Sample Collection
1. Allow chips to run dry (i.e. stop running no sooner and no later than air bubbles start to appear within the chip). Individual chips can be "stopped" by clamping outlet tubing and removing tubing from outlet syringes. This allows the pump to run other chips while disconnecting others.
2. Once all chips are finished, clamp outlet tubes.
3. Remove tubing from all outlet syringes.
4. For each outlet syringe, label a 15 ml falcon tube and weigh the tube.
5. Fill each falcon tube with the contents of the appropriate syringe.
6. Weigh the falcon tubes again, the mass difference can be used to calculate the volume of fluid collected, assuming a density of 1 g/ml.
7. Take a small (10 μL) sample from each tube for automated cell counting and viability measurement.
8. Use remaining cells for future purposes depending on the application of this platform.

Analysis
1. Calculate the efficiency of each chip (percentage of cells in each outlet) and the recovery (total cells collected/total cells in sample*100%). The efficiency should match previous sorting or flow cytometry experiments, or desired effect should be seen, depending on application (e.g. higher percentage in low outlet for CRISPR KO screen). Cell recovery should be >90%.

Example 4

Presented here is a rapid and scalable high-throughput approach to phenotypic CRISPR-Cas9 screening using immunomagnetic cell sorting facilitated by a microfluidic chip (MICS) described in Examples 1, 2 and 3.

To study factors that modulate the display of CD47—an important drug target—on the cell surface, an entire genome-wide screen containing more than $10^8$ cells was processed in under one hour and high levels of cell viability were maintained. The technology considerably surpassed the throughput achieved by flow cytometry, the gold standard for phenotypic cell sorting. In the enriched cell populations, modulators of CD47 function were robustly identified including QPCTL, an enzyme required for formation of the pyroglutamyl modification and ligand interaction at the N-terminus of this protein.

The screen was for identifying positive and negative regulators of CD47 cell surface display. CD47 is widely expressed across cell types and acts as a "don't eat me" signal through inhibitory interactions with SIRPα, a protein expressed on macrophages and other myeloid cells that negatively regulates phagocytosis[14]. CD47 is highly expressed on various tumour types, and blocking the CD47-SIRPα interaction has been explored as a novel cancer immunotherapy strategy that has shown promising initial results for some cancer types[15-17]. MICS enabled the processing of a whole genome-wide screen with more than $10^8$ cells in under one hour, greatly exceeding the throughput that is feasible by flow cytometry. The glutaminyl cyclase QPCTL was identified as a modifier of CD47, an enzyme catalyzing the cyclization of N-terminal glutamate and glutamine to pyroglutamate (pyro-Glu). This interaction was validated using both genetic and chemical perturbations of QPCTL. A highly sensitive PRM-mass spectrometry assay was developed for directly and quantitatively measuring the pyro-Glu modification at the endogenous CD47-N-terminus.

Results

Figure 12A:
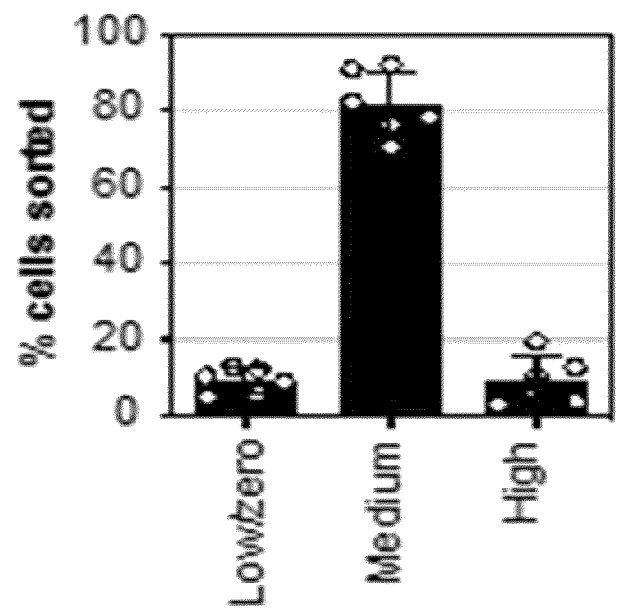
FIG. 12A is a graph illustrating the outlet profile of HAP1 cells sorted with the HT-miCS chip, labelled with magnetic beads targeted to CD47 at a sample flow rate of 6 ml/hr. Data represent mean±SD of n=3 biological replicates and n=2 technical replicates.
Figure 12B:
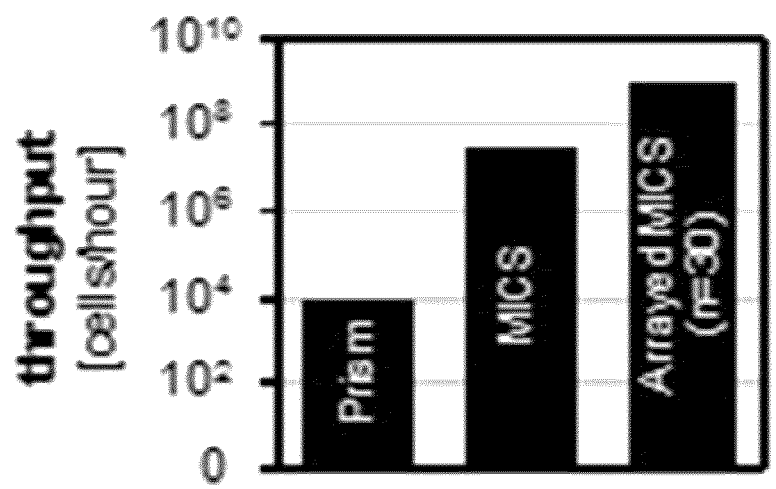
FIG. 12B is a graph illustrating the throughput of microfluidic chip sorting. Numbers are calculated based on observed throughput with Prism chip (Aldridge et al., 2018)[13] and HT-miCS for 1 and 30 chips.
Figure 15B:
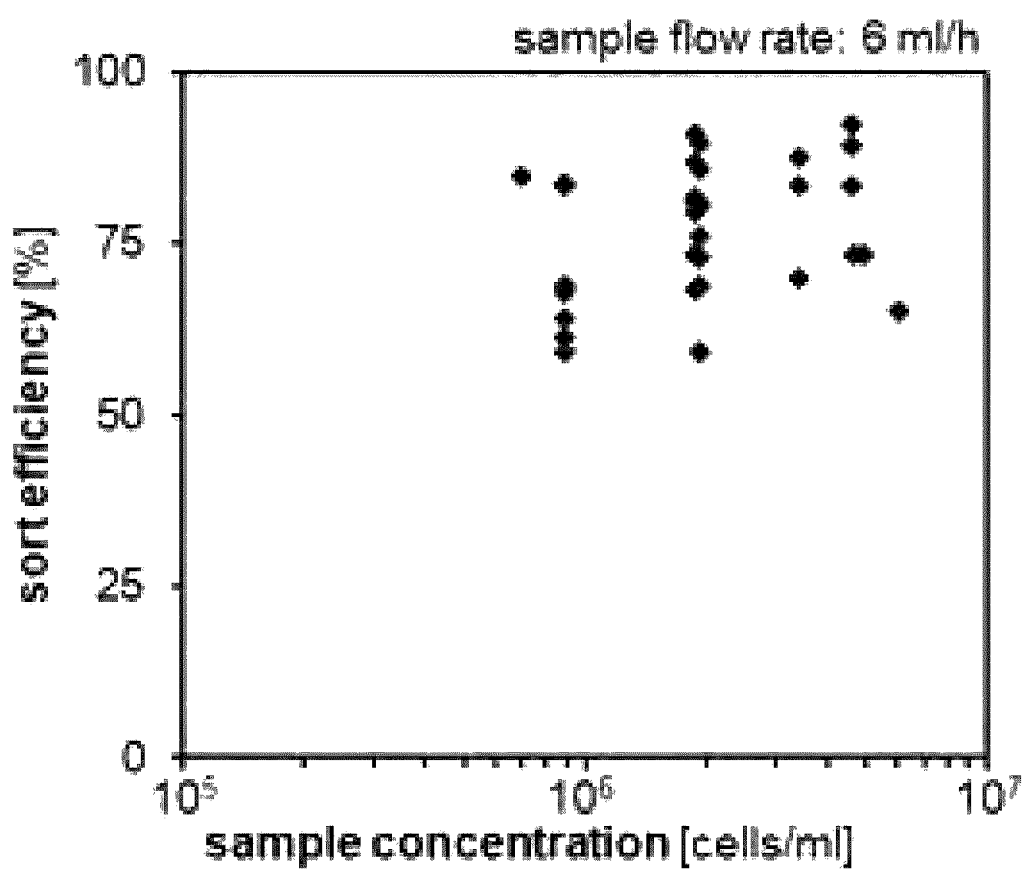
FIG. 15B. is a graph illustrating throughput optimization to determine maximum sample concentration at optimal flow rate (6 ml/hr) and sort efficiency. Sort efficiency was calculated as the percentage of sorted cells directed out of the low/zero outlet. Data represent individual measurements performed using different chips and biological samples.
Figure 16A:
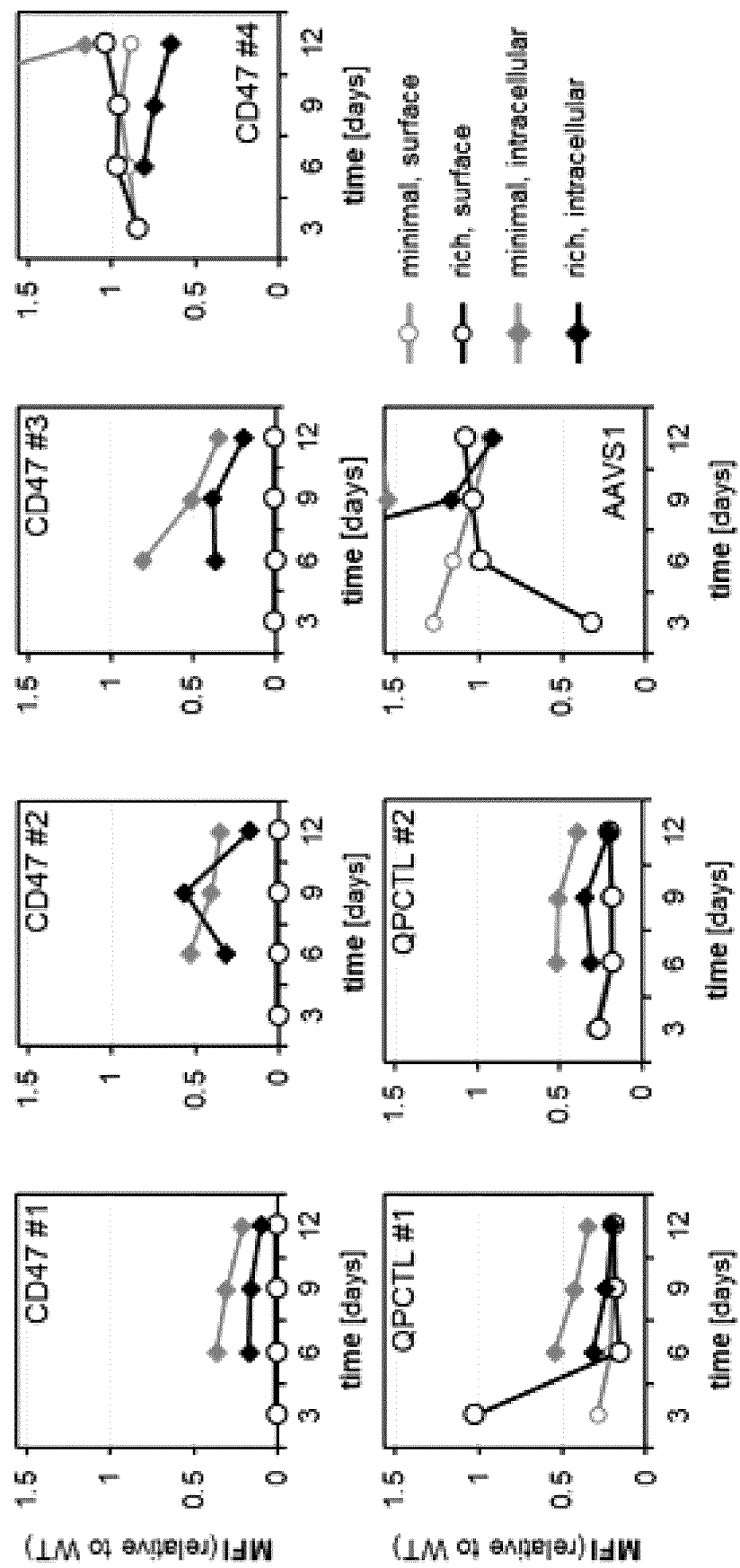
FIG. 16A is a series of graphs illustrating the results of cell surface and intracellular flow cytometry (CC2C6 antibody) of HAP1 cells transduced with sgRNAs targeting CD47, QPCTL and QPCT as indicated, 3-12 days post-selection in minimal or rich medium. AAVS1 sgRNA was used as control. Data represent the relative median fluorescence intensity (MFI, to wild-type). CD47 #4 and AAVS1 values>1.56 were not plotted. See methods for details.
Figure 16B:
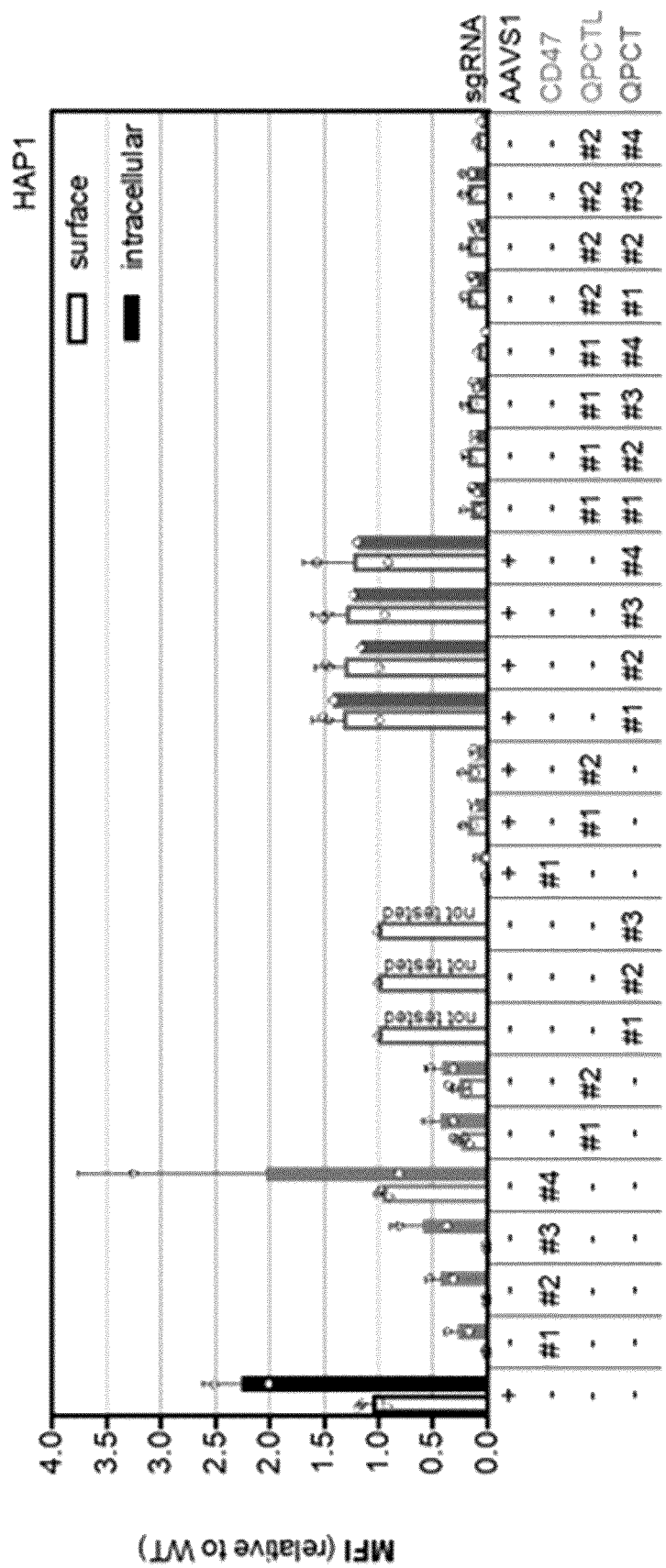
FIG. 16B is a graph illustrating results of experiments in FIG. 16A 3-6 days post-transduction. Mean f SD relative MFI of n≥2 biological replicates from independent experiments.
Figure 16C:
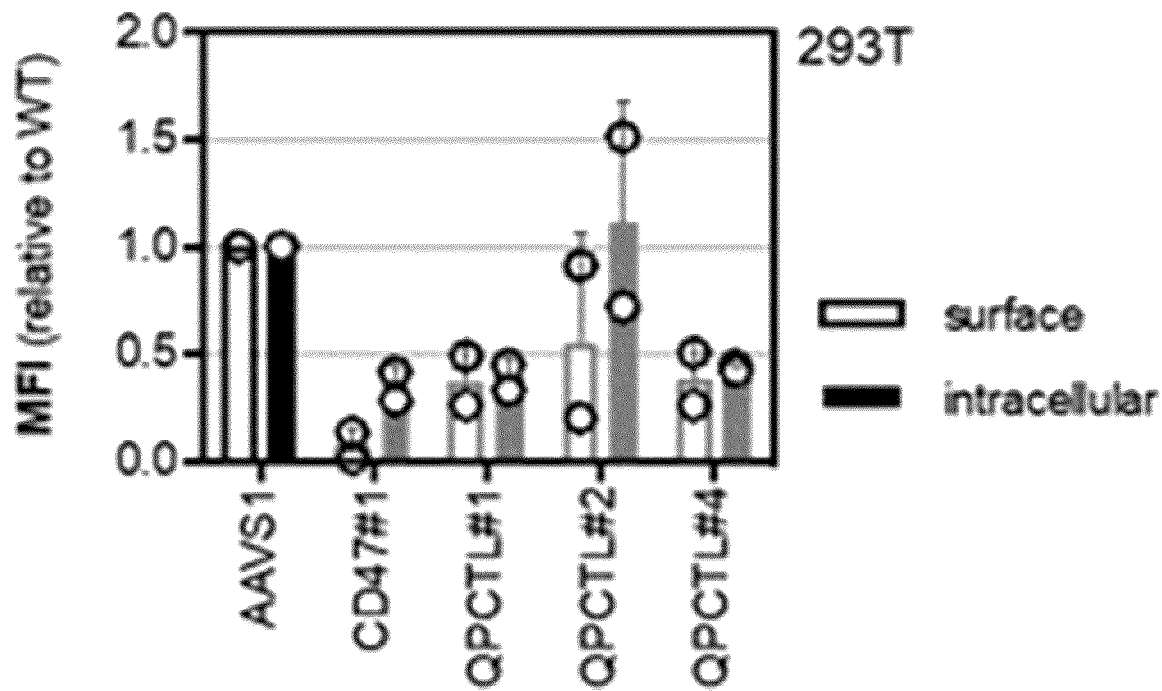
FIG. 16C. is a graph illustrating the results of cell surface and intracellular flow cytometry (CC2C6 antibody) of 293T cells transduced with sgRNAs targeting CD47, QPCTL and QPCT as indicated, 5-12 days post-selection in minimal or rich medium. n=2 biological replicates from independent experiments. Data are displayed relative to AAVS1 control.
Figure 16D:
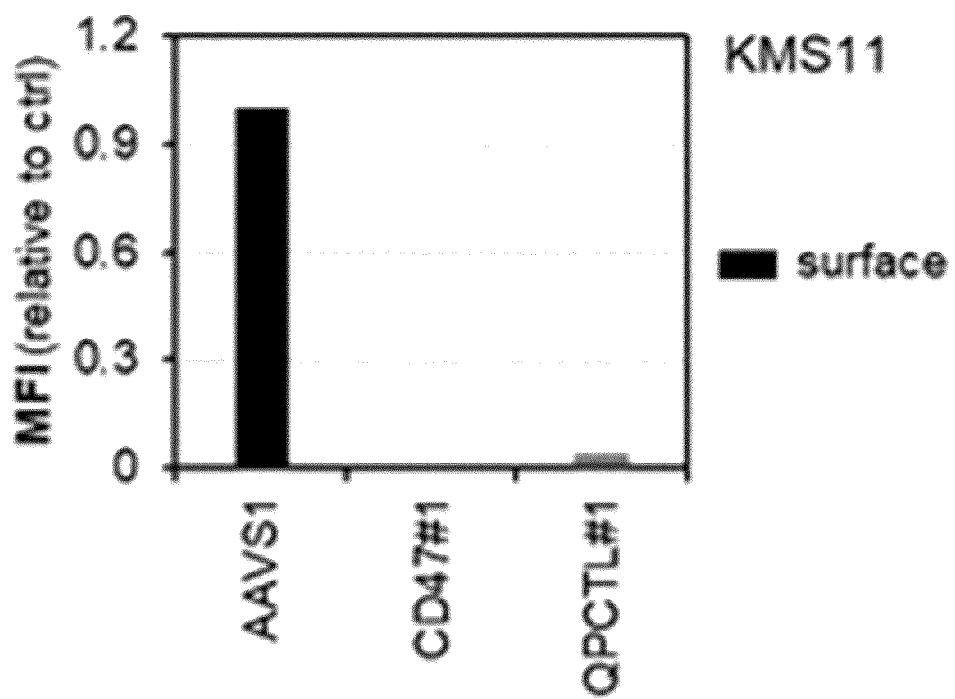
FIG. 16D is a graph illustrating the results of cell surface and intracellular flow cytometry (CC2C6 antibody) of KMS11 cells transduced with sgRNAs targeting CD47, QPCTL and QPCT as indicated, 25 days post-selection in minimal or rich medium. One representative experiment.

In order to identify positive and negative regulators of a biomarker of interest, a microfluidic chip allowing for collection of three subpopulations was designed: a bulk ("medium") population expressing baseline levels of the target biomarker, and two populations expressing either higher or lower levels (FIG. 3C). Cell sorting is facilitated by immunomagnetic labeling using antibodies coupled to magnetic beads. Magnetically-labelled cells are directed to their respective outlets using ferromagnetic guides made of Metglas 2714A, a cobalt-based magnetic alloy, and high-precision manipulation of magnetic drag force and buffer flow. Throughput was maximized by modifying width and height of the fluidic channel, and the ratio of sample to buffer volume. The MICS chip contains two sets of deflection guides, angled at 5° and 20° relative to the direction of flow to achieve an approximate 10/80/10% distribution of target cells in the low/medium/high outlets (FIG. 12A). At an optimized flow rate (FIG. 15A), the chip allows processing of $3 \times 10^7$ cells per hour per chip at sorting efficiencies of 73-92% (FIG. 15B). In an arrayed setup using 30 parallel chips as an example (see FIG. 3D), this platform can achieve sorting capacities of close to 1 billion cells per hour (FIG. 12B).

Figure 12C:
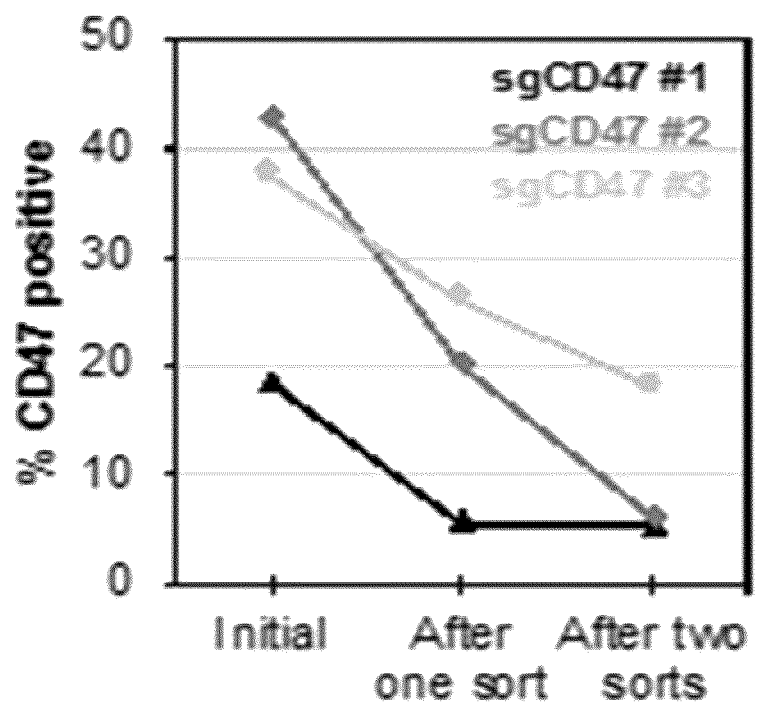
FIG. 12C is a graph illustrating sequential sorting of cells transduced with sgRNAs targeting CD47. CD47$^{low}$ cells were expanded after the primary sort, re-sorted 6 days later, expanded and analyzed by flow cytometry.
Figure 12D:
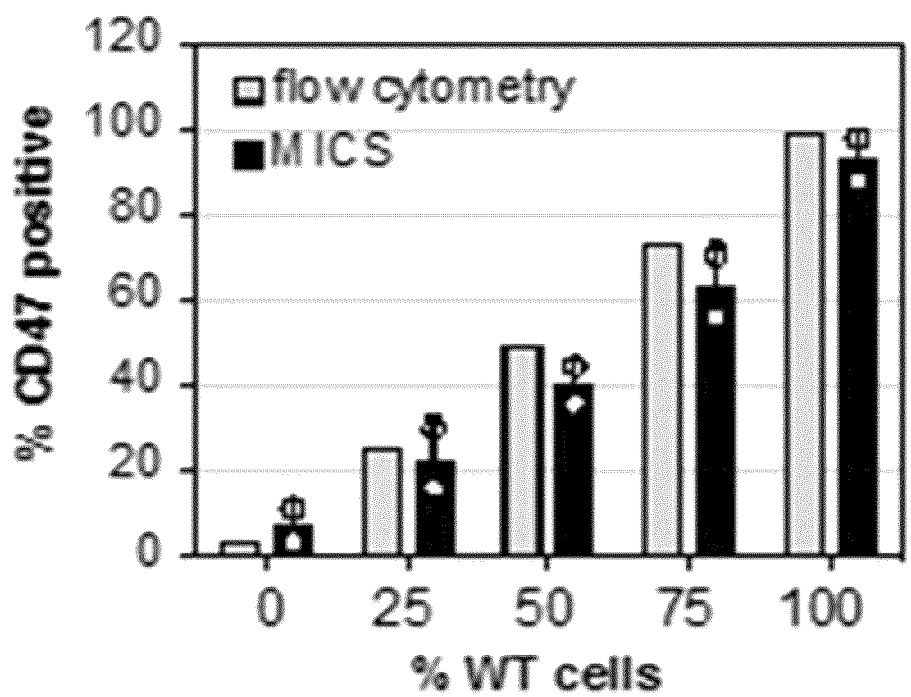
FIG. 12D is a graph illustrating the sorting of defined mixtures of WT and 2-sort-purified pooled CD47 (sgRNA #1) cells. Data represent n=2 technical replicates and mean±SD of triplicates. Flow cytometry data of same mixtures are shown for comparison.

For benchmarking the performance of MICS, an antibody targeting the SIRPα binding site on CD47 (CC2C6)[18,19], a biologically relevant site that modulates inhibitory interactions with macrophages and is currently being explored as a strategy for cancer immunotherapy[15], was chosen. HAP1 cells, a near-haploid mammalian cell line widely used for functional genetic screens[20,21] that robustly expresses CD47[22,23], were transduced, with Cas9 and single guide RNAs (sgRNAs) targeting CD47 and processed the mutants by MICS. In parallel, FACS-based cell sorting was performed. Detection of CD47$^{low}$ cells was comparable between both methods, and recovery (~80%) and cell viability (~90%) after MICS were high, allowing for a secondary sort for further enrichment of CD47$^{low}$ cells (FIG. 11C, FIG. 12C). Next, CD47 wild-type and knock-out cells were mixed in defined ratios and again accurate recovery by flow cytometry and MICS was observed (FIG. 12D).

Figure 13A:
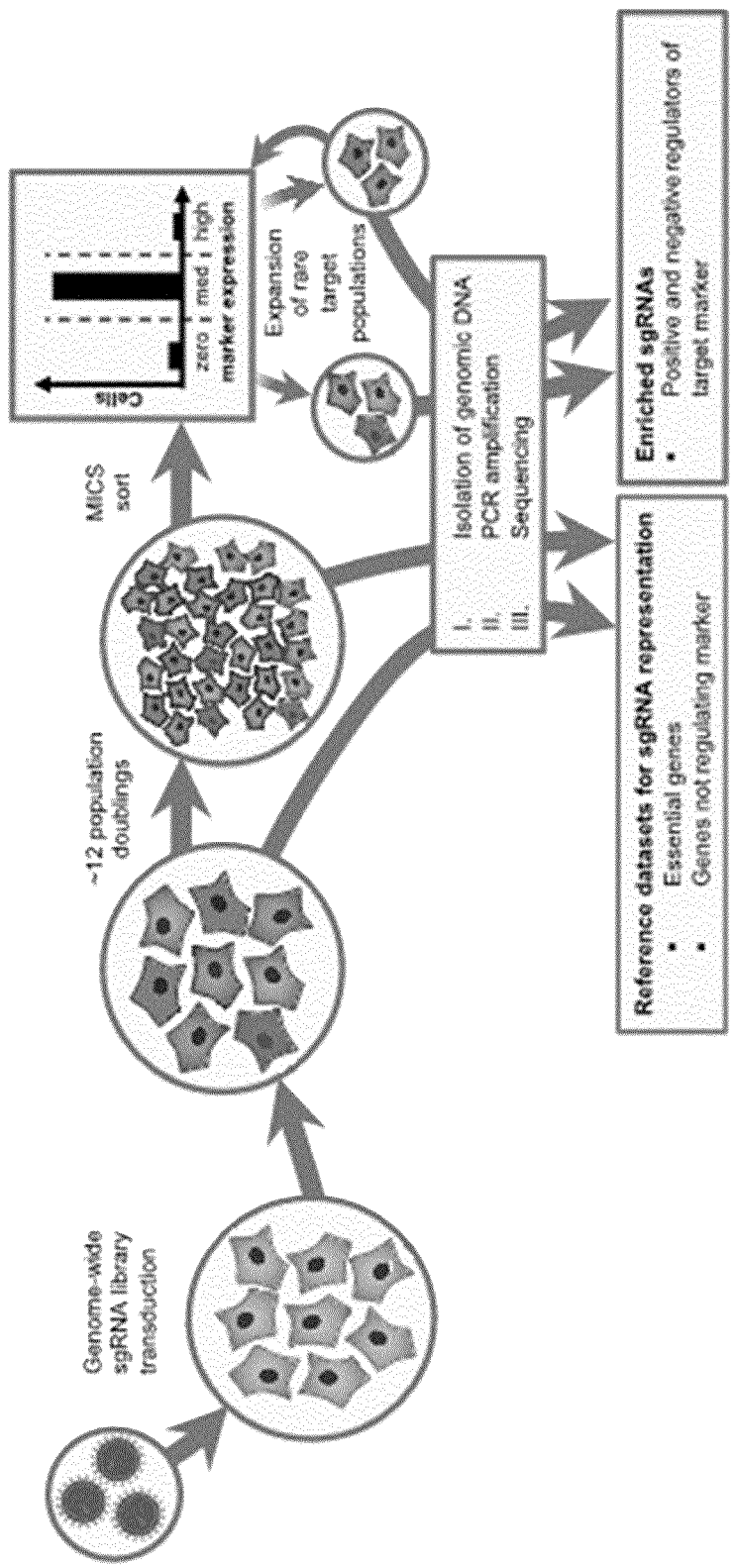
FIG. 13A is a schematic of CRISPR screen-work flow with two rounds of MICS sorting.

For a genome-scale proof-of-concept screen, HAP1 cells were then mutagenized using the Toronto KnockOut version 3.0 (TKOv3) CRISPR library[24-26]. The mutant pool was propagated for ~12 doublings and then subjected to two rounds of microfluidic sorting with recovery and expansion before re-sorting of rare mutants with altered CD47 levels (FIG. 13A). SgRNA abundance in each of the sampled populations was determined by deep sequencing and compared between the enriched and unsorted cell populations to identify candidate regulators of CD47 expression. In total, 3×10$^8$ target cells were processed on parallelized MICS chips driven by multiple syringe pumps. This arrayed setup allowed for bulk sample preparation, adding no extra processing time with increasing cell numbers, resulting in a net sorting time of ~1 hour (Table 1). For comparison, a FACS-based screen was performed using the same mutagenized cell pool, achieving—at best—sorting rates of 8×10$^7$ cells per hour, which is only possible with small, resilient, non-aggregating cell lines (Table 1). MICS was also compared with MACS-based sorting (Table 1), but this approach suffered from poor recovery of viable cells, and enrichment of CD47 sgRNAs was detected only in one of three replicates (Table 1). Extensive optimization of this approach was not pursued, but MACS is likely not amenable to separating cells with subtly different phenotypes.

Figure 13B:
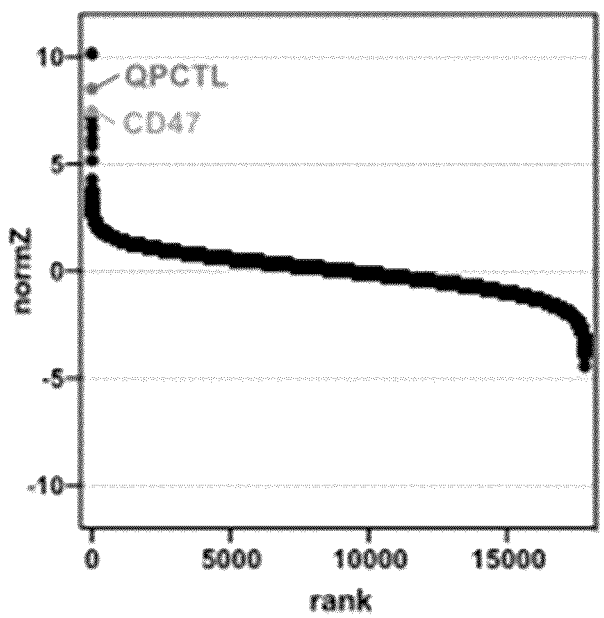
FIG. 13B is a graph illustrating the detection of genes targeted by sgRNAs in the MICS CD47$^{low}$ screen, ranked by FDR. The normZ score and FDR were calculated using drugZ.
Figure 13C:
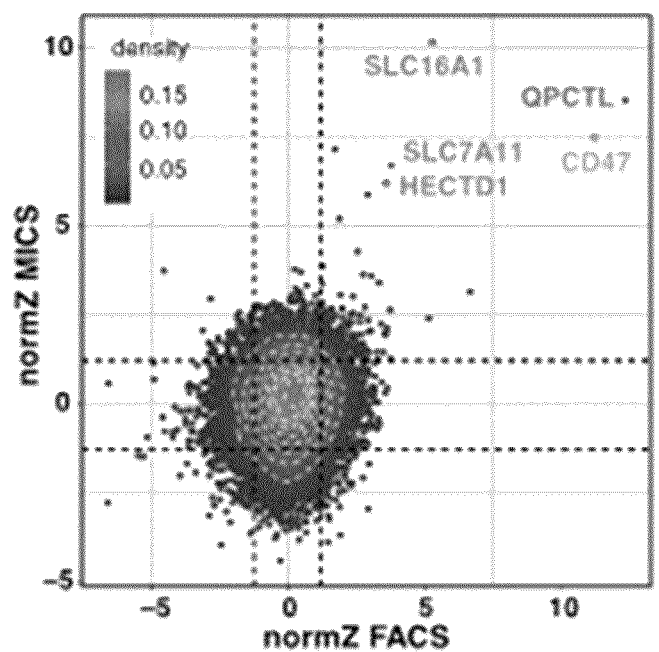
FIG. 13C is a comparison of MICS and FACS screen results for CD47$^{low}$. Displayed are normZ scores, coloured by density with contours indicated. Dashed lines represent the top and bottom 90th percentile of the data. Overlapping hits at <30% FDR are highlighted.
Figure 13D:
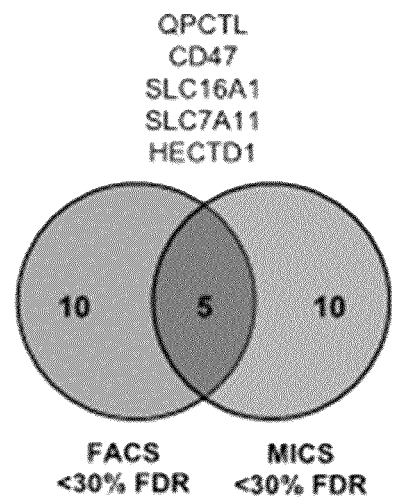
FIG. 13D is an overlap of hits from the MICS and FACS CD47$^{low}$ screens at <30% FDR.

Normalized z-scores[27] for the enriched sgRNAs were calculated in the CD47$^{high}$ and CD47$^{low}$ populations (FIG. 13B, 13C). CD47 was detected as a strong hit in the CD47$^{low}$ population by both methods (FIG. 13B, 13C). Of note, the three effective CD47 sgRNAs (FIG. 11C) were enriched in the CD47$^{low}$ population in both MICS and FACS, whereas the ineffective sgRNA (#4) was not. In addition to CD47, four other top-ranked hits (<30% FDR) overlapped between the FACS and MICS CD47$^{low}$ screens, of which QPCTL was the strongest (FIG. 13C, 13D), in line with a recent report of a gene-trap mutagenesis screen using the same antibody[28].

The QPCTL gene encodes glutaminyl-peptide cyclotransferase-like protein (also known as isoQC), a putative Golgi-resident enzyme and paralogue of the secreted glutaminyl-peptide cyclotransferase (QC, encoded by QPCT). Both enzymes catalyze the formation of N-terminal pyroglutamate (pyro-Glu) through cyclization of glutamine and glutamate residues[29,30]. Interestingly, an N-terminal pyro-Glu has been detected by crystallographic analysis of the CD47 protein and was suggested to mediate the interaction with SIRPα[31], but was assumed to arise spontaneously[32].

Figure 14A:
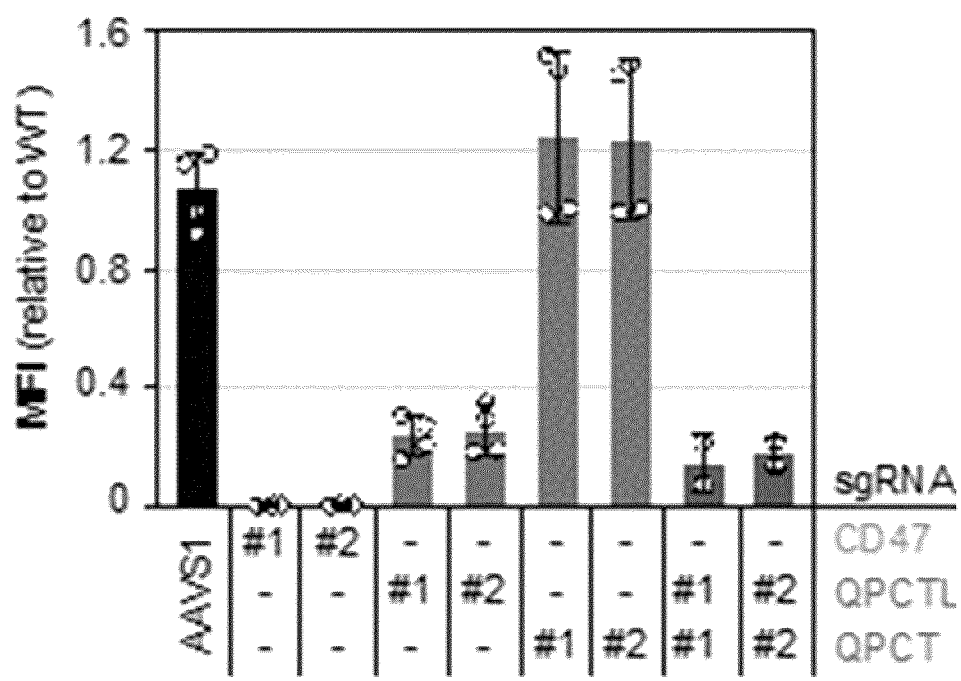
FIG. 14A is a graph showing the results of cell surface flow cytometry (using CC2C6 antibody) of HAP1-Cas9 cells transduced with sgRNAs targeting CD47, QPCTL and QPCT as indicated, 3-6 days post-transduction. AAVS1 sgRNA was used as control. Data represent mean±SD of the relative median fluorescence intensity (MFI, to wild-type) of n≥2 biological replicates from independent experiments. Last two bars, double knock-out.
Figure 14B:
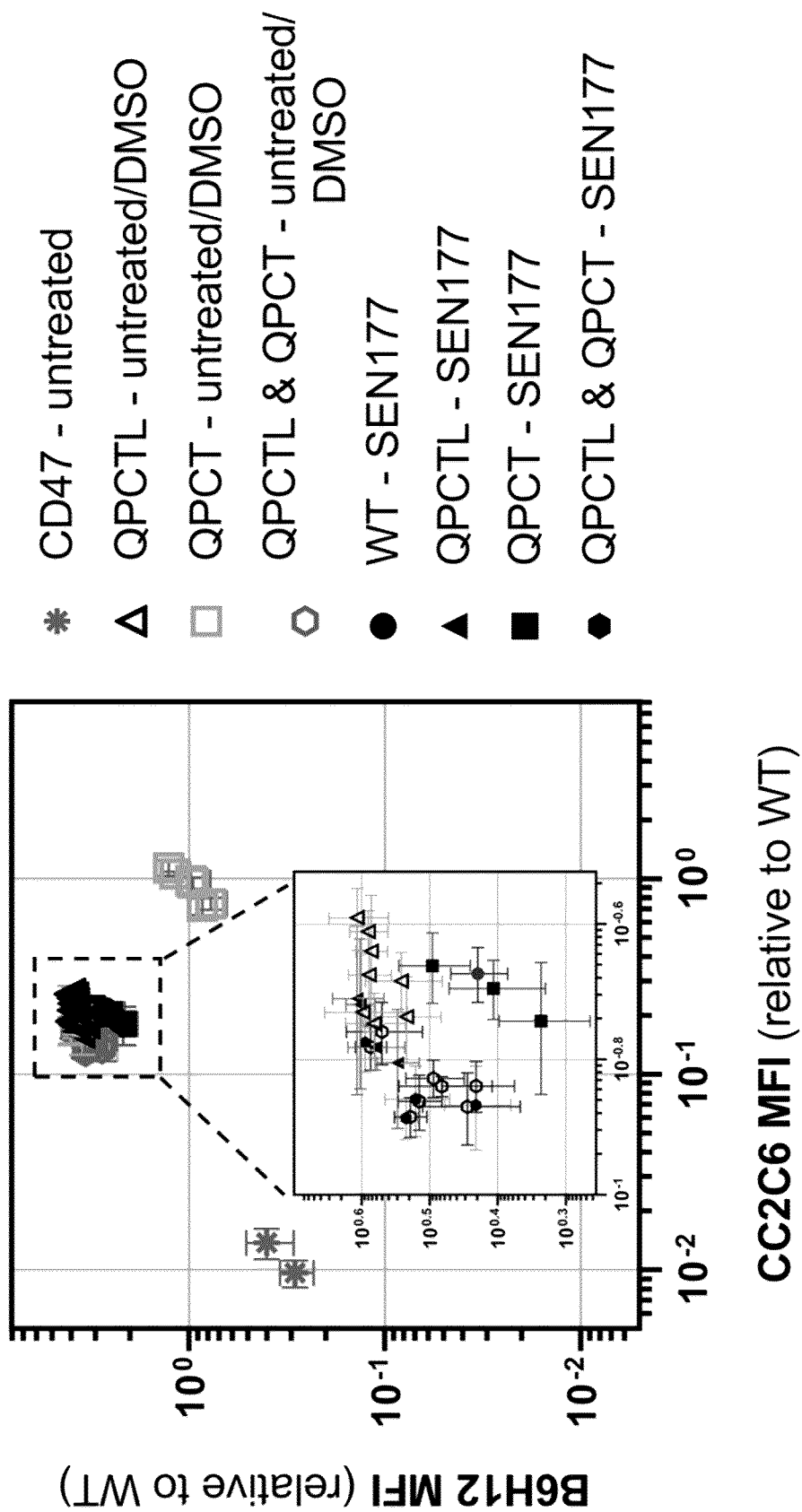
FIG. 14B is a graph of results from cell surface flow cytometry (CC2C6 and B6H12 antibodies) of HAP1 single cell knock-out clones for CD47, QPCT, QPCTL, and QPCT+QPCTL. Cells were either left untreated or treated with SEN177 (25 µM) or DMSO for 48 h. Data representation as in C, n=3 biological replicates from independent experiments, relative to wild-type (untreated) or wild-type+DMSO (treated). Inset shows close-up of QPCTL cluster.
Figure 14C:
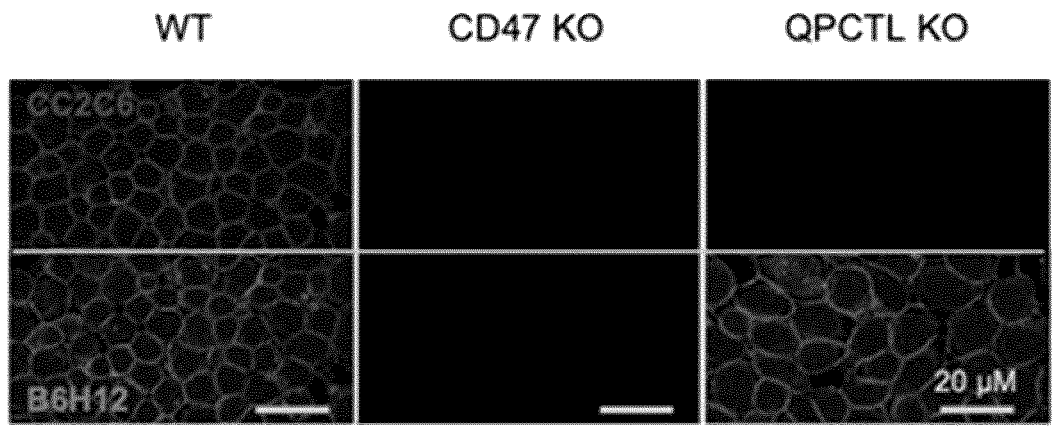
FIG. 14C are confocal images of immunofluorescent stained (using the CD47 CC2C6 and B6H12.2 antibodies, upper and lower panels, respectively) HAP1 single cell knock-out clones for CD47 and QPCTL. Scale bar=20 µm.
Figure 14D:
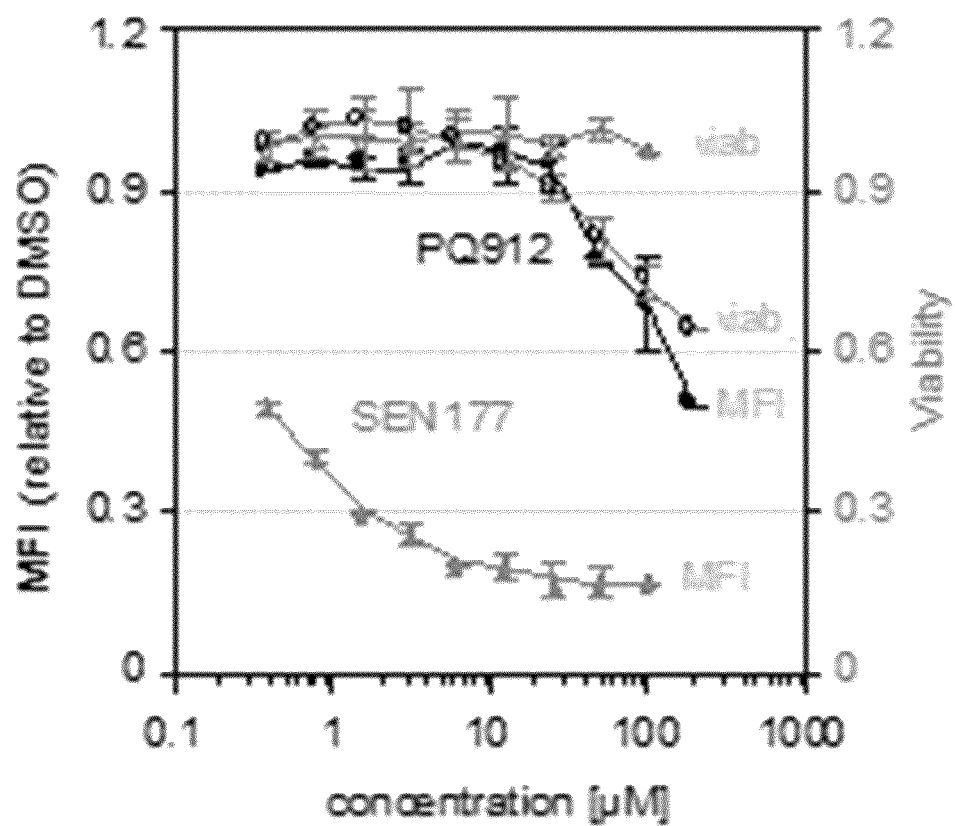
FIG. 14D are graphs from cell surface flow cytometry of HAP1 cells and viability after SEN177 or PQ912 treatment for 72 h. Data represent mean±SD of MFI or viability relative to DMSO-treated cells from n≥2 biological replicates from independent experiments.
Figure 14E:
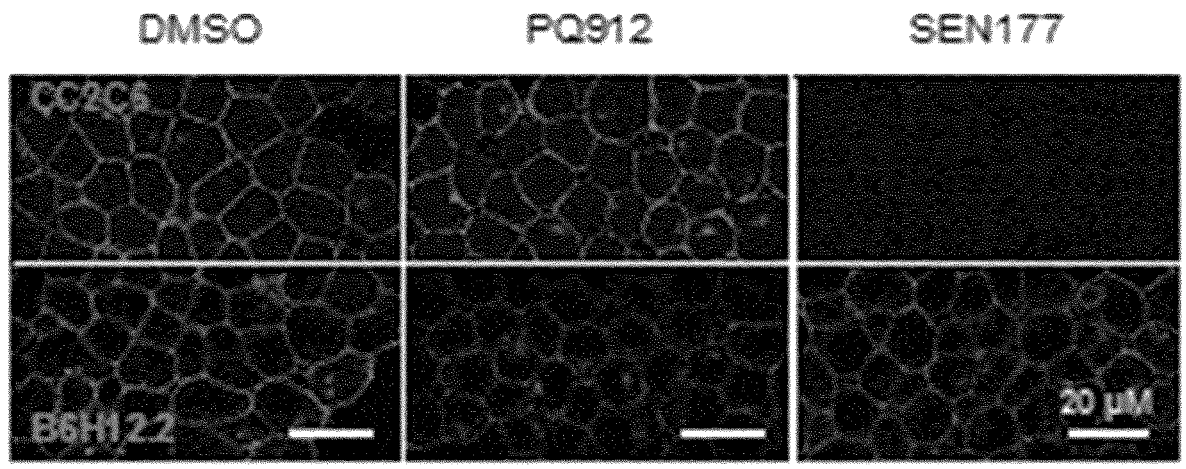
FIG. 14E are confocal images of immunofluorescent stained (as in C of SEN177- and PQ912-treated (both at 10 µM for 72 h) HAP1 cells.

Reduced levels of CD47 pyro-Glu modification (CD47$^{pyro-Glu}$) were confirmed—as determined by CC2C6 antibody binding—upon transduction of sgRNAs targeting QPCTL by cell surface and intracellular flow cytometry, as well as immunofluorescence imaging in HAP1, 293T and KMS11 cell lines (FIG. 14A-C; FIG. 16A-D). Loss of QPCT did not affect CC2C6 binding, and QPCT-QPCTL double targeting did not further reduce CD47$^{pyro-Glu}$ (FIG. 14A,B). Using a different CD47 antibody (B6H12), it was confirmed that overall CD47 protein expression and cell surface localization were not decreased upon inactivation of QPCTL (FIG. 14B,C). To establish that the enzymatic activity of QPCTL is required for the observed loss of CC2C6 binding, two small molecule inhibitors of QPCTL, SEN177[33] and PQ912[34-36] that are currently in clinical development for neurological diseases where pyro-Glu-mediated protein aggregation is involved were then tested. As expected, decreased CC2C6, but not B6H12 binding, was observed upon inhibitor treatment (FIG. 14B, 14D, 14E).

Figure 14F:
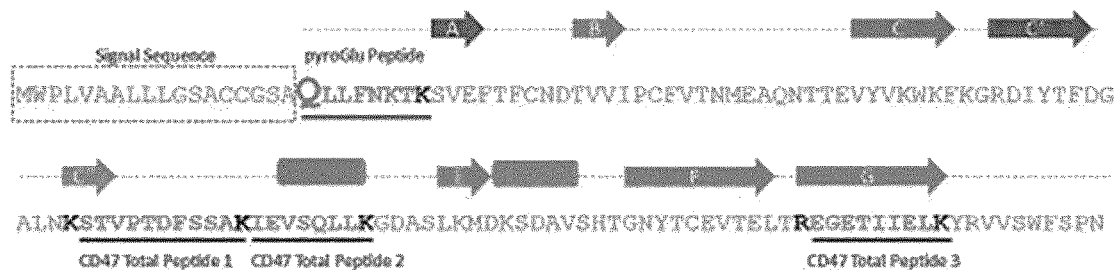
FIG. 14F is a schematic overlay of the secondary structure (cylinders for alpha helices and arrows for β-sheets) and the primary sequence of the IgSF domain of human CD47 (sequence is prior art). Four CD47 tryptic peptides utilized for PRM assays are underlined. Bolded lysine/arginine residues mark the tryptic peptide boundaries. Signal peptide sequence is boxed. The N-terminal glutamine residue (substrate for pyro-Glu cyclization) is enlarged.

Thus far, it was relied on indirect detection of the pyro-Glu modification through the CC2C6 antibody, assumed to bind specifically to CD47$^{pyro-Glu}$ [18,19,28]. To directly prove that loss or inhibition of QPCTL causes a reduction of pyro-Glu levels on the endogenous CD47 N-terminus, a targeted, quantitative mass spectrometry assay for this particular peptide was established (FIG. 14F). Notably, this is the first report of specific detection and direct quantification of endogenous pyro-Glu as a post-translational modification.

It was hypothesized that QPCTL (and QPCT) act on more than the few reported substrates[37-39]. An in silico prediction of mature human protein sequences was performed, assuming that the major mechanism of exposing non-Met N-terminal amino acids is signal peptide cleavage. This approach revealed ~600 candidates with predicted glutamine or glutamate residues at their N-terminus. As expected, most candidates are either secreted or membrane proteins, and some have been annotated with pyro-Glu modifications. Apart from CD47, the list of high-confidence candidates contains the exocrine tissue-associated prolactin-inducible protein (PIP), as well as many chemokines and immunoglobulins including the known QPCTL substrates CCL2 and CX3CL1[38,39]. Another high-confidence candidate is the angiogenic ribonuclease angiogenin, whose crystal structure confirmed the presence of an N-terminal pyro-Glu[40]. Finally, signaling proteins like Frizzled-7 (FZD7) and G-protein-coupled receptor C6A (GPRC6A) were also identified among potential QPCTL clients, warranting further investigation of the role of QPCTL in post-translational protein modification.

Here, it is demonstrated that MICS is a robust platform for functional genetic screening. An arrayed setup of MICS chips can surpass the throughput of traditional FACS-based immunosorting technologies by an order of magnitude, which will expand the applicability of functional phenotypic screening, including to fragile cell types. The MICS platform is also suitable for identifying negative regulators of a biomarker of interest, such as in the CD47$^{high}$ population of the described screen, or negative regulators of markers with low expression levels. Identifying negative regulators of CD47$^{high}$ would be of high interest, for instance to modulate immunogenicity in regenerative medicine settings[41].

MICS was applied to a genome-wide CRISPR-Cas9 loss-of-function screen, probing genetic regulators of CD47 and yielding overlapping hits with a parallel FACS-based screen. Most notably, QPCTL was identified and validated as a regulator of CD47$^{pyro-Glu}$, corroborating recent findings reporting QPCTL as a potential modifier of CD47-targeted cancer immunotherapy[28]. Supporting this role, high expression of QPCTL has been shown to be a poor prognostic indicator for renal cancer[42]. More detailed in vivo studies will be required to establish whether the modulation of QPCTL activity is an actionable strategy to boost macrophage-based cancer immunotherapy efficiency.

Interestingly, the screens also identified SLC16A1 and SLC7A11, which have been implicated in (free) pyro-Glu metabolism as transporters of pyro-Glu itself[43] or glutamine, respectively. Furthermore, the in silico prediction suggests that QPCTL could have additional substrate proteins, such as angiogenin, where an N-terminal pyro-Glu has been detected[40]. As for CD47, this modification has been assumed to occur spontaneously, and has been implicated in modulating the catalytic activity and cytotoxicity of angiogenin, as well as other RNase A homologues with N-terminal pyro-Glu[44-46]. This and other examples suggest that QPCTL (and QPCT) substrates could be involved in widespread biological, physiological and pathological processes, warranting further investigation of these poorly studied enzymes.

In sum, MICS is a robust, flexible, parallelizable and customizable high-throughput cell sorting platform particularly suitable for genome-scale screening applications.

TABLE 1

Comparison of sorting methods. See methods for details

|  | MICS | FACS[a] | MACS |
|---|---|---|---|
| Outlets | 3 (low, medium, high) | 2 (custom) | 2 (positive, negative) |
| Number of markers | 1 | multiple | 1 |
| Input CD47 screens |  |  |  |
| primary sort | $118 \times 10^6$ cells | $286 \times 10^6$ cells | $319 \times 10^6$ cells |
| secondary sort | $127 \times 10^6$ cells | $618 \times 10^6$ cells | $29 \times 10^6$ cells[b] |
| Recovery (mean ± SD) | 84.7 ± 54.93%[c,d] | 50.37 ± 12.79%[e] | 91.9 ± 11.85%[c] |
| Max. observed sort capacity | $299 \times 10^6$ cells/h[d] | $79 \times 10^6$ cells/h[f] | ~$106 \times 10^6$ cells/h |

[a]BD FACS Aria Illu
[b]only ⅓ replicates sorted, poor viability/proliferation after primary sort
[c]% of input in all outlets combined, averaged over primary/secondary sorts and all replicates
[d]includes numbers from an unrelated screen performed in parallel, sort time approximated by calculating inlet volume/actual flow rate
[e]% of expected (top and bottom 15% = 30% of input) in all outlets combined, averaged over all timepoints and replicates
[f]replicate C secondary sort CD47[low]

Methods

MICS device fabrication. See Example 1 and 2.

HAP1 cells. HAP1 cells were obtained from Horizon (clone C631, sex: male with lost Y chromosome, RRID: CVCL_Y019) and HAP1-Cas9 cells were generated as described.[24] For screening, HAP1 cells were cultured in "minimal" DMEM without sodium pyruvate, with sodium bicarbonate, 1.982 g/L glucose and 0.161 g/L L-glutamine (Wisent Bioproducts) with 10% FBS (Gibco) and 1% penicillin/streptomycin (ThermoFisher). For all other experiments, cells were cultured in standard medium (IMDM (Gibco) with 10% FBS (Gibco) and 1% penicillin/streptomycin (ThermoFisher)). The different media conditions do not alter CD47 levels or modification. Cells were cultured at 37° C. and 5% $CO_2$ in humidified incubators, were free of mycoplasma and routinely tested using the MycoAlert Detection Kit (Lonza).

Other cell lines. HEK293T (CRL-3216, sex: female, RRID: CVCL_0063) were obtained from ATCC and maintained in DMEM (Gibco) with high glucose, L-glutamine and sodium pyruvate, supplemented with 10% FBS (Gibco) and 1% penicillin/streptomycin (ThermoFisher). KMS11 (sex: female, RRID: CVCL_2989) were maintained in RPMI1640 with L-glutamine (Gibco), supplemented with 10% FBS (Gibco) and 1% penicillin/streptomycin (ThermoFisher). Cells were cultured at 37° C. and 5% $CO_2$ in humidified incubators, were free of mycoplasma and routinely tested using the MycoAlert Detection Kit (Lonza).

CRISPR sgRNA lentivirus production. pLCKO-TKOv3 plasmid library lentivirus was produced as described.[26] Briefly, HEK293T cells were seeded at a density of $9 \times 10^6$ cells per 15 cm plate and incubated overnight, after which cells were transfected with a mixture of psPAX2 (4.8 µg; Addgene #12260), pMDG.2 (3.2 µg; Addgene #12259), TKOv3 plasmid library (8 µg), and X-treme Gene9 (48 µl; Roche) in Opti-MEM (Gibco). 24 h after transfection, the medium was changed to DMEM with 1% BSA (Sigma) and 1% penicillin/streptomycin (Gibco). Virus-containing medium was harvested 48 h after transfection, centrifuged at 1500 rpm for 5 min, and stored at −80° C. Functional titers were determined by virus titration on HAP1 cells. 24 h after infection, the medium was replaced with puromycin-containing medium (1 µg/ml), and cells were incubated for 48 h. The multiplicity of infection (MOI) was determined 72 h after infection by comparing survival of infected cells to infected unselected and noninfected selected control cells. Lentivirus for individual sgRNA constructs was produced on smaller scale: HEK293T cells were seeded at a density of $0.5 \times 10^6$ per 6-well in low antibiotic growth media (DMEM with 10% FBS (Gibco), 0.1% penicillin/streptomycin) and incubated overnight. Cells were transfected with a mixture of psPAX2 (1800 ng), pMDG.2 (200 ng), sgRNAs in pLCKO or pLCV2[24,25] and X-treme Gene9 (12 µl) in Opti-MEM. 24 h following transfection, medium was changed to serum-free, high BSA growth medium as above. Virus-containing medium was harvested 48 h after transfection, centrifuged at 1500 rpm for 5 min, and stored at −80° C. Functional titers in cells for validation experiments were determined by virus titration.

Generation of CD47, QPCT and QPCTL knock-out cells. For transduction experiments using cell pools, single-stranded sgRNA oligos were annealed using T4 PNK in T4 ligation buffer (both NEB), and ligated into digested (BsmBI; NEB), phosphatase-treated (rSAP or CIP, NEB) and gel-purified modified pLCKO (for HAP1-Cas9) or pLCV2 (for HAP1, 293T and KMS11) backbones[24,25] using T4 DNA ligase. All plasmids were Sanger sequence verified and virus was prepared and titered as described above. HAP1, HAP1-Cas9 cells, 293T cells or KMS11 cells were infected with target and control gRNAs (MOI<1) in presence of 8 µg/ml polybrene. 24 h post infection, the medium was replaced with fresh medium containing puromycin (1 ug/ml for HAP1 and HAP1-Cas9, 1-2 ug/ml for 293T, 0.5 ug/ml for KMS11) and cells were incubated for 48 h. Cells were further cultured in selection-free medium as indicated for individual experiments (typically T3-T6), and passaged every 3-4 days. CD47 levels or modification did not in- or decrease with prolonged passaging up to T12 in HAP1-Cas9 cells. For infections with two sgRNAs (HAP1-Cas9 only), the second sgRNA was cloned into pLCKO hygro. Selection was carried out in puromycin (1 ug/ml) and hygromycin (800 ug/ml)-containing medium for the first 48 h, then in hygromycin-only medium for further 4-5 days. For single-cell knock-out clones (HAP1 only), sgRNAs were cloned into modified PX459v2.0 (from Addgene #62988, 1 kb stuffer sequence added). HAP1 cells were transfected using Lipofectamine 3000 (3.75 µl and 2.3 µg plasmid per 6-well), selected with puromycin for 48 h as above and seeded in limiting dilutions (1 cell/100 µl/96-well) 3 days later. Single-cell colonies were expanded, cryo-banked (in standard medium with 10% DMSO and a total of 20% FBS) and analyzed for mutations as described below. An sgRNA targeting the AAVS1 locus was used as negative control.

| sgRNA sequences: | |
|---|---|
| CD47#1 | AGCAACAGCGCCGCTACCAG |
| CD47#2 | GCACTTAAATATAGATCCGG |
| CD47#3 | GATAGCCTATATCCTCGCTG |
| CD47#4 | GAAGACTATACAACCTCCTA |
| QPCTL#1 | GGGTTCGCACAACCAGCAGG |
| QPCTL#2 | ACAGGGCACAGCCGAATCCG |
| QPCTL#3 | AGAGGCAAGAGCCGAACCCG |
| QPCTL#4 | GAGCAGTTGCAGGGTCACCG |
| QPCT#1 | TCAAGGATCACTCTTTGGAG |
| QPCT#2 | AGAGGCACCAGCCAACTGCA |
| QPCT#3 | GACCAAATGTCGTTTAGCAG |
| QPCT#4 | ACGAGCAGCATAGCTTCCAG |
| AAVS1 | GGGGCCACTAGGGACAGGAT | sgRNA sequences are from the TKOv3 library[25] and available through Addgene (Addgene, Watertown MA).

CRISPR editing analysis. For analysing indels after CRISPR-mediated editing, genomic DNA was isolated using the QIAamp DNA Blood Mini kit (Qiagen) or the Extracta DNA Prep kit (Quantabio). sgRNA target regions (100-200 bp up- and 500 bp downstream of sgRNA sequence) were amplified by touchdown PCR (−0.5° C./cycle from 72° C. to 60° C. plus 10 additional cycles at 59° C.) from 50-100 ng input DNA, PCR products were purified using the PureLink Quick PCR purification kit (Invitrogen) if necessary and analyzed by Sanger sequencing. Sequences were analyzed to determine the percentage of edited sequences contained in the sample using TIDE[49] and a "KO-score" using ICE[50] (Synthego). Non-edited cells amplified with the same primers were used as control samples. A representative analysis of double-sgRNA infected samples from two independent experiments yielded the following editing results for QPCT and QPCTL target loci (by sgRNA; mean percent edited/KO-score±SD): QPCTL #1 58.2/NA±16.2/N, QPCTL #2 33.23/47±32.96/0, QPCT #1 33.15/56±36.51/0, QPCT #2 80.2/76.4±19.85/2.42, QPCT #3 68.18/36.33±4.29/2.08; AAVS1/CD47 #1 (background or off-target, mean±SD over all QPCT and QPCTL target loci) 14.4/1.33±14.95/0.58. For single-cell derived clones, TIDE and ICE were used for screening purposes, and mutations were independently confirmed by PCR, Sanger sequencing and sequence alignment as described.

Primer sequences (fw and rv) for each sgRNA were designed.

MICS sorting. Cells were detached with 0.125% trypsin, washed once in PBS with 10% FBS, and resuspended at a concentration of $1\times10^7$ cells/ml in a solution of HBSS supplemented with 2% BSA. Cells were labelled for CD47 expression with biotin anti-human CD47 antibody (clone CC2C6, BioLegend, Cat. #323104, RRID: AB_756134) at 0.0625 μg/100 μl. Excess antibody was removed by washing twice in HBSS with 2% BSA. Cells were resuspended at $1\times10^8$ cells/ml, and anti-Biotin MicroBeads UltraPure were added at a 20% concentration by volume (Cat. #130-105-637, Miltenyi Biotec) and incubated at room temperature for 30 minutes. Cells were sorted by MICS at a concentration of ~$5\times10^6$ cells/ml in HBSS with 2% BSA; initial cell concentration was measured using a Countess Automated Cell Counter (Invitrogen). Syringe pumps (Fusion 200, Chemyx), operating in withdrawal mode, were used to drive flow in the MICS chips. Custom 3D-printed mounting hardware allowed for up to five stacks of three syringes (containing 20 ml, 10 ml and 3 ml syringes, Becton Dickinson) to be driven by the same pump (e.g. powering 5 chips). The different cross-sectional areas of the syringes were used to generate different flow rates, corresponding to the width of the low, medium and high outlet channels. Two inlet reservoirs, one containing the sample (cell) solution and one containing a flow focusing buffer stream (HBSS, 2% BSA) were connected to the two inlets of the MICS chip. The pump flow rate was chosen such that the sample flow rate was 6 ml/hr (with a total flow rate of 12 ml/hr). Sorted samples were collected in their respective syringes, and the volume of solution collected in each syringe was measured by weight. A small fraction (100 μl) of each sample was collected for cell counting to determine cell concentration after sorting. Each sample was stained with 1 μl of Syto24 Green nucleic acid stain (ThermoFisher Scientific) and incubated for 15 minutes at room temperature. Each sample was then loaded onto a 10-chambered microscope slide (Quick Read 3805, Globe Scientific) and cells were counted under fluorescent excitation using a custom counting macro and a Nikon TI Eclipse microscope. Sort efficiency was calculated by dividing the number of cells collected in the medium and high outlets by the total number of cells collected (low, medium and high). Recovery efficiency was defined as the percentage of input cells that were recovered in collected outlet populations. The fractions collected from the low/zero (21%, 24% and 30% of sorted cells for replicates A, B and C, respectively) and high outlets (10%, 18% and 15%) were collected in 15 ml falcon tubes on ice. Cells were then spun down, plated in minimal medium and cultured for 6 days prior to secondary sorting (for $CD47^{low}$ fraction from primary sort: 57%, 50% and 35% in low/zero; 1%, 1%, 2% in high). Sorted cells (low/zero and high) were pelleted for genomic DNA extraction. See Table 1 for input cell numbers, recovery and throughput.

Pooled genome-wide CRISPR screens in HAP1 cells. CRISPR screens in stable HAP1-Cas9 cells were performed essentially as described.[24,25] Briefly, $150\times10^6$ cells were infected with the TKOv3 lentiviral library at an MOI of ~0.3 (>400-fold coverage of the library after selection with puromycin). 24 h after infection, medium was changed to puromycin-containing medium (1 μg/ml). 72 h after infection, $100\times10^6$ puromycin-selected cells were cryo-banked, $90\times10^6$ cells were split into three replicates of $30\times10^6$ cells, passaged every 3-4 days and maintained at 400-fold coverage. $30\times10^6$ cells were collected for genomic DNA extraction at T0 after selection and at every passage until day 12 post selection, when sorting was performed. The unsorted T12 sample was used as reference. Genomic DNA extraction, library preparation and sequencing were performed as described below. For the FACS and MACS screens, $90\times10^6$ cryo-banked T0 cells were taken in culture, cultured until T12 as above and sorted as described below. The unsorted T12 sample was used as reference. All cell populations tested negative for mycoplasma pre- and post-sorting.

FACS and MACS sorting. Cells were detached with 0.125% trypsin, counted, and $2\times30\times10^6$ aliquots were pelleted for genomic DNA extraction. The remaining population was split in half for staining and sorting by FACS and MACS ($90-100\times10^6$ cells/replicate). For FACS sorting, cells were washed once in PBS and once in Flow buffer (PBS with 2% BSA) and stained with anti-human CD47-APC antibody (clone CC2C6, BioLegend, Cat. #323123/4, RRID: AB_2716202/3) in Flow buffer (20 µl antibody/40×10$^6$ cells/ml) for 1 h rotating at 4° C. in the dark. Cells were washed three times with Sort buffer (PBS with 1 mM EDTA, 25 mM HEPES pH7 and 1% BSA), resuspended in Sort buffer at 40×10$^6$ cells/ml, filtered through a 40 µm sieve and stained with 7AAD (BioLegend; 50 µl/40×10$^6$ cells/ml). Small aliquots were taken as single stain controls and stained as above. Sorting was performed on a BD FACS Aria Illu: 4 laser (405/488/561/633) 15 parameter cuvette based sorter with injection of approximately 40×10$^6$ cells/hr. The top and bottom 15% (gated on CD47 histogram of viable 7AAD-negative cells) were collected in 15 ml falcon tubes with minimal medium supplemented with 50% FCS on ice. Cells were then spun down, taken up in minimal medium, plated and cultured for 6 days. CD47$^{low}$ and CD47$^{high}$ cells were then detached, counted stained and sorted again as above (approx. 90-120×10$^6$ cells/replicate/fraction). Sorting gates were set using unsorted mutagenized cells that had been cultured in parallel. For MACS sorting, a MACS LS column mounted on a MidiMACS (Miltenyi Biotech) was used for sorting. Cells were labelled with magnetic nano-beads targeted to CD47 as described for MICS, suspended in HBSS supplemented with 2% BSA, and sorted through the column. The negative fraction was collected in 15 ml falcon tubes with minimal medium supplemented with 50% FCS on ice. Cells were then spun down, taken up in minimal medium, plated and cultured for 7-21 days. Only one replicate could be subjected to a secondary sort due to poor recovery and cell viability. Cells were pelleted after the secondary sort, and gDNA extraction, library preparation, sequencing and data analysis were performed as above. All cell populations tested negative for mycoplasma pre- and post-sorting. See Table 1 for input cell numbers, recovery and throughput.

Genomic DNA extraction and Illumina sequencing. Genomic DNA was extracted from screen cell pellets using the Wizard Genomic DNA Purification kit (Promega). Sequencing libraries were prepared by amplifying sgRNA inserts via a 2-step PCR using primers that include Illumina TruSeq adaptors with i5 and i7 indices. Resulting libraries were subsequently sequenced on an Illumina HiSeq2500 (RRID: SCR_016383) as described.[25] Each read was completed with standard primers for dual indexing with Rapid Run V1 reagents. The first 20 cycles of sequencing were dark cycles, or base additions without imaging. The actual 26-bp read begins after the dark cycles and contains two index reads, reading the i7 first, followed by i5 sequences.

Screen data processing and quality control. Sample reads were trimmed by locating the first 8 bp of the anchors used in the barcoding primers and extracting the flanking 20 bp after the anchor was found. A 2 bp mismatch was allowed for the anchor search. After trimming, a quality control alignment was performed using BOWTIE version 0.12.8 (allowing for max. 2 mismatches, ignoring qualities). For each sample, all available reads were combined from different sequencing runs if applicable, aligned using BOWTIE as described above, and sgRNAs tallied. Read counts for all samples in a screen were combined in a matrix and normalized by dividing each read count by the sum of all read counts in the sample and then multiplying by the expected read number (10 million). Fold change is calculated to a reference sample (T12 unsorted). The calculated fold-changes are then used to generate normZ scores using drugZ (version 1.1.0.2).[27]

Flow cytometry. Cells were dissociated with 0.125% trypsin and washed once in once in Flow buffer (PBS with 2% BSA). For cell-surface analysis, antibody staining was carried out in Flow buffer for 30 min on ice at 4° C. in the dark. For intracellular antigens, cells were first fixed with 4% PFA (Electron Microscopy Sciences) in PBS for 10 min on ice, followed by permeabilization using Flow buffer with 0.1% TritonX-100 (Sigma) for 5 min at room temperature. Cells were washed twice with Flow buffer, followed by staining for 30 min on ice at 4° C. in the dark. Stained cells were washed thrice with Flow buffer and 7-AAD viability dye (3-5 µl, BioLegend) was added before quantification. The following antibodies were used for these studies: anti-human CD47-APC (1 µl/10$^6$ cells in 100 µl; clone CC2C6, BioLegend, Cat. #323123/4, RRID: AB_2716202/3), anti-human CD47-FITC (5 µl/10$^6$ cells in 100 µl; clone B6H12, eBioscience, Cat. #11-0479-4/12, RRID: AB_2043842/3). Stained cells were quantified on an LSRII flow cytometer (BD Biosciences) or an iQue Screener PLUS (IntelliCyt), and data were analyzed using FlowJo software (RRID: SCR_008520). MFI was defined as median fluorescence across the population, and was generally displayed relative to wild-type cells in the same experiment.

Drug treatments. SEN177 (Sigma) and PQ912 (DC Chemicals) were dissolved in DMSO at 50 mM and added to cell medium at indicated concentrations. Cells were incubated for 12-72 h as indicated (without refreshing the drugs), and the same volume of DMSO was used as control.

Immunofluorescence microscopy. Cells were seeded onto poly-D-lysine coated 8-well micro slides (Ibidi). The next day, spent media was removed and cells were washed twice with PBS. Cells were loaded with Membrite™ Fix 488/515 cell surface staining kit (Biotium) per manufacturer's instructions. Subsequently, cells were washed twice with ice-cold PBS and fixed with 100% Methanol for 10 min at −20° C. After two additional washes with PBS, cells were incubated with a blocking solution (5% FBS with 0.05% Tween-20 in PBS) at room temperature for 1 h. Primary antibodies (anti-human CD47-APC; clone CC2C6, BioLegend, Cat. #323123/4, RRID: AB_2716202/3; and anti-human CD47; clone B6H12.2, ThermoFisher Scientific, Cat. #MA5-11895, RRID: AB_11009368) were added at 1:250 dilution in antibody dilution solution (1% FBS with 0.05% Tween-20 in PBS) and stained over night at 4° C. Secondary antibody (Alexa594-conjugated donkey anti-mouse; ThermoFisher Scientific, Cat. #A21203, RRID: AB_2535789) was added at 1:300 dilution in antibody dilution solution where necessary and incubated at room temperature for 1 h in the dark. Hoechst 33342 (ThermoFisher Scientific) was added at 1:5000 dilution in PBS and stained for 10 min. Finally, cells were washed twice in PBS and imaged on a Leica SP5 700 Confocal Microscope (Zeiss). For mean fluorescence intensity (MFI) measurements, Membrite™ staining intensity was used for automated image segmentation (ImageJ custom macro, available upon request) for operator independent unbiased selection of primary regions of interest (ROI) masks (in the green channel) and the mean fluorescence intensity was measured from the APC and/or Alexa594 channel. In total, 9 random fields of view were imaged per condition. MFI from wild-type untreated HAP1 cells was used to normalize all tested conditions to generate a relative CD47 expression metric.

Affinity precipitation and LC-MS/MS sample preparation. At 80-90% confluency, cells were harvested from 10 cm dishes by scraping and the cell pellets were washed twice in ice-cold PBS. For total cell lysate preparation, cells were lysed in RIPA buffer (ThermoFisher Scientific; supplemented with HALT protease and phosphatase inhibitor (ThermoFisher Scientific)) by incubation for 1 h at 4° C. with gentle rocking followed by 3 5-second sonication bursts at 10% amplitude. After a 13000×g spin for 30 min at 4° C., the supernatant was collected. Total protein concentrations were measured using the BCA Protein Assay kit (ThermoFisher Scientific). For immunoprecipitation of endogenous CD47, either clone B6H12.2 (for total protein; ThermoFisher Scientific, Cat. #MA5-11895, RRID: AB_11009368) or biotinylated CC2C6 (for pyro-Glu modified protein; BioLegend, Cat. #323104, RRID: AB_756134) anti-CD47 antibodies were used with Protein-G Dynabeads™ or Biotin-binder Dynabeads™, respectively, following manufacturer's instructions (ThermoFisher Scientific). For quantitative N-terminal CD47$^{pyro-Glu}$ modification detection, CD47 immunoprecipitates were eluted in 100 mM ammonium bicarbonate (pH 7.5) and digested with trypsin (ThermoFisher Scientific) overnight at 37° C. to generate tryptic peptides. Peptides were de-salted using PepClean™ C18 spin-columns following manufacturer's instructions (ThermoFisher Scientific).

High-performance liquid chromatography (HPLC). EASY-nLC 1200 (ThermoFisher Scientific) was coupled to the Q-Exactive MS (ThermoFisher Scientific) for peptide separation and detection. An EASY-Spray column (2 µm, 100A, 75 µm×50 cm; ThermoFisher Scientific) was employed for compound separation. Mobile phase A (0.1% formic acid in $H_2O$) and mobile phase B (0.1% formic acid in acetonitrile) were used with the following gradient: 0 min, 5% B; 50 min, 35% B; 55 min, 100% B; 60 min, 100% B at a flow rate of 225 nl/min.

Q-Exactive—PRM assays. Samples were analyzed using a Q-Exactive HF quadrupole Orbitrap mass spectrometer (ThermoFisher Scientific). 6 peptides were monitored through a PRM acquisition composed of 1 MS1 scan followed by 6 targeted MS/MS scans in high-energy collision dissociation with cycle times of 2.7s. For generating CD47-specific peptides suitable for the PRM assay, we purchased purified extracellular domain of human CD47 (G&P Biosciences) and used trypsin digestion as above to generate tryptic peptide-specific PRM transition profiles. The recombinant purified CD47 extracellular domain is expected to contain very little pyro-Glu modification (arising primarily due to spontaneous conversion). Acquisition was performed in positive ion mode for all 7 peptides. Due to a low number of target peptides, data acquisition was performed in an unscheduled MS/MS assay but retention times were noted.

Mass-spectrometry data analysis. PRM data acquired by LC-MS/MS was imported into Skyline for peak extraction and peak area calculation for each peptide. The top 3 fragments for each ion were used for quantification. For quantitative comparison across samples, DMSO control samples were used to generate a relative expression metric for both total CD47 protein expression and pyro-Glu modification across multiple conditions tested.

In silico prediction of QPCTL targets. To predict potential candidates for N-terminal pyro-Glu modification, knowledge of the first amino acid of the mature N-terminus (i.e. Q or E) is required. Many secretory or membrane proteins, as well as Golgi- and ER-resident proteins, contain signal peptides (SPs), which are proteolytically removed, revealing the mature N-terminus. As SP processing is a major (but not the only) proteolytic maturation event, we decided to use SP prediction tools to derive an approximation of a mature human proteome. FASTA sequences of human proteins were downloaded from Uniprot (filters: evidence at protein level and reviewed) and used as input for SignalP 4.0[51] (via SecretSanta[52]), signalHSMM[53] and Phobius[54]. All tools were run from within R. The following parameters were used for SignalP 4.0: version 4.1, organism 'euk', run_mode 'starter', sensitive TRUE. For signalHSMM, an SP probability cutoff of >0.45 was used. If a signal peptide was detected, the first residue after the predicted cleavage site was used as the new mature N-terminal amino acid, otherwise the original N-terminus was used. Proteins were grouped according to prediction confidence for putative Gln or Glu (Q or E) N-termini (by 0 tools=not detected, 1=low confidence, 2/3=high confidence). We then sub-classified the high-confidence group according to subcellular localization (downloaded from Uniprot followed by manual formatting) and previously detected pyro-Glu modification (downloaded from Uniprot, PDB and dbptm, http://dbptm.mbc.nct-u.edu.tw/; by 0 sources=not detected, 1=low confidence, 2/3=high confidence). Note that annotation with pyro-Glu in PDB does not necessarily predict direct modification due to the presences of multiple entities in a crystal structure. 67/86, 53/71 and 9/24 pyro-Glu annotations are in the high-confidence Q/E N-terminus group for Uniprot, dbptm and PDB, respectively. Localizations occurring at <2% of total were grouped together under "other".

Example 5

Microfluidic Parallelized Device

The single microfluidic chip device ("MICS platform") described in Examples 1 to 4 has a throughput capacity of 30 million cells per hour (per chip), requiring multiple chips to be run in parallel to sort the number of cells produced in a typical genome wide phenotypic CRISPR screen. Running chips in parallel is an effective method to carry out a single screen as shown in Example 3.

Another approach that increases operational capacity and facilitates fabrication is described.

The modified chip design, presented in FIG. 4, follows the same operating principles as the single MICS chip. Two sets of ferromagnetic guides angled at 5° and 20° induce deflection in magnetically labelled cells flowing in a central stream, with unlabeled cells unaffected by the magnetic field. Sorted cells are collected at one of three outlets, corresponding to low, medium or high target marker expression. This modified version is designed to deflect cells flowing in any one of 24 sample streams, all flowing in parallel, giving the updated design the potential for much higher throughput (e.g. over 200 million cells per hour).

Stereolithographic 3D printing was used to produce a parallelized device with a branching inlet and outlet channels permitting a sample of labelled cells to be split into 24 identical flowing streams. All of the fluidic components, including inlet and outlet ports, can be printed on a single resin cartridge. The ferromagnetic guides, which are patterned via wet etching, are patterned onto glass wafers using previously established techniques described for example in Example 2 and 3. The two main components are then clamped together and sealed using a custom Viton O-ring (see FIGS. 5A and 5B).

The present design permits the fluidic and magnetic components to be separated, allowing easier sterilization, drying and storing of individual chip components after use, allowing them to be reused multiple times. Having access to the internals of the chip opens up the possibility for more complex surface coatings to be applied to the magnetic separation layer, further reducing cellular friction and adhesion.

Example 6

Alternate Cell lines, Alternate Markers

The microfluidic device described in Example 1 and 2 (MICS) was also applied to larger cell types such as LNCaP and PC3 (FIG. 17A) and intracellular and surface markers expressed at lower density, e.g. EpCAM and vimentin (FIGS. 17B, C, E, F). The methods described in Example 4, modified for looking at EpCAM and vimentin and adjusting flow rate to accommodate the lower expression levels, were used.

At an optimized flow rate, MICS is provides a higher throughput and performs comparably in terms of for example cell viability to flow cytometry for both markers in both cell lines (FIGS. 17D, G;). These results demonstrate the flexibility of MICS as a customizable cell sorting platform.

Figure 17A:
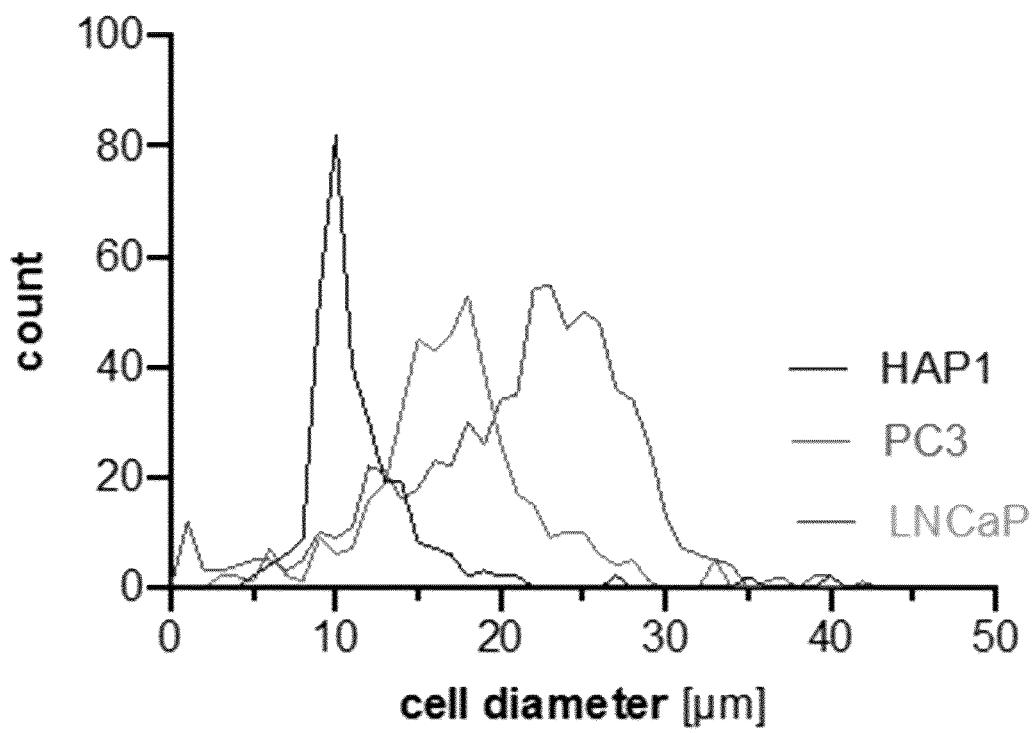
FIGS. 17A, B, C, D E, F and G are a series of graphs comparing sorting using a microfluidic chip device and HAP1, PC3 and LNCaP magnetically labelled cells.
Figure 17B:
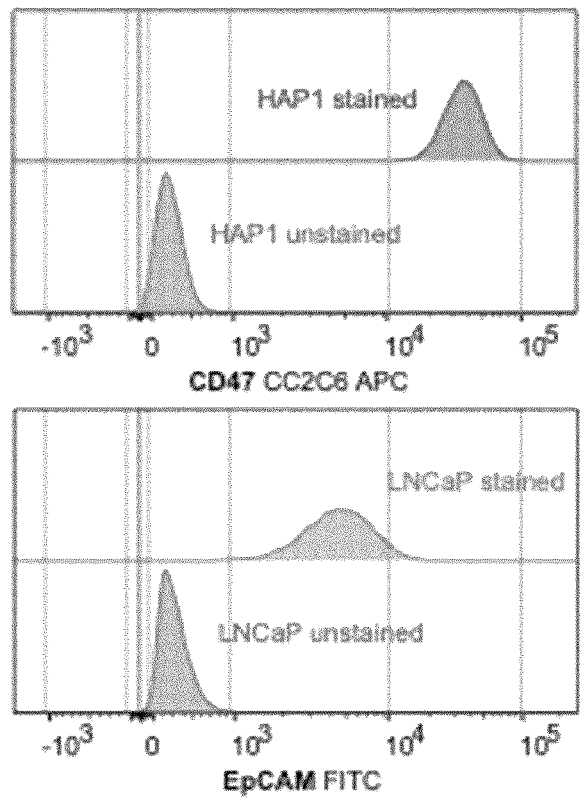
Figure 17C:
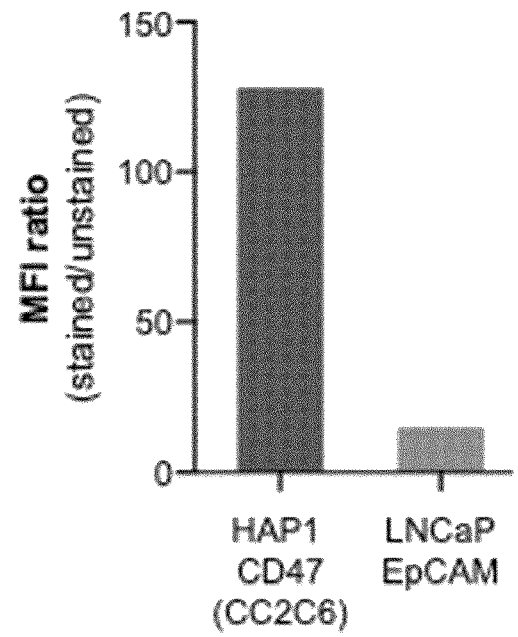
Figure 17D:
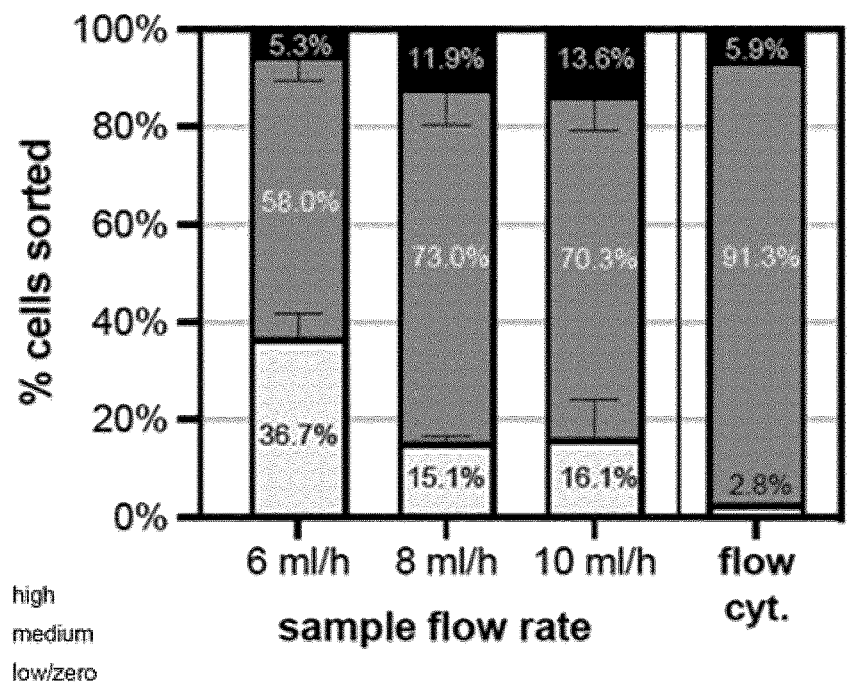

FIG. 17A is a graph showing cell size distribution and mean cell size of HAP1, PC3 and LNCaP cells (counted on Invitrogen Countess I after trypsinization). FIG. 17B is a series of flow cytometry histograms of CD47 (CC2C6 antibody) density on live HAP1 and EpCAM density on LNCaP cells. FIG. 17C shows the median Fluorescence Intensity (MFI) ratio of unstained vs. stained cells from FIG. 17B. FIG. 17D shows EpCAM-labelled LNCaP cells sorted by MICS at different flow rate. Displayed are percentages of cells detected in the 3 outlets (mean±SD of n=2-3 technical replicates) (black=high outlet, dark grey, medium outlet and light grey low/zero outlet). Flow cytometry data are shown for comparison (right bar). FIG. 17E, F are similar to FIG. 17B, C for live HAP1 (CD47 CC2C6) and fixed PC3 cells stained for vimentin. FIG. 17G. is similar to FIG. 17D, for fixed PC3 cells stained for vimentin.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

1. Trounson, A. & McDonald, C. Stem Cell Therapies in Clinical Trials: Progress and Challenges. *Cell Stem Cell* 17, 11-22, doi:10.1016/j.stem.2015.06.007 (2015).
2. Burr, M. L. et al. CMTM6 maintains the expression of PD-L1 and regulates anti-tumour immunity. *Nature* 549, 101-105 (2017).
3. Mezzadra, R. et al. Identification of CMTM6 and CMTM4 as PD-L1 protein regulators. *Nature* 549, 106-110 (2017).
4. Binek, A. et al. Flow cytometry has a significant impact on the cellular metabolome. *J. Prot. Res.* 18, 169-181 (2019).
5. Llufiro, E., Wang, L., Naser, F. J., Patti, G. J. Sorting cells alters their redox state and cellular metabolome. *Redox Biology* 16, 381-387 (2018).
6. Brockmann, M. et al. Genetic wiring maps of single-cell protein states reveal an off-switch for GPCR signalling. *Nature* 546, 307-311 (2017).
7. Wroblewska, A. et al. Protein barcodes enable high-dimensional single-cell CRISPR screens. *Cell* 175, 1141-1155.e16 (2018).
8. de Groot, R., Lüthi, J., Lindsay, H., Holtackers, R. & Pelkmans, L. Large-scale image-based profiling of single-cell phenotypes in arrayed CRISPR-Cas9 gene perturbation screens. *Mol. Syst. Biol.* 14, e8064 (2018).
9. Haney, M. S. et al. Identification of phagocytosis regulators using magnetic genome-wide CRISPR screens. *Nat. Genet.* 50, 1716-1727 (2018).
10. Parnas, O. et al. A Genome-wide CRISPR screen in primary immune cells to dissect regulatory networks. *Cell* 162, 675-686 (2015).
11. Han, X. et al. CRISPR-Cas9 delivery to hard-to-transfect cells via membrane deformation. *Sci. Adv.* 1, e1500454 (2015).
12. Han, X. et al. Microfluidic cell deformability assay for rapid and efficient kinase screening with the CRISPR-Cas9 system. *Angew. Chemie Int. Ed.* 55, 8561-8565 (2016).
13. Aldridge, P. M. et al. Prismatic deflection of live tumor cells and cell clusters. *ACS Nano* 12, 12692-12700 (2018).
14. Matlung, H. L., Szilagyi, K., Barclay, N. A. & van den Berg, T. K. The CD47-SIRPα signaling axis as an innate immune checkpoint in cancer. *Immunol. Rev.* 276, 145-164 (2017).
15. Weiskopf, K. Cancer immunotherapy targeting the CD47/SIRPα axis. *Eur. J. Cancer* 76, 100-109 (2017).
16. Advani, R. et al. CD47 blockade by Hu5F9-G4 and rituximab in non-hodgkin's lymphoma. *N. Engl. J. Med.* 379, 1711-1721 (2018).
17. Kong, F. et al. CD47: a potential immunotherapy target for eliminating cancer cells. *Clin. Transl. Oncol.* 18, 1051-1055 (2016).
18. Seiffert, M. et al. Human signal-regulatory protein is expressed on normal, but not on subsets of leukemic myeloid cells and mediates cellular adhesion involving its counterreceptor CD47. *Blood* 94, 3633-43 (1999).
19. Leclair, P. et al. CD47-ligation induced cell death in T-acute lymphoblastic leukemia. *Cell Death Dis.* 9, 544 (2018).
20. Carette, J. E. et al. Ebola virus entry requires the cholesterol transporter Niemann-Pick C1. *Nature* 477, 340-3 (2011).
21. Bürckstümmer, T. et al. A reversible gene trap collection empowers haploid genetics in human cells. *Nat. Methods* 10, 965-971 (2013).
22. Lee, S.-E. et al. Proteogenomic analysis to identify missing proteins from haploid cell lines. *Proteomics* 18, e1700386 (2018).
23. Paulo, J. A. & Gygi, S. P. Isobaric tag-based protein profiling of a nicotine-treated alpha7 nicotinic receptor-null human haploid cell line. *Proteomics* 18, e1700475 (2018).
24. Hart, T. et al. High-resolution CRISPR screens reveal fitness genes and genotype-specific cancer liabilities. *Cell* 163, 1515-1526 (2015).

25. Hart, T. et al. Evaluation and design of genome-wide CRISPR/SpCas9 knockout screens. *G3* 7, 2719-2727 (2017).
26. Mair, B. et al. Essential gene profiles for human pluripotent stem cells identify uncharacterized genes and substrate dependencies. *Cell Rep.* 27, 599-615.e12 (2019).
27. Colic, M. et al. Identifying chemogenetic interactions from CRISPR knockout screens with drugZ. *bioRxiv* 232736 (2019). doi:10.1101/232736
28. Logtenberg, M. E. W. et al. Glutaminyl cyclase is an enzymatic modifier of the CD47-SIRPα axis and a target for cancer immunotherapy. *Nat. Med.* 25, 612-619 (2019).
29. Cynis, H. et al. Isolation of an isoenzyme of human glutaminyl cyclase: retention in the golgi complex suggests involvement in the protein maturation machinery. *J. Mol. Biol.* 379, 966-980 (2008).
30. Stephan, A. et al. Mammalian glutaminyl cyclases and their isoenzymes have identical enzymatic characteristics. *FEBS J.* 276, 6522-36 (2009).
31. Hatherley, D. et al. Paired receptor specificity explained by structures of signal regulatory proteins alone and complexed with CD47. *Mol. Cell* 31, 266-277 (2008).
32. Ho, C. C. M. et al. "Velcro" engineering of high affinity CD47 ectodomain as signal regulatory protein a (SIRPα) antagonists that enhance antibody-dependent cellular phagocytosis. *J. Biol. Chem.* 290, 12650-12663 (2015).
33. Pozzi, C., Di Pisa, F., Benvenuti, M. & Mangani, S. The structure of the human glutaminyl cyclase-SEN177 complex indicates routes for developing new potent inhibitors as possible agents for the treatment of neurological disorders. *J. Biol. Inorg. Chem.* 23, 1219-1226 (2018).
34. Ramsbeck, D. et al. Structure-activity relationships of benzimidazole-based glutaminyl cyclase inhibitors featuring a heteroaryl scaffold. *J. Med. Chem.* 56, 6613-25 (2013).
35. Lues, I. et al. A phase 1 study to evaluate the safety and pharmacokinetics of PQ912, a glutaminyl cyclase inhibitor, in healthy subjects. *Alzheimer's Dement. Transl. Res. Clin. Interv.* 1, 182-195 (2015).
36. Hoffmann, T. et al. Glutaminyl cyclase inhibitor PQ912 improves cognition in mouse models of Alzheimer's disease-studies on relation to effective target occupancy. *J. Pharmacol. Exp. Ther.* 362, 119-130 (2017).
37. Kumar, A. & Bachhawat, A. K. Pyroglutamic acid: Throwing light on a lightly studied metabolite. *Curr. Sci.* 102, 288-297 (2012).
38. Kehlen, A. et al. N-terminal pyroglutamate formation in CX3CL1 is essential for its full biologic activity. *Biosci. Rep.* 37, (2017).
39. Cynis, H. et al. The isoenzyme of glutaminyl cyclase is an important regulator of monocyte infiltration under inflammatory conditions. *EMBO Mol. Med.* 3, 545-558 (2011).
40. Leonidas, D. D. et al. Refined crystal structures of native human angiogenin and two active site variants: implications for the unique functional properties of an enzyme involved in neovascularisation during tumour growth. *J. Mol. Biol.* 285, 1209-33 (1999).
41. Deuse, T. et al. Hypoimmunogenic derivatives of induced pluripotent stem cells evade immune rejection in fully immunocompetent allogeneic recipients. *Nat. Biotechnol.* 37, 252-258 (2019).
42. Uhlen, M. et al. A pathology atlas of the human cancer transcriptome. *Science* 357, eaan2507 (2017).
43. Sasaki, S., Futagi, Y., Kobayashi, M., Ogura, J. & Iseki, K. Functional characterization of 5-oxoproline transport via SLC16A1/MCT1. *J. Biol. Chem.* 290, 2303-2311 (2015).
44. Boix, E. et al. Role of the N terminus in RNase A homologues: differences in catalytic activity, ribonuclease inhibitor interaction and cytotoxicity. *J. Mol. Biol.* 257, 992-1007 (1996).
45. Liao, Y.-D. et al. The structural integrity exerted by N-terminal pyroglutamate is crucial for the cytotoxicity of frog ribonuclease from *Rana pipiens*. *Nucleic Acids Res.* 31, 5247-55 (2003).
46. La Mendola, D. et al. Copper binding to naturally occurring, lactam form of angiogenin differs from that to recombinant protein, affecting their activity. *Metallomics* 8, 118-24 (2016).
47. Ren, Y. et al. A simple and reliable PDMS and SU-8 irreversible bonding method and its application on a microfluidic-MEA device for neuroscience research. *Micromachines* 6, 1923-1934 (2015).
48. Luk, V. N., Mo, G. C. & Wheeler, A. R. Pluronic additives: a solution to sticky problems in digital microfluidics. *Langmuir* 24, 6382-6389 (2008).
49. Brinkman, E. K., Chen, T., Amendola, M. & van Steensel, B. Easy quantitative assessment of genome editing by sequence trace decomposition. *Nucleic Acids Res.* 42, e168-e168 (2014).
50. Hsiau, T. et al. Inference of CRISPR edits from sanger trace data. *bioRxiv* 251082 (2018). doi:10.1101/251082
51. Petersen, T. N., Brunak, S., von Heijne, G. & Nielsen, H. SignalP 4.0: discriminating signal peptides from transmembrane regions. *Nat. Methods* 8, 785-6 (2011).
52. Gogleva, A., Drost, H.-G. & Schornack, S. SecretSanta: flexible pipelines for functional secretome prediction. *Bioinformatics* 34, 2295-2296 (2018).
53. Burdukiewicz, M., Sobczyk, P., Chilimoniuk, J., Gagat, P. & Mackiewicz, P. Prediction of signal peptides in proteins from malaria parasites. *Int. J. Mol. Sci.* 19, 3709 (2018).
54. Käll, L., Krogh, A. & Sonnhammer, E. L. L. A combined transmembrane topology and signal peptide prediction method. *J. Mol. Biol.* 338, 1027-36 (2004).
55. Mahla, R. S. Stem Cells Applications in Regenerative Medicine and Disease Therapeutics. *Int J Cell Biol* 2016, 6940283, doi:10.1155/2016/6940283 (2016).
56. Wright, A. V., Nunez, J. K. & Doudna, J. A. Biology and Applications of CRISPR Systems: Harnessing Nature's Toolbox for Genome Engineering. *Cell* 164, 29-44, doi:10.1016/j.cell.2015.12.035 (2016).
57. Wang, T., Yu, H., Hughes, N. W., Liu, B., Kendirli, A., Klein, K., Chen, W. W., Lander, E. S. & Sabatini, D. M. Gene Essentiality Profiling Reveals Gene Networks and Synthetic Lethal Interactions with Oncogenic Ras. *Cell* 168, 890-903 e815,
58. Tibbe, A. G., de Grooth, B. G., Greve, J., Liberti, P. A., Dolan, G. J. & Terstappen, L. W. Optical tracking and detection of immunomagnetically selected and aligned cells. *Nat Biotechnol* 17, 1210-1213, doi:10.1038/70761 (1999).
59. Tibbe, A. G., de Grooth, B. G., Greve, J., Dolan, G. J., Rao, C. & Terstappen, L. W. Magnetic field design for selecting and aligning immunomagnetic labeled cells. *Cytometry* 47, 163-172 (2002).
60. Adams, J. D., Kim, U. & Soh, H. T. Multitarget magnetic activated cell sorter. *Proc Natl Acad Sci USA* 105, 18165-18170, doi:10.1073/pnas.0809795105 (2008).

61. Inglis, D. W., Riehn, R., Austin, R. H. & Sturm, J. C. Continuous microfluidic immunomagnetic cell separation. *Appl Phys Lett* 85, 5093-5095, doi:10.1063/1.1823015 (2004).
62. Amalou, F. & Gijs, M. in *Proceedings of IEEE Sensors.* 753-756 vol. 752.

The invention claimed is:

1. A microfluidic chip device for separating a magnetically labelled cell sample into subpopulations based on levels of a target marker, comprising:
   a) at least one inlet for receiving a sample and a buffer;
   b) a fluidic sorting channel fluidly connected to the at least one inlet, the fluidic sorting channel comprising a plurality of magnetic deflection guides wherein the plurality of magnetic deflection guides extend along a length of the fluidic sorting channel, wherein each magnetic deflection guide comprises a first segment having a first angle relative to the direction of flow and extending outwardly and a second segment having a second angle relative to the direction of flow and extending outwardly, and wherein the first segment intersects the second segment;
   c) two or more outlets fluidly connected to the fluidic sorting channel, each one of the outlets being configured to receive one subpopulation of the sample, the outlets comprising at least a first outlet and a second outlet; wherein
      i) high-level subpopulation collection stations are adjacent to first and second sides of the fluidic sorting channel and fluidly connected to the first outlet, such that the high-level subpopulation collection stations are configured to receive a first subpopulation expressing a first level of a target marker of interest;
      ii) medium-level subpopulation stations are adjacent to the high-level subpopulation collection stations and fluidly connected to the second outlet, the medium-level subpopulation collection stations being configured to receive a second subpopulation expressing a second level of a target marker of interest; and
      iii) low-level subpopulation collection stations are positioned between the medium-level subpopulation collection stations and fluidly connected to a third outlet, the low-level subpopulation collection stations being configured to receive a third subpopulation expressing a third level of a target marker of interest.

2. The microfluidic chip device of claim 1 wherein the first angle is selected from angles between about 2 to about 20 degrees.

3. The microfluidic chip device of claim 1 wherein the second angle is between 20 to 90 degrees.

4. The microfluidic chip device of claim 1 comprising a magnet positioned or fastened underneath the fluidic sorting channel to generate a magnetic field.

5. The microfluidic chip device of claim 4, wherein the magnet is a neodymium magnet.

6. The microfluidic chip device of claim 1 wherein the at least one inlet comprises a buffer inlet and a sample inlet and/or the plurality of magnetic deflection guides comprise cobalt-based magnetic alloy or nickel-iron magnetic alloy.

7. The microfluidic chip device of claim 1, wherein the plurality of magnetic deflection guides comprises two sets of magnetic deflection guides, wherein the first set is outwardly angled and directed to a first side of the fluidic sorting channel and the second set is outwardly angled and directed to a second side of the fluidic sorting channel.

8. The microfluidic chip device of claim 1, wherein the at least one inlet comprises a buffer inlet having bifurcated arms for directing the buffer to the sides of the sample to focus the sample stream.

9. The microfluidic chip device of claim 1, wherein each outlet comprises a collection bin for receiving a corresponding subpopulation of the sample.

10. A kit comprising a microfluidic device as claimed in claim 1.

* * * * *